US005856560A

United States Patent [19]
Bayer et al.

[11] Patent Number: 5,856,560
[45] Date of Patent: Jan. 5, 1999

[54] PREPARATION OF A-METHOXYIMINOCARBOXYLIC ACID METHYLAMIDES AND INTERMEDIATES THEREFORE

[75] Inventors: Herbert Bayer, Mannheim; Heinz Isak, Böhl-Iggelheim; Horst Wingert; Hubert Sauter, both of Mannheim; Michael Keil, Freinsheim; Markus Nett, Schifferstadt; Remy Benoit, Neustadt; Ruth Müller, Friedelsheim, all of Germany

[73] Assignee: BASF Aktiengesellschaft, Ludwigshafen, Germany

[21] Appl. No.: 750,822

[22] Filed: Dec. 10, 1996

[30] Foreign Application Priority Data

Jun. 10, 1994 [DE] Germany ............... 44 20 416.7

[51] Int. Cl.⁶ .................. C07C 59/86; C07C 69/73; C07C 231/06; C07C 229/36; C07C 249/08; C07C 251/24

[52] U.S. Cl. .................. 560/35; 560/51; 560/53; 560/60; 562/440; 562/450; 562/459; 562/470; 562/874; 564/124; 564/134; 564/149; 544/106; 544/224; 544/242; 546/192; 546/249; 548/202; 548/214; 548/235; 548/247; 548/255; 548/267.2; 548/335.5; 548/375.1; 548/566; 549/74; 549/80; 549/491; 558/371

[58] Field of Search .................. 562/450, 459, 562/470, 874, 440; 564/124, 134, 149; 560/35, 51, 53, 60

[56] References Cited

U.S. PATENT DOCUMENTS

| 5,194,662 | 3/1993 | Brand et al. . |
| 5,221,762 | 6/1993 | Wingert et al. ............. 560/35 |
| 5,358,968 | 10/1994 | Oberdorf et al. . |
| 5,393,920 | 2/1995 | Benoit et al. . |
| 5,530,156 | 6/1996 | Benoit et al. ............. 562/440 |

FOREIGN PATENT DOCUMENTS

| 2049162 | 3/1992 | Canada . |
| 2101664 | 2/1994 | Canada . |
| 2104806 | 3/1994 | Canada . |
| 398 692 | 11/1990 | European Pat. Off. . |
| 463 488 | 1/1992 | European Pat. Off. . |
| 477 631 | 4/1992 | European Pat. Off. . |
| 564 984 | 10/1993 | European Pat. Off. . |
| 579 124 | 1/1994 | European Pat. Off. . |
| 582 925 | 2/1994 | European Pat. Off. . |
| 585 751 | 3/1994 | European Pat. Off. . |
| 617 011 | 9/1994 | European Pat. Off. . |
| 617 014 | 9/1994 | European Pat. Off. . |
| 40 42 273 | 7/1992 | Germany . |
| 92/13830 | 8/1992 | WIPO . |
| 93/07116 | 4/1993 | WIPO . |
| 93/08180 | 4/1993 | WIPO . |
| 94/11334 | 3/1994 | WIPO . |
| 94/08948 | 4/1994 | WIPO . |
| 91/14761 | 7/1994 | WIPO . |
| 94/14322 | 7/1994 | WIPO . |
| 94/19331 | 9/1994 | WIPO . |
| 94/22812 | 10/1994 | WIPO . |

OTHER PUBLICATIONS

Hackh's *Chemical Dictionary*, Fourth Ed., McGraw–Hill Book Company (1969) pp. 249 and 424.
Dehydration of 1–o–Tolyl–2.2 . . . , Roger et al.
Friedel–Crafts–Type . . . Ohwada et al., J.am. Chem. Soc. 1991, 113, 1364–1373.
Chem. Abst., vol. 100, 1984, p. 5671.
Chem. Abst., vol. 96, 1982, p. 6335.
Chem. Abst., vol. 115, 1991, p. 964.
Chem. Abst. vol. 67, 1967, p. 6012.
A New Synthetic Method of Alkyl . . . , Shimizu et al., Bull Chem. Soc. Jpn., 58, 2519–2522.
Chem. Abst 92–265140/32.
Chem. Abst 93–285392/36.
Chem. Abst 93–348301/44.
Chadwick et al., Organic Chemistry, Part 2, p. 49 (George Allen & Unwin Ltd., London), 1971.
Howard et al., "Vinylogous Urethanes in Alkaloid Synthesis: Formal Synthesis of Elaeocarpus Alkaloids," Tetrahedron Letters, vol. 21, pp. 1373–1374, 1980.
Zagar et al., "The Paterno–Buchi Reaction of Achiral and Chiral Acyl Cyanides with Furan," Chem. Ber., vol. 124, pp. 967–969, 1991.
H.C. Martin, "Orthobenzoyl–Benzoyl Chloride," J. Am. Chem. Soc., vol. 38, pp. 1142–1144, 1916.
Rees et al., "Antimalarial Activities of Some 3,5–Diamino–as–triazine Derivatives," J. Med. Chem., vol. 15, No. 8, pp. 859–861, 1972.
Pearce et al., "Rearrangements of Azidoquinones, XV. Thermal Rearrangement of 2,3–Diazido–1,4–quinones to 2–Aza–3–cyano–1,4–quinones," J. Am. Chem. Soc., vol. 97, pp. 6181–6186, 1975.
Yagupol'skii et al., "Reaction of o–Phenylenediacetic Acid with Phosphorus Pentachloride," J. Org. Chem. USSR (Engl. Transl.), vol. 11, No. 12, pp. 2580–2584, 1975.
Griffin et al., "Synthesis and Photorearrangement of Substituted K–Region Arene Oxides," Tetrahedron Lett., No. 16, pp. 1239–1242, 1976.
Achmatowicz et al., "Chemia Cajanku Karbonylu. X. . . . ", Roczniki Chemii, vol. 35, pp. 813–819, 1961.
Connors et al., "Acyl cyanides as carbonyl heterodienophiles: application to the synthesis of naphthols, isoquinolones and isocoumarins," Can. J. Chem., vol. 74, pp. 221–226, 1996.
Roger et al., "The Dehydration of 1–o–Tolyl–2.2–Diphenyl Ethylene Glycol," Rec. Trav. Chim. Pays–Bas, vol. 56, pp. 202–207, 1937.
Philip J. Kocienski, "A Directed Aldol Approach to (+)–Milbemycin Beta–sub3," J. Chem. Soc. Perkin Trans., vol. 1, pp. 2171–2181, 1987.
Itoh et al., "Synthesis of Aryl Glyxolate. I. The Reaction of Alkyl Dichloro(alkoxy)acetates with Aromatics in the Presence of Lewis Acid," Bull. Chem. Soc. Jpn., vol. 57, No. 3, pp. 810–814, 1984.
M.L. Bouveault, "Sur les acides glyoxyliques de la serie aromatique," Bull. Soc. Chim. Fr., vol. 17, pp. 363–366, 1897.
Chuit et al., "Preparation de l'aldehyde p–isopropylphenyl–acetique et de quelques–uns de ses isomers et homologues," Bull. Soc. Chim. Fr., vol. 35, pp. 200–205, 1924.

*Primary Examiner*—Johann Richter

*Assistant Examiner*—Jane C. Oswecki
*Attorney, Agent, or Firm*—Keil & Weinkauf

[57] ABSTRACT

A process and intermediates for preparing α-methoxyiminocarboxylic acid methylamides (I) by Pinner reaction of a cyanoketone (II) with an alcohol and subsequent reaction of the resulting ester (IV) with hydroxylamine to give the oxime (V), methylation of (V) to give the oxime ether (VI) and subsequent reaction of (VI) with methylamine:

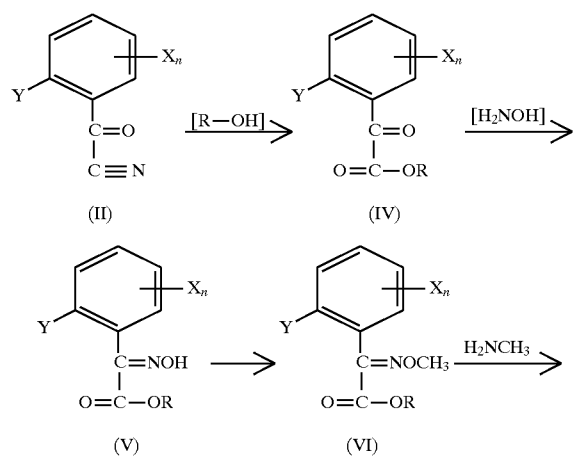

-continued

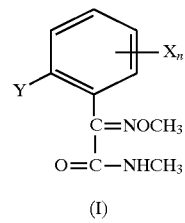

X = nitro, trifluoromethyl, halogen, alkyl or alkoxy;

n = 0, 1, 2, 3 or 4;

Y = a C-organic radical.

15 Claims, No Drawings

PREPARATION OF A-METHOXYIMINOCARBOXYLIC ACID METHYLAMIDES AND INTERMEDIATES THEREFORE

This application is a 371 of PCT/EP95/02013 filed May 26, 1995. The present invention relates to a process for preparing α-methoxyiminocarboxylic acid methylamides of the formula I

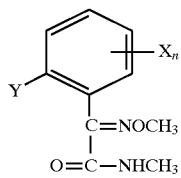

where
X is nitro, trifluoromethyl, halogen, $C_1$–$C_4$-alkyl or $C_1$–$C_4$-alkoxy,
n is 0 or an integer of from 1 to 4, where the X radicals can be different if n>1, and where
Y is a C-organic radical,
by Pinner reaction of an acyl cyanide of the formula II

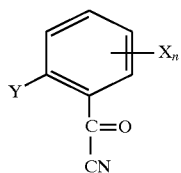

with an alcohol and subsequent reaction of the ester formed in the Pinner reaction, of the formula IV

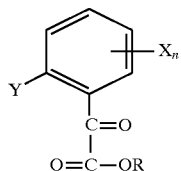

a) with hydroxylamine to give the oxime of the formula V

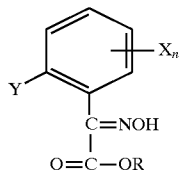

methylation of V to give the oxime ether of the formula VI

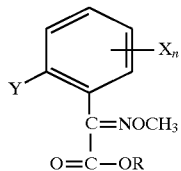

or
b) with O-methylhydroxylamine to give the oxime ether of the formula VI
and subsequent reaction of VI with methylamine.

Various processes for preparing α-methoxyiminocarboxylic acid methylamides are disclosed in the literature. As a result of the many steps required, however, these processes are involved and/or do not afford satisfactory yields or they necessitate the use of reagents which are expensive or difficult to handle in large-scale processes (cf. EP-A 398 692, EP-A 463 488, EP-A 477 631, EP-A 579 124, EP-A 582 925, EP-A 585 751, EP-A 617 011, EP-A 617 014, WO-A 92/13,830, WO-A 93/07,116, WO-A 93/08,180, WO-A 94/08,948, WO-A 94/11,334, WO-A 94/14,322, WO-A 94/14,761, WO-A 94/19,331, WO-A 94/22,812, JP-A 04/182,461, JP-A 05/201,946, JP-A 05/255,012, DE Appl. No. 44 10 424.3 and DE Appl. No. 44 21 182.1).

The Pinner reaction of cyanoketones of the formula II with methanol and the subsequent reaction to give the corresponding methyl α-methoxyiminocarboxylates I' is additionally disclosed in the literature (EP-A 493 711). This process, however, has the disadvantage that, on the one hand, in addition to the desired ketoesters benzoic acid esters, ketal esters and amides are also formed to a not inconsiderable extent.

The known process additionally has the following disadvantage: If the particularly preferred compounds IIA' (Y is chloromethyl)

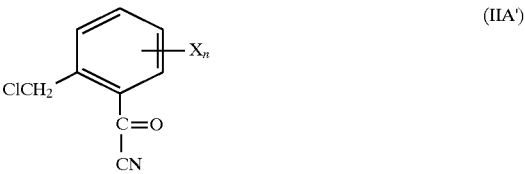

are prepared, eg. by the methods given in DE-A 42 23 382 and DE-A 43 11 722, and then reacted with methanol to give the ketoesters X

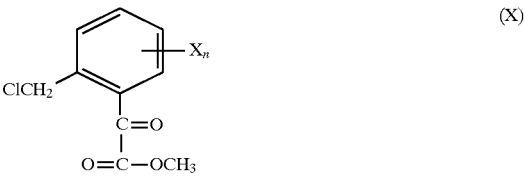

the preparation of X in pure form presents great difficulties. The reason for this is that the physical properties of the ketoesters X and of the by-products (in particular subst. phthalide and subst. 2-chloromethylbenzoyl chloride) carried over from the first two reactions (according to DE-A 42 23 382 and DE-A 43 11 722) are very similar, such that purification, eg. by distillation, is only possible with difficulty and at great expense, if at all.

The use of the ketoesters obtainable by the known process therefore leads to contaminated secondary products, which can only be purified with difficulty.

It is an object of the present invention to make available a process for preparing α-methoxyiminocarboxamides, which is simple and can be used on a large scale, in particular can be carried out without expensive or questionable reagents and additionally allows preparation of the desired intermediates and final products in pure form.

We have found that this object is achieved by a process for preparing α-methoxyiminocarboxylic acid methylamides of the formula I

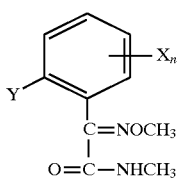

where
- X is nitro, trifluoromethyl, halogen, $C_1$–$C_4$-alkyl or $C_1$–$C_4$-alkoxy,
- n is 0 or an integer of from 1 to 4, where the X radicals can be different if n>1, and where
- Y is a C-organic radical, by Pinner reaction of an acyl cyanide of the formula II

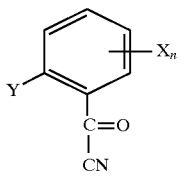

with an alcohol and subsequent reaction of the ester formed in the Pinner reaction, of the formula IV

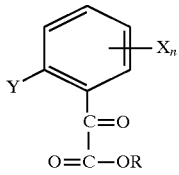

a) with hydroxylamine to give the oxime of the formula V

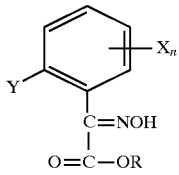

methylation of V to give the oxime ether of the formula VI

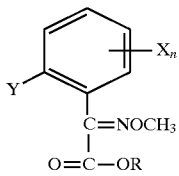

or b) with O-methylhydroxylamine to give the oxime ether of the formula VI and subsequent reaction of VI with methylamine, which comprises using in the Pinner reaction an alcohol of the formula III

R—OH       (III)

whose boiling point is above 75° C.

The process is based in principle on the fact that by the use of relatively high-boiling alcohols in the Pinner reaction α-ketoesters are formed which are likewise relatively poorly volatile. The boiling point range between the desired product and the undesired by-products thereby increases and separation by distillation is possible. When using relatively high-boiling alcohols, the formation of the by-products additionally decreases, such that the desired product can be obtained more selectively and in better yields.

In the process according to the invention, a procedure is in general used in which a mixture of alcohol, acid and, if appropriate, inert solvent is treated at from −10° C. to 150° C., preferably from 20° C. to 130° C., in particular from 50° C. to 110° C., with the acyl cyanide II.

All alcohols whose boiling point at normal pressure is above 75° C., preferably above 90° C., in particular above 120° C., are fundamentally suitable for the process according to the invention. Examples of alcohols of this type are ethanol, n-propanol, isopropanol, n-butanol, sec-butanol, isobutanol, tert-butanol, n-pentanol and its isomers, n-hexanol and its isomers, heptanol, octanol, nonanol or decanol and the respective isomeric haloalcohols such as 2-chloroethanol, 3-chloropropanol, 4-chlorobutanol, 5-chloropentanol, 6-chlorohexanol, 7-chloroheptanol, 8-chlorooctanol or 9-chlorononanol and the respective isomers and also alkoxyalkanols such as 2-methoxyethanol, 2-ethoxyethanol, 3-methoxypropanol, 3-ethoxypropanol, 4-methoxybutanol, 4-ethoxybutanol, 5-methoxypentanol, 5-ethoxypentanol, 6-methoxyhexanol, 6-ethoxyhexanol, 7-methoxyheptanol, 7-ethoxyheptanol, 8-methoxyoctanol, 8-ethoxyoctanol, 9-methoxynonanol or 9-ethoxynonanol and the respective isomers.

Ethanol, 1-propanol, 2-propanol, 1-butanol, 2-butanol, 2-methyl-1-propanol, 1-pentanol, 2-pentanol, 3-pentanol, 3-methyl-1-butanol, 2,2-dimethyl-1-propanol, 1-methyl-2-butanol, 2-methyl-1-butanol, 3-methyl-2-butanol, 1-hexanol, 2-methoxyethanol, 2-ethoxyethanol, 3-octanol, 1-heptanol, 1-octanol and 2-chloroethanol are particularly preferred. n-Pentanol is very particularly preferred.

The amount of alcohol employed is not critical for the process according to the invention. In general, from 1 to 10 mol of III, preferably from 1 to 5 mol of III, in particular from 1 to 3 mol of III, are used per mole of acyl cyanide II employed. The alcohol can also be used as a solvent. In this case, an excess of at least 20 mol, preferably at least 10 mol, in particular at least 5 mol, is used per mole of acyl cyanide II.

All inorganic or organic acids which can be used according to the literature for the Pinner reaction can be used as the acid. Mineral acids (eg. sulfuric acid and phosphoric acid, in particular hydrohalic acids such as hydrochloric acid and hydrobromic acid) are preferably used.

The acids are generally employed in an excess of from 1 mol to 5 mol, preferably from 2 mol to 5 mol, in particular from 2.5 mol to 3.5 mol, per mole of acyl cyanide II.

Suitable inert solvents are aprotic polar or non-polar organic solvents, for example hydrocarbons (eg. pentane, hexane, cyclohexane, petroleum ether), aromatic solvents (eg. benzene, toluene, o-, m- or p-xylene, chlorobenzene, nitrobenzene and anisole), halogenated hydrocarbons (eg. dichloromethane, trichloromethane, tetrachloromethane and 2,2'-dichloroethane) and ethers (eg. diethyl ether, diisopropyl ether, tert-butyl methyl ether, tetrahydrofuran, tetrahydropyran, dioxane or anisole), or mixtures of the solvents mentioned.

The Pinner reaction is preferably carried out in the presence of water, amounts of from 0.5 to 1.5 mol of water per mole of acyl cyanide customarily being used.

The amount of inert solvent is not critical for the process according to the invention. As a rule, from 2% by weight to 40% by weight of solvent can be employed, based on the acyl cyanide II.

As a rule, the reaction is carried out at atmospheric pressure or at the autogenous pressure of the respective reaction mixture. A higher or lower pressure is also possible but in general does not offer any additional advantage.

The reaction mixtures are worked up in a customary manner, eg. by mixing with water, separating the phases and, if appropriate, purifying the crude products by chromatography. The intermediates and final products are in some cases obtained in the form of colorless or slightly brownish, viscous oils, which are freed from volatile components under reduced pressure and at moderately elevated temperature or are purified (if appropriate by way of a preliminary distillation). If the intermediates and final products are obtained as solids, purification can also be carried out by recrystallizing or digesting.

The acyl cyanides II required for the reaction are obtainable, for example, from the corresponding phthalides by the methods described in DE-A 42 23 382, EP-A 493 711, EP-A 564 984 and in DE-A 43 11 722. The disclosure of these specifications is hereby included.

In the process according to the invention, it was hitherto not possible to observe the formation of ketal esters of the formula IV''

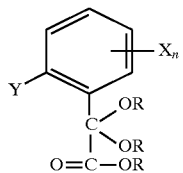

If these ketals IV'' were nevertheless to occur sometimes as by-products, these by-products, however, would not interfere with the further use of the ketoesters IV for the synthesis of the compounds I, as they would be cleaved and additionally reacted under the reaction conditions of the subsequent reaction. If desired, the ketocarboxylic acid ester dialkyl ketals IV'' could, however, also be converted to the ketoesters IV under acidic conditions, for example by passing in hydrogen chloride in the presence of an inert solvent.

In addition, the corresponding α-ketocarboxamides IV' can be formed in the Pinner reaction. If the α-ketocarboxamides IV' are unrequited, the crude product mixture is expediently subjected to the Pinner reaction again, namely several times if appropriate, whereby the α-ketocarboxamides IV' are converted to the ketoesters IV. The by-products of the formula IV' are formed to a considerably lower extent by the process according to the invention than is the case in known processes.

The alcoholysis of the α-ketocarboxamides IV', however, can also be carried out in a separate process step, for example by treatment with acid and the alcohol R—OH, if desired in the presence of a diluent, eg. a hydrocarbon such as toluene, a halohydrocarbon such as dichloromethane, trichloromethane or carbon tetrachloride or an ether such as diethyl ether, diethylene glycol, tetrahydrofuran or dioxane. Suitable acids are, for example, mineral acids such as hydrochloric acid, sulfuric acid or phosphoric acid, carboxylic acids such as acetic or trifluoroacetic acid, or sulfonic acids such as p-toluenesulfonic acid. Preferred acids are sulfuric acid, in particular as a concentrated aqueous solution, and hydrochloric acid, which is particularly preferably passed in as a gas.

The formation of the oxime ethers VI can be carried out by reacting with O-methylhydroxylamine or one of its acid addition products, starting from the ketoesters IV or the α-ketocarboxamides IV'. Mixtures of these compounds are moreover suitable as starting substances, it also being possible to further react the crude product mixture obtained by the Pinner reaction without further purification.

The O-methylhydroxylamine is either employed in the form of an acid addition salt or as a free base, it also being possible for the unprotonated compound to be liberated from the salt by addition of a strong base. Suitable salts of O-methylhydroxylamine are the salts with mono- to tribasic acids such as, in particular, hydrochloric acid and sulfuric acid. The use of acid addition salts is preferred.

In general, the reaction is carried out in the presence of a solvent or diluent. Suitable solvents are preferably aromatic hydrocarbons such as benzene, toluene and o-, m- or pxylene, chlorinated hydrocarbons such as methylene chloride, alcohols such as methanol, ethanol, n-propanol, n-pentanol, n-butanol, 3-methyl-1-butanol or n-hexanol and ethers such as dioxane, tetrahydrofuran and diethyl ethers. Methanol, ethanol or n-pentanol are particularly preferred.

The quantitative ratios of the starting materials are not critical; it is expedient to employ stoichiometric amounts of the starting compounds if an excess of one or the other component, eg. 10 mol %, is not recommended.

Normally, the reaction temperature is from 0° to 100° C., preferably from 20° to 80° C.

If, inter alia, the amides IV' are additionally employed as starting materials, the reaction should be carried out in the presence of the alcohol R—H.

One process variant consists in reacting the crude mixture obtained from the Pinner reaction with O-methylhydroxylamine or one of its acid addition salts without isolation from the reaction mixture.

Alternatively to this, it is also possible to react the ketoesters IV or the α-ketocarboxamides IV' or a mixture of the compounds IV and IV' with hydroxylamine or one of its acid addition products to give the oxime V and to subsequently treat this with a methylating agent, if appropriate in the presence of a base and of a suitable solvent.

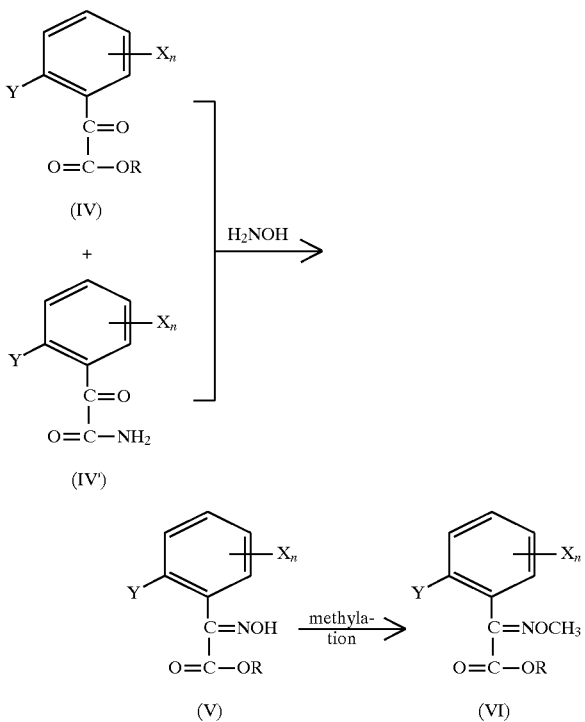

The hydroxylamine is in this case employed either in the form of an acid addition salt or as a free base, it being possible to liberate the unprotonated compound from the salt by addition of a strong base. Suitable salts of hydroxylamine are the salts with mono- to tribasic acids, such as, in particular, hydrochloric acid and sulfuric acid. The use of acid addition salts is preferred.

Oxime formation is carried out, for example, in the presence of a solvent or diluent. Suitable solvents are preferably aromatic hydrocarbons such as benzene, toluene and o-, m- or p-xylene, chlorinated hydrocarbons such as methylene chloride, alcohols such as methanol, ethanol, n-propanol, n-pentanol, n-butanol, 3-methyl-1-butanol and n-hexanol. Methanol, ethanol or n-pentanol is particularly preferred.

The quantitative ratios of the starting materials are not critical; it is expedient to employ stoichiometric amounts of starting compounds if an excess of one or the other component, eg. 10 mol %, is not recommended.

Normally, the reaction temperature is from 0° to 100° C., preferably from 20° to 80° C. If the amides IV' are additionally employed as starting materials, the reaction must be carried out in the presence of the alcohol R—OH. One process variant consists in reacting the crude mixture obtained from the Pinner reaction with hydroxylamine or one of its acid addition products without isolation from the reaction mixture.

Methylation is carried out, for example, by converting the oximes V to the corresponding salt using a base in the presence of a diluent and reacting this salt with a methylating agent. In this case, the oximate can be isolated before reaction with the methylating agent or else also directly reacted further.

Preferred bases are potassium hydroxide, sodium hydroxide, potassium carbonate, sodium carbonate, sodium methoxide, sodium ethoxide, sodium n-pentoxide and potassium tert-butoxide.

Suitable methylating agents are methyl halides, in particular methyl chloride or else dimethyl sulfate.

Organic diluents which can be used both for oximate formation and for methylation are solvents, such as, for example, acetone, dioxane, tetrahydrofuran, alcohols such as methanol, ethanol, n-propanol or n-pentanol; sulfoxides such as dimethyl sulfoxide, diethyl sulfoxide, dimethyl sulfone, diethyl sulfone, methyl ethyl sulfone, tetramethylene sulfone; nitriles such as acetonitrile, benzonitrile, butyronitrile, isobutyronitrile, m-chlorobenzonitrile; N,N-disubstituted carboxamides such as dimethylformamide, tetramethylurea, N,N-dimethylbenzamide, N,N-dimethylacetamide, N,N-dimethylphenylacetamide, N,N-dimethylcyclohexanecarboxamide, N,N-dimethylpropionamide and homologous carboxylic acid piperidide, carboxylic acid morpholide or carboxylic acid pyrrolidide; corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl or N-ethyl-N-tert-butyl compounds, N-methylformanilide, N-ethylpyrrolidone, N-butylpyrrolidone, N-ethyl-6-piperidone, N-methylpyrrolidone; hexamethylphosphoramide; and appropriate mixtures. Dimethylacetamide, N-methylpyrrolidone, dimethylformamide, dimethyl sulfoxide and tetramethylene sulfone are preferred. N-methylpyrrolidone and dimethylformamide are particularly preferred.

Conversion of the oximes V to their anions and subsequent methylation is generally carried out at from −20° to 100° C., preferably from 0° to 80° C., in particular at from 20° to 80° C.

The oxime V, the base and the alkylating agent are employed in a stoichiometric amount or an excess of the base and the alkylating agent, preferably from 1.05 to 1.5 mol of alkylating agent and from 1 to 1.5 mol of base, is used per mole of oxime V.

One process variant consists in further reacting the oxime salt without removal of the diluent.

As a rule, the oxime ethers VI are obtained as isomer mixtures, the oxime bond (C=NOCH$_3$) being present partly in the E and partly in the Z configuration. A rearrangement of the oxime ethers to the E configuration is possible if desired by treatment of the isomer mixture of VI with a catalyst, preferably an acid, in an organic diluent.

Suitable solvents are preferably acetone, aromatic hydrocarbons such as benzene, toluene and o-, m- or p-xylene, chlorinated hydrocarbons such as methylene chloride, alcohols such as methanol, ethanol, n-propanol, n-butanol, n-pentanol, 3-methyl-1-butanol and n-hexanol, ethers such as diethyl ether, dioxane, tetrahydrofuran, tert-butyl methyl ether and diisopropyl ether, sulfoxides such as dimethyl sulfoxide, diethyl sulfoxide, dimethyl sulfone, diethyl sulfone, methyl ethyl sulfone, tetramethylene sulfone; nitriles such as acetonitrile, benzonitrile, butyronitrile, isobutyronitrile, m-chlorobenzonitrile; N,N-disubstituted carboxamides such as dimethylformamide, tetramethylurea, N,N-dimethylbenzamide, N,N-dimethylacetamide, N,N-dimethylphenylacetamide, N,N-dimethylcyclohexanecarboxamide, N,N-dimethylpropionamide and homologous carboxylic acid piperidide, carboxylic acid morpholide or carboxylic acid pyrrolidide; corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl and N-ethyl-N-tert-butyl compounds, N-methylformanilide, N-ethylpyrrolidone, N-butylpyrrolidone, N-ethyl-6-piperidone, N-methylpyrrolidone; hexamethylphosphoramide; and appropriate mixtures and also mixtures with water.

Methanol, ethanol, n-pentanol, toluene and diethyl ether are particularly preferred.

Suitable acids are particularly mineral acids, for example perchloric acid, sulfuric acid, phosphoric acid and hydrohalic acids such as hydrochloric acid, aliphatic sulfonic acids such as trifluoromethanesulfonic acid, aromatic sulfonic acids such as p-toluenesulfonic acid, and halogenated alkanecarboxylic acids such as trifluoroacetic acid. Hydrogen chloride gas is particularly preferred.

A from 0.01-fold to 10-fold, in particular a from 0.01- to 5-fold, molar amount of acid is customarily used, based on the amount of the isomer mixture VI.

The reaction temperature for the isomerization is generally from −20° to 100° C., in particular from 0° to 80° C.

The rearrangement of the oxime ethers requires a certain time, mainly depending on the temperature and in particular the amount of acid, for example from 1 to 90 hours, preferably from 2 to 10 hours.

The crude solution after the formation of the oxime ethers VI can be initially concentrated or further diluted before the possible isomerization step. One preferred variant consists in treating the crude solution obtained after oxime ether formation but without further concentration or dilution directly with the acid.

The oxime ethers VI thus obtained can then be converted with methylamine to the corresponding α-methoxyiminocarboxylic acid methylamides I.

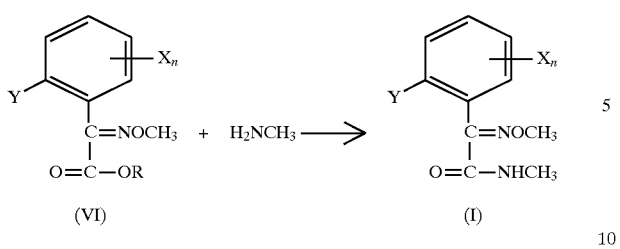

The reaction is carried out in a manner known per se in an inert organic solvent at from 0° C. to 100° C., preferably from 10° C. to 70° C.

In particular, the solvents used are acetonitrile, tetrahydrofuran, dioxane, methanol, ethanol, n-pentanol, N-methylpyrrolidone, dimethylformamide, dimethylacetamide and dimethyl sulfoxide.

Methylamine is customarily used in an excess, the methylamine being passed into the reaction mixture either as a gas or the reaction mixture being treated with an aqueous or alcoholic methylamine solution.

In the case where the amides I are formed during preparation in the form of isomer mixtures with respect to the double bond of the group $C=NOCH_3$, these can be converted, if desired, into the corresponding E isomers by treatment with acids according to the process described with respect to the oxime ethers VI.

The process according to the invention is additionally suitable for preparing methyl α-methoxyiminocarboxylates of the formula I'

if the oxime ethers of the formula VI are transesterified in a manner known per se (Houben-Weyl, Vol. E5, p. 702–707; Tetrahedron 42 (1986), 6719).

In general, the transesterification is carried out as follows:

The crude product is taken up in an excess of methanol and subjected to a transesterification in a known manner, either by addition of mineral acids or by addition of bases (eg. sodium methoxide).

The process according to the invention is additionally particularly suitable for the preparation of α-methoxyiminocarboxylic acid methylamides of the formula IA

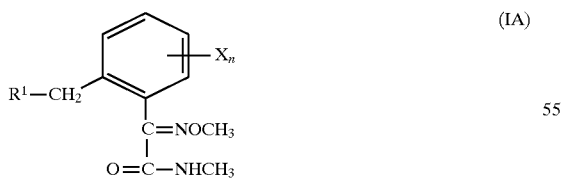

where the substituents and the index have the following meanings:

X is nitro, trifluoromethyl, halogen, $C_1$–$C_4$-alkyl or $C_1$–$C_4$-alkoxy, n is 0 or an integer of from 1 to 4, where the X radicals can be different if n>1, $R^1$ is hydrogen, hydroxyl, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl or unsubstituted or substituted hetaryloxy,

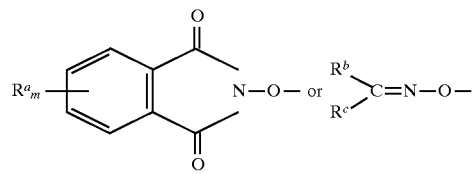

$R^a$ is cyano, nitro, halogen, $C_1$–$C_4$-alkyl, $C_1$–$C_4$-haloalkyl, $C_1$–$C_4$-alkoxy or $C_1$–$C_4$-haloalkoxy, m is 0 or an integer of from 1 to 4, where the $R^a$ radicals can be different if m>1, $R^b$ is hydrogen, unsubstituted or substituted alkyl, cycloalkyl, alkenyl, cycloalkenyl, alkynyl, heterocyclyl, alkylcarbonyl, cycloalkylcarbonyl, alkenylcarbonyl, alkynylcarbonyl, heterocyclylcarbonyl, alkoxycarbonyl, aryl, hetaryl, arylcarbonyl, hetarylcarbonyl, arylsulfonyl, hetarylsulfonyl or a C(R')=NOR" group;

R' is hydrogen, hydroxyl, cyano, nitro, amino, halogen, unsubstituted or substituted alkyl, alkoxy, alkylthio, alkylamino, dialkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, cycloalkenyl, cycloalkenyloxy, cycloalkenylthio, cycloalkenylamino, heterocyclyl, heterocyclyloxy, heterocyclylthio, heterocyclylamino, aryl, aryloxy, arylthio, arylamino, heteroaryl, heteroaryloxy, heteroarylthio or heteroarylamino;

R' is hydrogen, unsubstituted or substituted alkyl, cycloalkyl, alkenyl, alkynyl, heterocyclyl, aryl or heteroaryl, $R^c$ is a group mentioned under $R^b$ or hydroxyl, cyano, nitro, amino, halogen, unsubstituted or substituted alkoxy, alkylthio, alkylamino, dialkylamino, aryloxy, arylthio, arylamino, hetaryloxy, hetarylthio or hetarylamino;

or $R^b$ and $R^c$, together with the C atom to which they are bonded, are a carbocyclic or heterocyclic ring.

Compounds of this type are known from the literature cited at the outset as active compounds for controlling harmful fungi.

The process according to the invention is additionally suitable for preparing methyl α-methoxyiminocarboxylates of the formula I'A

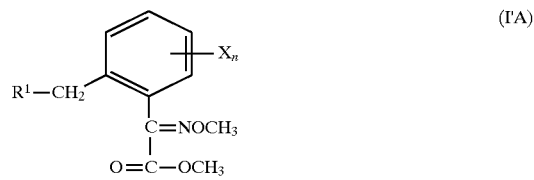

where the substituents and the index have the meanings given above for the compounds IA. Compounds of this type are disclosed, for example, in EP-A 253 213, EP-A 254 426, EP-A 363 818, EP-A 378 308, EP-A 385 224, EP-A 386 561, EP-A 400 417, EP-A 407 873, EP-A 460 575, EP-A 463 488, EP-A 472 300, WO-A 94/00,436 and DE Appl. No. 44 21 180.5 for controlling harmful fungi.

Accordingly, compounds of the formula IIA

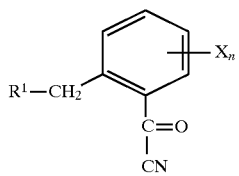
(IIA)

are particularly preferred as starting substances.

For the preparation of the active compounds disclosed in the literature, it is insignificant whether those substances where $R^1$ is hydrogen, hydroxyl, mercapto, cyano, nitro, unsubstituted or substituted alkylsulfonyloxy, unsubstituted or substituted arylsulfonyloxy or halogen are employed as compounds IIA, or those where $R^1$ is unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl or unsubstituted or substituted hetaryloxy, a hydroxyphthalimido radical

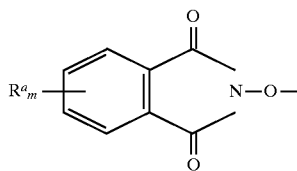

or an oxyimino radical

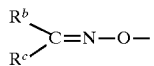

The radicals $R^1$ mentioned in the first group may preferably be converted to the substituents of the second group in stages IV and V, and in particular in stages VI and I, according to the processes described in the literature mentioned. The relevant data of the cited specifications are hereby included.

In the definitions of the symbols given in the above formulae, collective terms were used which are generally representative of the following substituents:

Halogen: fluorine, chlorine, bromine and iodine;

Alkyl: saturated, straight-chain or branched hydrocarbon radicals having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylcarbonyl: straight-chain or branched alkyl groups having 1 to 10 carbon atoms (as mentioned above), which are bonded to the structure via a carbonyl group (—CO—);

Alkylsulfonyloxy: straight-chain or branched alkyl groups having 1 to 10 carbon atoms (as mentioned above), which are bonded to the structure via a sulfonyloxy group (—$SO_2$—O—);

Haloalkyl: straight-chain or branched alkyl groups having 1 to 4 carbon atoms (as mentioned above), it being possible for the hydrogen atoms in these groups to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 or 10 carbon atoms (as mentioned above), which are bonded to the structure via an oxygen atom (—O—);

Alkoxycarbonyl: straight-chain or branched alkoxy groups having 1 to 10 carbon atoms (as mentioned above), which are bonded to the structure via a carbonyl group (—CO—);

Haloalkoxy: straight-chain or branched haloalkyl groups having 1 to 4 carbon atoms (as mentioned above), which are bonded to the structure via an oxygen atom (—O—);

Alkylthio: straight-chain or branched alkyl groups having 1 to 10 carbon atoms (as mentioned above), which are bonded to the structure via a sulfur atom (—S—);

Alkylamino: a straight-chain or branched alkyl group having 1 to 4 carbon atoms (as mentioned above), which is bonded to the structure via an amino group (—NH—);

Dialkylamino: two straight-chain or branched alkyl groups having 1 to 4 carbon atoms (as mentioned above), which are independent of one another and are bonded to the structure via a nitrogen atom (—N:);

Alkenyl: unsaturated, straight-chain or branched hydrocarbon radicals having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-penyenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl- 2-butenyl, 2-ethyl-3-butenyl, 1,1,2-trimethyl-2-propenyl, 1-ethyl-1-methyl-2-propenyl, 1ethyl-2-methyl-1-propenyl and 1-ethyl-2-methyl-2-propenyl;

Alkenyloxy: an unsaturated, straight-chain or branched hydrocarbon group having 2 or 3 to 6 or 10 carbon atoms and a double bond in any desired position (as mentioned above), which is bonded to the structure via an oxygen atom (—O—);

Alkenylthio: an unsaturated, straight-chain or branched hydrocarbon group having 2 or 3 to 6 or 10 carbon atoms and a double bond in any desired position (as mentioned above), which is bonded to the structure via a sulfur atom (—S—);

Alkenylamino: an unsaturated, straight-chain or branched hydrocarbon group having 2 or 3 to 6 or 10 carbon atoms and a double bond in any desired position (as mentioned above), which is bonded to the structure via an amino group (—NH—);

Alkenylcarbonyl: unsaturated, straight-chain or branched hydrocarbon groups having 2 to 10 carbon atoms and a double bond in any desired position (as mentioned above), which are bonded to the structure via a carbonyl group (—CO—);

Alkynyl: straight-chain or branched hydrocarbon groups having 2 to 10 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Alkynyloxy: a straight-chain or branched hydrocarbon group having 2 or 3 to 6 or 10 carbon atoms and a triple bond in any desired position (as mentioned above), which is bonded to the structure via an oxygen atom (—O—);

Alkynylthio: a straight-chain or branched hydrocarbon group having 2 or 3 to 6 or 10 carbon atoms and a triple bond in any desired position (as mentioned above), which is bonded to the structure via a sulfur atom (—S—);

Alkynylamino: a straight-chain or branched hydrocarbon group having 2 or 3 to 6 or 10 carbon atoms and a triple bond in any desired position (as mentioned above), which is bonded to the structure via an amino group (—NH—);

Alkynylcarbonyl: straight-chain or branched hydrocarbon groups having 2 to 10 carbon atoms and a triple bond in any desired position (as mentioned above), which are bonded to the structure via a carbonyl group (—CO—);

Cycloalkyl: monocyclic alkyl groups having 3 to 12 carbon ring members, eg. $C_3$–$C_8$-cycloalkyl such as cyclopropyl, cyclobutyl, cyclopentyl, cyclohexyl, cycloheptyl and cyclooctyl;

Cycloalkoxy: a monocyclic alkyl group having 3 to 6, 8 or 12 carbon ring members (as mentioned above), which is bonded to the structure via an oxygen atom (—O—);

Cycloalkylthio: a monocyclic alkyl group having 3 to 6, 8 or 12 carbon ring members (as mentioned above), which is bonded to the structure via a sulfur atom (—S—);

Cycloalkylamino: a monocyclic alkyl group having 3 to 6, 8 or 12 carbon ring members (as mentioned above), which is bonded to the structure via an amino group (—NH—);

Cycloalkylcarbonyl: a monocyclic alkyl group having 3 to 6, 8 or 12 carbon ring members (as mentioned above), which is bonded to the structure via a carbonyl group (—CO—);

Cycloalkenyl: monocyclic hydrocarbons having 5 to 12 carbon ring members and one or two double bonds in the ring, eg. $C_3$–$C_8$-cycloalkenyl such as cyclopropenyl, cyclobutenyl, cyclopentyl, cyclohexenyl, cycloheptenyl, cyclooctenyl and cyclohexadienyl;

Cycloalkenyloxy: a monocyclic alkenyl group having 5 to 8 or 12 carbon ring members and one or two double bonds (as mentioned above), which is bonded to the structure via an oxygen atom (—O—);

Cycloalkenylthio: a monocyclic alkenyl group having 5 to 8 or 12 carbon ring members and one or two double bonds (as mentioned above), which is bonded to the structure via a sulfur atom (—S—);

Cycloalkenylamino: a monocyclic alkenyl group having 3 to 8 or 12 carbon ring members and one or two double bonds (as mentioned above), which is bonded to the structure via an amino group (—NH—);

Heterocyclyl: a saturated or partially unsaturated cyclic radical which, in addition to carbon atoms, contains as ring members heteroatoms from the group consisting of oxygen, sulfur and nitrogen: eg. 5- or 6-membered heterocycles (heterocyclyl) containing, in addition to carbon ring members, one to three nitrogen atoms and/or an oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4- dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, particularly preferably 1-pyrrolidinyl, 1-pyrazolidinyl, 1-imidazolidinyl, 2-isoxazolidinyl, 3-oxazolidinyl, 2-isothiazolidinyl, 3-thiazolidinyl, 2,3-dihydropyrrol-1-yl, 2,5-dihydropyrrol-1-yl, 2,3-dihydropyrazol-1-yl, 4,5-dihydropyrazol-1-yl, 2,3-dihydroimidazol-1-yl, 4,5-dihydroimidazol-1-yl, 2,3-dihydroisoxazol-2-yl, 2,3-dihydrooxazol-3-yl, 2,3-dihydroisothiazol-2-yl, 2,3-dihydrothiazol-3-yl, piperidin-1-yl, morpholin-1-yl and pyrazin-1-yl;

Heterocyclyloxy: a saturated or partially unsaturated cyclic radical which, in addition to carbon atoms, contains as ring members hetero atoms from the group consisting of oxygen, sulfur and nitrogen (as mentioned above), which is bonded to the structure via an oxygen atom (—O—);

Heterocyclylthio: a saturated or partially unsaturated cyclic radical which, in addition to carbon atoms, contains as ring members hetero atoms from the group consisting of oxygen, sulfur and nitrogen (as mentioned above), which is bonded to the structure via a sulfur atom (—S—);

Heterocyclylamino: a saturated or partially unsaturated cyclic radical which, in addition to carbon atoms, contains as ring members hetero atoms from the group consisting of oxygen, sulfur and nitrogen (as mentioned above), which is bonded to the structure via an amino group (—NH—);

Aryl or aryloxy, arylthio, arylamino, arylcarbonyl, arylsulfonyl and arylsulfonyloxy: aromatic mono- or polycyclic hydrocarbon radicals which are bonded to the structure directly or (aryloxy) via an oxygen atom (—O—) or (arylthio) a sulfur atom (—S—), (arylamino) an amino group (—NH—), (arylcarbonyl) via a carbonyl group (—CO—), (arylsulfonyl) via a sulfonyl group (—SO$_2$—) or (arylsulfonyloxy) via a sulfonyloxy group (—SO$_2$—O—), eg. phenyl, naphthyl and phenanthrenyl or phenoxy, naphthyloxy and phenanthrenyloxy and the corresponding thio-, carbonyl-, sulfonyl- and sulfonyloxy radicals;

Hetaryl or hetaryloxy, hetarylthio, hetarylamino, hetarylcarbonyl and hetarylsulfonyl: aromatic mono- or polycyclic radicals, which in addition to carbon ring members additionally can contain one to four nitrogen atoms or one to three nitrogen atoms and an oxygen or a sulfur atom or an oxygen or a sulfur atom and which are bonded to the structure directly or (hetaryloxy) via an oxygen atom (—O—) or (hetarylthio) a sulfur atom (—S—), (hetarylamino) an amino group (—NH—), (hetarylcarbonyl) via a carbonyl group (—CO—) or (hetarylsulfonyl) via a sulfonyl group (—SO$_2$—), eg. 5-membered heteroaryl, containing one to three nitrogen atoms: 5-membered ring heteroaryl groups, which in addition to carbon atoms can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl, containing one to four nitrogen atoms or one to three nitrogen atoms and a sulfur or oxygen atom or an oxygen or a sulfur atom: 5-membered ring heteroaryl groups, which in addition to carbon atoms can contain one to four nitrogen atoms or one to three nitrogen atoms and a sulfur or oxygen atom or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

fused 5-membered heteroaryl, containing one to four nitrogen atoms or one to three nitrogen atoms and/or an oxygen or sulfur atom: 5-membered ring heteroaryl groups, which in addition to carbon atoms can contain one to four nitrogen atoms or one to three nitrogen atoms and a sulfur or oxygen atom or an oxygen or a sulfur atom as ring members, and in which two adjacent carbon ring members or a nitrogen and an adjacent carbon ring member can be bridged to form an aromatic or heteroaromatic bicycle or polycycle, eg. benzofuranyl, isobenzofuranyl, benzothienyl, isobenzothienyl, indolyl, isoindolyl, benzoisoxazolyl, benzoxazolyl, benzoisothiazolyl, benzothiazolyl, indazolyl, benzimidazolyl, pyrrolopyridinyl, pyrrolopyridazinyl, pyrrolopyrimidinyl, pyrrolopyrazinyl, pyrrolotriazinyl, furopyridinyl, furopyridazinyl, furopyrimidyl, furopyrazinyl, furotriazinyl, thienopyridinyl, thienopyridazinyl, thienopyrimidyl, thienopyrazinyl, thienotriazinyl, imidazopyridinyl, imidazopyridazinyl, imidazopyrimidyl, imidazopyrazinyl, imidazotriazinyl, pyrazolopyridinyl, pyrazolopyridazinyl, pyrazolopyrimidyl, pyrazolopyrazinyl, pyrazolotriazinyl, isoxazolopyridinyl, isoxazolopyridazinyl, isoxazolopyrimidyl, isoxazolopyrazinyl, isoxazolotriazinyl, oxazolopyridinyl, oxazolopyridazinyl, oxazolopyrimidyl, oxazolopyrazinyl, oxazolotriazinyl, isothiazolopyridinyl, isothiazolopyridazinyl, isothiazolopyrimidyl, isothiazolopyrazinyl, isothiazolotriazinyl, thiazolopyridinyl, thiazolopyridazinyl, thiazolopyrimidyl, thiazolopyrazinyl, thiazolotriazinyl, triazolopyridinyl, triazolopyridazinyl, triazolopyrimidyl, triazolopyrazinyl and triazolotriazinyl;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups, which in addition to carbon atoms can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members eg. 1-pyrrolyl, 1-imidazolyl, 1-pyrazolyl and 1,2,4-triazol-1-yl;

6-membered heteroaryl, containing one to three or one to four nitrogen atoms: 6-membered ring heteroaryl groups, which in addition to carbon atoms can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

fused 6-membered heteroaryl, containing one to four nitrogen atoms: 6-membered ring heteroaryl groups in which two adjacent carbon ring members can be bridged to form an aromatic or heteroaromatic biocycle or polycycle, eg. quinoline, isoquinoline, quinazoline and quinoxaline, or the corresponding oxy, thio, carbonyl or sulfonyl groups.

The addition of unsubstituted or substituted with reference to alkyl, alkylcarbonyl, alkylsulfonyl, alkoxy, alkoxycarbonyl, alkylthio, alkylamino, dialkylamino, alkenyl, alkenyloxy, alkenylthio, alkenylamino, alkenylcarbonyl, alkynyl, alkynyloxy, alkynylthio, alkynylamino and alkynylcarbonyl groups is intended to express that these groups can be partly or completely halogenated and/or can carry one to three, preferably one, of the following radicals: cyano, nitro, hydroxyl, mercapto, amino, carboxyl, aminocarbonyl, aminothiocarbonyl, halogen, $C_1$–$C_6$-alkoxy, $C_1$–$C_6$-haloalkoxy, $C_1$–$C_6$-alkoxycarbonyl, $C_3$–$C_6$-cycloalkyl, $C_1$–$C_6$-alkylamino (an NH group which carries one alkyl group as mentioned above), di-$C_1$–$C_6$-alkylamino (an amino group which carries two alkyl groups as mentioned above, which are independent of one another), aryl, aryloxy, hetaryl or hetaryloxy, arylthio or hetarylthio, it being possible for the last-mentioned aromatic or heteroaromatic groups in turn to be partly or completely halogenated and/or to carry one to three of the following groups: cyano, nitro, hydroxyl, amino, carboxyl, aminocarbonyl, aminothiocarbonyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino and $C_1$–$C_4$-alkoxycarbonyl.

The addition of unsubstituted or substituted to the cycloalkyl, cycloalkenyl, heterocyclyl, aryl- and hetaryl groups mentioned (or the corresponding oxy, thio, carbonyl, sulfonyl and sulfonyloxy groups) is intended to express that these groups can be partly or completely halogenated and/or can carry one to four, preferably one or two, of the following radicals: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkoxy, $C_1$–$C_6$-haloalkoxy, $C_1$–$C_6$-alkoxycarbonyl, $C_1$–$C_6$-alkylthio, $C_3$–$C_6$-cycloalky, C–C6-alkylamino (an NH group which carries an alkyl group as mentioned above), di-$C_1$–$C_6$-alkylamino (an amino group which carries two alkyl groups as mentioned above, which are independent of one another), $C_1$–$C_6$-alkylsulfonyl, $C_2$–$C_6$-alkenyl, $C_2$–$C_6$-alkenyloxy, aryl, aryl-$C_1$–$C_4$-alkyl, aryloxycarbonyl, aryloxy, hetaryl, hetaryloxy or 1-($C_1$–$C_6$-alkoxyimino)-$C_1$–$C_6$-alkyl, where the aromatic and heteroaromatic groups can be partially or completely halogenated and/or can carry one to three of the following groups: cyano, nitro, hydroxyl, amino, carboxyl, aminocarbonyl, aminothiocarbonyl, $C_1$–$C_4$-alkyl, $C_1$–$C_4$-haloalkyl, $C_1$–$C_4$-alkylcarbonyl, $C_1$–$C_4$-alkoxy, $C_1C_4$-haloalkoxy, $C_1$–$C_4$-alkoxycarbonyl, $C_1$–$C_4$-alkylthio, $C_1$–$C_4$-alkylamino and di-$C_2$–$C_4$-alkylamino.

The statement partly or completely halogenated is intended to express that in the groups characterized in this way the hydrogen atoms bonded to C atoms can be partly or completely replaced by identical or different halogen atoms as mentioned above, in particular fluorine, chlorine and/or bromine.

of particular importance are intermediates of the formulae IVA, IV'A, VA and VIA, where $R^1$ is hydrogen.

In addition, intermediates of the formulae IVA, IV'A, VA and VIA are preferred are preferred where $R^1$ is hydroxyl.

In particular, intermediates of the formulae IVA, IV'A, VA and VIA are preferred where RI is halogen (chlorine and bromine).

These compounds allow easy access to all types of active compounds described in the prior literature.

Representatives of the particularly preferred intermediates are compiled in the following Tables.

Table 1

Compounds of the formulae IVA, VA and VIA, where $X_n$ is hydrogen, R is $CH_2CH_2CH_3$ and $R^1$ corresponds to a compound of one of the groups compiled in Table A in each case Table 2

Compounds of the formulae IVA, VA and VIA, where $X_n$ is hydrogen, R is $(CH_2)_3CH_3$ and $R^1$ corresponds to a compound of one of the groups compiled in Table A in each case Table 3

Compounds of the formulae IVA, VA and VIA, where $X_n$ is hydrogen, R is $CH_2CH(CH_3)_2$ and $R^1$ corresponds to a compound of one of the groups compiled in Table A in each case Table 4

Compounds of the formulae IVA, VA and VIA, where $X_n$ is hydrogen, R is $CH(CH_3)CH_2CH_3$ and $R^1$ corresponds to a compound of one of the groups compiled in Table A in each case Table 5

Compounds of the formulae IVA, VA and VIA, where $X_n$ is hydrogen, R is $(CH_2)_4CH_3$ and $R^1$ corresponds to a compound of one of the groups compiled in Table A in each case Table 6

Compounds of the formulae IVA, VA and VIA, where $X_n$ is hydrogen, R is $CH_2CH_2CH(CH_3)_2$ and $R^1$ corresponds to a compound of one of the groups compiled in Table A in each case Table 7

Compounds of the formulae IVA, VA and VIA, where $X_n$ is hydrogen, R is $CH_2C(CH_3)_3$ and $R^1$ corresponds to a compound of one of the groups compiled in Table A in each case Table 8

Compounds of the formulae IVA, VA and VIA, where $X_n$ is hydrogen, R is $C(CH_3)_2CH_2CH_3$ and $R^1$ corresponds to a compound of one of the groups compiled in Table A in each case Table 9

Compounds of the formulae IVA, VA and VIA, where $X_n$ is hydrogen, R is pent-2-yl and $R^1$ corresponds to a compound of one of the groups compiled in Table A in each case Table 10

Compounds of the formulae IVA, VA and VIA, where $X_n$ is hydrogen, R is pent-3-yl and $R^1$ corresponds to a compound of one of the groups compiled in Table A in each case Table 11
 Compounds of the formulae IVA, VA and VIA, where $X_n$ is hydrogen, R is 2-methylbut-1-yl and $R^1$ corresponds to a compound of one of the groups compiled in Table A in each case Table 12
 Compounds of the formulae IVA, VA and VIA, where $X_n$ is hydrogen, R is 3-methylbut-2-yl and $R^1$ corresponds to a compound of one of the groups compiled in Table A in each case Table 13
 Compounds of the formulae IVA, VA and VIA, where $X_n$ is hydrogen, R is $(CH_2)_5CH_3$ and $R^1$ corresponds to a compound of one of the groups compiled in Table A in each case Table 14
 Compounds of the formulae IVA, VA and VIA, where $X_n$ is hydrogen, R is 2-ethylhex-1-yl and $R^1$ corresponds to a compound of one of the groups compiled in Table A in each case Table 15
 Compounds of the formulae IVA, VA and VIA, where $X_n$ is hydrogen, R is $(CH_2)_6CH_3$ and $R^1$ corresponds to a compound of one of the groups compiled in Table A in each case Table 16
 Compounds of the formulae IVA, VA and VIA, where $X_n$ is hydrogen, R is $(CH_2)_7CH_3$ and $R^1$ corresponds to a compound of one of the groups compiled in Table A in each case Table 17
 Compounds of the formulae IVA, VA and VIA, where $X_n$ is hydrogen, R is 2-methoxyeth-1-yl and $R^1$ corresponds to a compound of one of the groups compiled in Table A in each case Table 18
 Compounds of the formulae IVA, VA and VIA, where $X_n$ is hydrogen, R is 2-ethoxyeth-1-yl and $R^1$ corresponds to a compound of one of the groups compiled in Table A in each case Table 19
 Compounds of the formulae IVA, VA and VIA, where $X_n$ is hydrogen, R is 2-chloroeth-1-yl and $R^1$ corresponds to a compound of one of the groups compiled in Table A in each case Table 20
 Compounds of the formulae IVA, VA and VIA, where $X_n$ is hydrogen, R is ethyl and $R^1$ corresponds to a compound of one of the groups compiled in Table A in each case Table 21
 Compounds of the formulae IVA, VA and VIA, where $X_n$ is hydrogen, R is 1-methylethyl and $R^1$ corresponds to a compound of one of the groups compiled in Table A in each case Table 22
 Compounds of the formula IV'A, where $X_n$ is hydrogen and $R^1$ corresponds to a compound of one of the groups compiled in Table A in each case

TABLE A

| $R^1$ |
|---|
| H |
| OH |
| Br |
| Cl |

TABLE A-continued

| |
|---|
| $CH_3SO_2O$ |
| $C_6H_5SO_2O$ |
| 4-$CH_3$—$C_6H_4SO_2O$ |
| $(CH_3)_2C=NO$ |
| $CH_3O-C(CH_3)=NO$ |
| $H_3CCH_2O-C(CH_3)=NO$ |
| 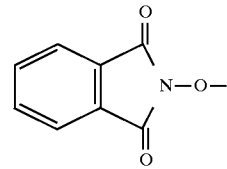 |
| 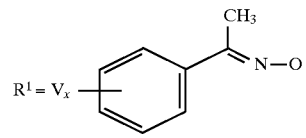 |
| $V_x$ |
| H |
| 2-F |
| 3-F |
| 4-F |
| 2,3-$F_2$ |
| 2,4-$F_2$ |
| 2,5-$F_2$ |
| 2,6-$F_2$ |
| 3,4-$F_2$ |
| 3,5-$F_2$ |
| 2-Cl |
| 3-Cl |
| 4-Cl |
| 2,3-$Cl_2$ |
| 2,4-$Cl_2$ |
| 2,5-$Cl_2$ |
| 2,6-$Cl_2$ |
| 3,4-$Cl_2$ |
| 3,5-$Cl_2$ |
| 2,3,4-$Cl_3$ |
| 2,3,5-$Cl_3$ |
| 2,4,4-$Cl_3$ |
| 3,4,5-$Cl_3$ |
| 2-Br |
| 3-Br |
| 4-Br |
| 2,3-$Br_2$ |
| 2,4-$Br_2$ |
| 2,5-$Br_2$ |
| 3,4-$Br_2$ |
| 3,5-$Br_2$ |
| 2-F, 3-Cl |
| 2-F, 4-Cl |
| 2-F, 5-Cl |
| 3-F, 4-Cl |
| 3-F, 5-Cl |
| 3-F, 6-Cl |
| 4-F, 5-Cl |
| 3-Cl, 4-Br |
| 3-Cl, 5-Br |
| 4-Cl, 5-Br |
| 2-$NO_2$ |
| 3-$NO_2$ |
| 4-$NO_2$ |
| 2-$CH_3$ |
| 3-$CH_3$ |
| 4-$CH_3$ |
| 2,3-$(CH_3)_2$ |
| 2,4-$(CH_3)_2$ |
| 2,5-$(CH_3)_2$ |
| 2,6-$(CH_3)_2$ |
| 3,4-$(CH_3)_2$ |
| 3,5-$(CH_3)_2$ |
| 2-$C_2H_5$ |

TABLE A-continued

3-C$_2$H$_5$
4-C$_2$H$_5$
2-(CH$_2$)$_2$CH$_3$
3-(CH$_2$)$_2$CH$_3$
4-(CH$_2$)$_2$CH$_3$
2-CH(CH$_3$)$_2$
3-CH(CH$_3$)$_2$
4-CH(CH$_3$)$_2$
2-C(CH$_3$)$_3$
3-C(CH$_3$)$_3$
4-C(CH$_3$)$_3$
3-C$_6$H$_5$
4-C$_6$H$_5$
3-CH$_3$, 4-CH(CH$_3$)$_2$
3,5-[C(CH$_3$)$_3$]$_2$, 4-CH$_3$
2-OH
3-OH
4-OH
2-OCH$_3$
3-OCH$_3$
4-OCH$_3$
2-OC$_2$H$_5$
3-OC$_2$H$_5$
4-OC$_2$H$_5$
2-O(CH$_2$)$_2$CH$_3$
3-O(CH$_2$)$_2$CH$_3$
4-O(CH$_2$)$_2$CH$_3$
2-OCH(CH$_3$)$_2$
3-OCH(CH$_3$)$_2$
4-OCH(CH$_3$)$_2$
2-OC(CH$_3$)$_3$
3-OC(CH$_3$)$_3$
4-OC(CH$_3$)$_3$
2-OC$_6$H$_5$
3-OC$_6$H$_5$
4-OC$_6$H$_5$
2-CF$_3$
3-CF$_3$
4-CF$_3$
2-CH$_2$CH$_2$F
3-CH$_2$CH$_2$F
4-CH$_2$CH$_2$F
2-CH$_2$CF$_3$
3-CH$_2$CF$_3$
4-CH$_2$CF$_3$
2-C$_2$F$_5$
3-C$_2$F$_5$
4-C$_2$F$_5$
2-CF$_2$CHF$_2$
3-CF$_2$CHF$_2$
4-CF$_2$CHF$_2$
2-OCF$_3$
3-OCF$_3$
4-OCF$_3$
2-COCH$_3$
3-COCH$_3$
4-COCH$_3$
2-CO$_2$CH$_3$
3-CO$_2$CH$_3$
4-CO$_2$CH$_3$
2-CO$_2$C$_2$H$_5$
3-CO$_2$C$_2$H$_5$
4-CO$_2$C$_2$H$_5$
2-CN
3-CN
4-CN
2-NH$_2$
3-NH$_2$
4-NH$_2$
2-N(CH$_3$)$_2$
3-N(CH$_3$)$_2$
4-N(CH$_3$)$_2$
2-SCH$_3$
3-SCH$_3$
4-SCH$_3$
2-SO$_2$CH$_3$
3-SO$_2$CH$_3$
4-SO$_2$CH$_3$
3-Cl, 4-C(CH$_3$)$_3$

TABLE A-continued

3-F, 4-CH$_3$
3-F, 5-CH$_3$
4-F, 3-CH$_3$
4-Cl, 3-NO$_2$
3-Cl, 4-OCH$_3$
4-Cl, 3-OCH$_3$
3-Cl, 4-CF$_3$
4-Cl, 3-CF$_3$
3-CH$_3$, 4-OCH$_3$
4-CH$_3$, 3-OCH$_3$

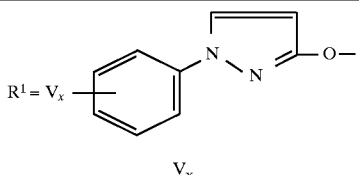

$R^1 = V_x$

| $V_x$ |
|---|
| H |
| 2-Cl |
| 3-Cl |
| 4-Cl |
| 2,3-Cl$_2$ |
| 2,4-Cl$_2$ |
| 2,5-Cl$_2$ |
| 2,6-Cl$_2$ |
| 3,5-Cl$_2$ |
| 2-CH$_3$ |
| 3-CH$_3$ |
| 4-CH$_3$ |
| 2,3-(CH$_3$)$_2$ |
| 2,4-(CH$_3$)$_2$ |
| 2,5-(CH$_3$)$_2$ |
| 2,6-(CH$_3$)$_2$ |
| 3,4-(CH$_3$)$_2$ |
| 3,5-(CH$_3$)$_2$ |
| 2-NO$_2$ |
| 3-NO$_2$ |
| 4-NO$_2$ |
| 2-CN |
| 3-CN |
| 4-CN |
| 2-OCH$_3$ |
| 3-OCH$_3$ |
| 4-OCH$_3$ |
| 2-CF$_3$ |
| 3-CF$_3$ |
| 4-CF$_3$ |
| 2-F |
| 3-F |
| 4-F |
| 2,3-F$_2$ |
| 2,4-F$_2$ |
| 2,5-F$_2$ |
| 2,6-F$_2$ |
| 3,4-F$_2$ |
| 3,5-F$_2$ |
| 3,4-Cl$_2$ |
| 2,3,4-Cl$_3$ |
| 2,3,5-Cl$_3$ |
| 2,3,6-Cl$_3$ |
| 2,4,5-Cl$_3$ |
| 2,4,6-Cl$_3$ |
| 3,4,5-Cl$_3$ |
| 2-Br |
| 3-Br |
| 4-Br |
| 2,3-Br$_2$ |
| 2,4-Br$_2$ |
| 2,5-Br$_2$ |
| 2,6-Br$_2$ |
| 3,4-Br$_2$ |
| 3,5-Br$_2$ |
| 2-I |
| 3-I |
| 4-I |

TABLE A-continued

| |
|---|
| 2,4-I₂ |
| 2-F, 3-Cl |
| 2-F, 4-Cl |
| 2-F, 5-Cl |
| 2-F, 6-Cl |
| 3-F, 2-Cl |
| 3-F, 4-Cl |
| 3-F, 5-Cl |
| 3-F, 6-Cl |
| 4-F, 2-Cl |
| 4-F, 3-Cl |
| 2-F, 3-Br |
| 2-F, 4-Br |
| 2-F, 5-Br |
| 2-F, 6-Br |
| 3-F, 2-Br |
| 3-F, 4-Br |
| 3-F, 5-Br |
| 3-F, 6-Br |
| 4-F, 2-Br |
| 4-F, 3-Br |
| 2-Br, 3-Cl |
| 2-Br, 4-Cl |
| 2-Br, 5-Cl |
| 2-Br, 6-Cl |
| 3-Br, 2-Cl |
| 3-Br, 4-Cl |
| 3-Br, 5-Cl |
| 3-Br, 6-Cl |
| 4-Br, 2-Cl |
| 4-Br, 3-Cl |
| 2-Cl, 3-CN |
| 2-Cl, 4-CN |
| 2-Cl, 5-CN |
| 2-Cl, 6-CN |
| 3-Cl, 2-CN |
| 3-Cl, 4-CN |
| 3-Cl, 5-CN |
| 3-Cl, 6-CN |
| 4-Cl, 2-CN |
| 4-Cl, 3-CN |
| 2-F, 3-CN |
| 2-F, 4-CN |
| 2-F, 5-CN |
| 2-F, 6-CN |
| 3-F, 2-CN |
| 3-F, 4-CN |
| 3-F, 5-CN |
| 3-F, 6-CN |
| 4-F, 2-CN |
| 4-F, 3-CN |
| 2-Cl, 3-CH₃ |
| 2-Cl, 4-CH₃ |
| 2-Cl, 5-CH₃ |
| 2-Cl, 6-CH₃ |
| 3-Cl, 2-CH₃ |
| 3-Cl, 4-CH₃ |
| 3-Cl, 5-CH₃ |
| 3-Cl, 6-CH₃ |
| 4-Cl, 2-CH₃ |
| 4-Cl, 3-CH₃ |
| 2-F, 3-CH₃ |
| 2-F, 4-CH₃ |
| 2-F, 5-CH₃ |
| 2-F, 6-CH₃ |
| 3-F, 4-CH₃ |
| 3-F, 5-CH₃ |
| 3-F, 6-CH₃ |
| 4-F, 2-CH₃ |
| 4-F, 3-CH₃ |
| 2-CN, 3-CH₃ |
| 2-CN, 4-CH₃ |
| 2-CN, 5-CH₃ |
| 2-CN, 6-CH₃ |
| 3-CN, 2-CH₃ |
| 3-CN, 4-CH₃ |
| 3-CN, 5-CH₃ |
| 3-CN, 6-CH₃ |
| 4-CN, 2-CH₃ |

TABLE A-continued

| |
|---|
| 4-CN, 3-CH₃ |
| 2-Cl, 3-CF₃ |
| 2-Cl, 4-CF₃ |
| 2-Cl, 5-CF₃ |
| 2-Cl, 6-CF₃ |
| 3-Cl, 2-CF₃ |
| 3-Cl, 4-CF₃ |
| 3-Cl, 5-CF₃ |
| 3-Cl, 6-CF₃ |
| 4-Cl, 2-CF₃ |
| 4-Cl, 3-CF₃ |
| 2-F, 3-CF₃ |
| 2-F, 4-CF₃ |
| 2-F, 5-CF₃ |
| 2-F, 6-CF₃ |
| 3-F, 2-CF₃ |
| 3-F, 4-CF₃ |
| 3-F, 5-CF₃ |
| 3-F, 6-CF₃ |
| 4-F, 2-CF₃ |
| 4-F, 3-CF₃ |
| 2-Cl, 3-OCH₃ |
| 2-Cl, 4-OCH₃ |
| 2-Cl, 5-OCH₃ |
| 2-Cl, 6-OCH₃ |
| 3-Cl, 2-OCH₃ |
| 3-Cl, 4-OCH₃ |
| 3-Cl, 5-OCH₃ |
| 3-Cl, 6-OCH₃ |
| 4-Cl, 2-OCH₃ |
| 4-Cl, 3-OCH₃ |
| 2-F, 3-OCH₃ |
| 2-F, 4-OCH₃ |
| 2-F, 5-OCH₃ |
| 2-F, 6-OCH₃ |
| 3-F, 2-OCH₃ |
| 3-F, 4-OCH₃ |
| 3-F, 5-OCH₃ |
| 3-F, 6-OCH₃ |
| 4-F, 2-OCH₃ |
| 4-F, 3-OCH₃ |
| 2-CN, 3-OCH₃ |
| 2-CN, 4-OCH₃ |
| 2-CN, 5-OCH₃ |
| 2-CN, 6-OCH₃ |
| 3-CN, 2-OCH₃ |
| 3-CN, 4-OCH₃ |
| 3-CN, 5-OCH₃ |
| 3-CN, 6-OCH₃ |
| 4-CN, 2-OCH₃ |
| 4-CN, 3-OCH₃ |
| 2-CH₃, 3-OCH₃ |
| 2-CH₃, 4-OCH₃ |
| 2-CH₃, 5-OCH₃ |
| 2-CH₃, 6-OCH₃ |
| 3-CH₃, 2-OCH₃ |
| 3-CH₃, 4-OCH₃ |
| 3-CH₃, 5-OCH₃ |
| 3-CH₃, 6-OCH₃ |
| 4-CH₃, 2-OCH₃ |
| 4-CH₃, 3-OCH₃ |
| 2-CF₃, 3-OCH₃ |
| 2-CF₃, 4-OCH₃ |
| 2-CF₃, 5-OCH₃ |
| 2-CF₃, 6-OCH₃ |
| 3-CF₃, 2-OCH₃ |
| 3-CF₃, 4-OCH₃ |
| 3-CF₃, 5-OCH₃ |
| 3-CF₃, 6-OCH₃ |
| 4-CF₃, 2-OCH₃ |
| 4-CF₃, 3-OCH₃ |
| 2-Cl, 3-OCF₃ |
| 2-Cl, 4-OCF₃ |
| 2-Cl, 5-OCF₃ |
| 2-Cl, 6-OCF₃ |
| 3-Cl, 2-OCF₃ |
| 3-Cl, 4-OCF₃ |
| 3-Cl, 5-OCF₃ |
| 3-Cl, 6-OCF₃ |

TABLE A-continued

4-Cl, 2-OCF$_3$
4-Cl, 3-OCF$_3$
2-F, 3-OCF$_3$
2-F, 4-OCF$_3$
2-F, 5-OCF$_3$
2-F, 6-OCF$_3$
3-F, 2-OCF$_3$
3-F, 4-OCF$_3$
3-F, 5-OCF$_3$
3-F, 6-OCF$_3$
4-F, 2-OCF$_3$
4-F, 3-OCF$_3$
2-CN, 3-OCF$_3$
2-CN, 4-OCF$_3$
2-CN, 5-OCF$_3$
2-CN, 6-OCF$_3$
3-CN, 2-OCF$_3$
3-CN, 4-OCF$_3$
3-CN, 5-OCF$_3$
3-CN, 6-OCF$_3$
4-CN, 2-OCF$_3$
4-CN, 3-OCF$_3$
2-CH$_3$, 3-OCF$_3$
2-CH$_3$, 4-OCF$_3$
2-CH$_3$, 5-OCF$_3$
2-CH$_3$, 6-OCF$_3$
3-CH$_3$, 2-OCF$_3$
3-CH$_3$, 4-OCF$_3$
3-CH$_3$, 5-OCF$_3$
3-CH$_3$, 6-OCF$_3$
4-CH$_3$, 2-OCF$_3$
4-CH$_3$, 3-OCF$_3$
2-CF$_3$, 3-OCF$_3$
2-CF$_3$, 4-OCF$_3$
2-CF$_3$, 5-OCF$_3$
2-CF$_3$, 6-OCF$_3$
3-CF$_3$, 2-OCF$_3$
3-CF$_3$, 4-OCF$_3$
3-CF$_3$, 5-OCF$_3$
3-CF$_3$, 6-OCF$_3$
4-CF$_3$, 2-OCF$_3$
4-CF$_3$, 3-OCF$_3$
2-Cl, 3-OCHF$_2$
2-Cl, 4-OCHF$_2$
2-Cl, 5-OCHF$_2$
2-Cl, 6-OCHF$_2$
3-Cl, 2-OCHF$_2$
3-Cl, 4-OCHF$_2$
3-Cl, 5-OCHF$_2$
3-Cl, 6-OCHF$_2$
4-Cl, 2-OCHF$_2$
4-Cl, 3-OCHF$_2$
2-F, 3-OCHF$_2$
2-F, 4-OCHF$_2$
2-F, 5-OCHF$_2$
2-F, 6-OCHF$_2$
3-F, 2-OCHF$_2$
3-F, 4-OCHF$_2$
3-F, 5-OCHF$_2$
3-F, 6-OCHF$_2$
4-F, 2-OCHF$_2$
4-F, 3-OCHF$_2$
2-CN, 3-OCHF$_2$
2-CN, 4-OCHF$_2$
2-CN, 5-OCHF$_2$
2-CN, 6-OCHF$_2$
3-CN, 2-OCHF$_2$
3-CN, 4-OCHF$_2$
3-CN, 5-OCHF$_2$
3-CN, 6-OCHF$_2$
4-CN, 2-OCHF$_2$
4-CN, 3-OCHF$_2$
2-CH$_3$, 3-OCHF$_2$
2-CH$_3$, 4-OCHF$_2$
2-CH$_3$, 5-OCHF$_2$
2-CH$_3$, 6-OCHF$_2$
3-CH$_3$, 2-OCHF$_2$
3-CH$_3$, 4-OCHF$_2$
3-CH$_3$, 5-OCHF$_2$

3-CH$_3$, 6-OCHF$_2$
4-CH$_3$, 2-OCHF$_2$
4-CH$_3$, 3-OCHF$_2$
2-CF$_3$, 3-OCHF$_2$
2-CF$_3$, 4-OCHF$_2$
2-CF$_3$, 5-OCHF$_2$
2-CF$_3$, 6-OCHF$_2$
3-CF$_3$, 2-OCHF$_2$
3-CF$_3$, 4-OCHF$_2$
3-CF$_3$, 5-OCHF$_2$
3-CF$_3$, 6-OCHF$_2$
4-CF$_3$, 2-OCHF$_2$
4-CF$_3$, 3-OCHF$_2$
2-CSNH$_2$
3-CSNH$_2$
4-CSNH$_2$
2,4,6-(CH$_3$)$_3$
3,4,5-(CH$_3$)$_3$
2-CH$_2$CH$_3$
3-CH$_2$CH$_3$
4-CH$_2$CH$_3$
2-CH$_2$CH$_2$CH$_3$
3-CH$_2$CH$_2$CH$_3$
4-CH$_2$CH$_2$CH$_3$
2-CH(CH$_3$)$_3$
3-CH(CH$_3$)$_3$
4-CH(CH$_3$)$_3$
3-C(CH$_3$)$_3$
4-C(CH$_3$)$_3$
3-C$_6$H$_5$
4-C$_6$H$_5$
3,5-(CF$_3$)$_2$
2,3-(OCH$_3$)$_2$
2,4-(OCH$_3$)$_2$
2,5-(OCH$_3$)$_2$
2,6-(OCH$_3$)$_2$
3,4-(OCH$_3$)$_2$
3,5-(OCH$_3$)$_2$
3,4,5-(OCH$_3$)$_3$
2-OCH$_3$
3-OCH$_3$
4-OCH$_3$
2-OCH$_2$CH$_3$
3-OCH$_2$CH$_3$
4-OCH$_2$CH$_3$
2-OCH$_2$CH$_2$CH$_3$
3-OCH$_2$CH$_2$CH$_3$
4-OCH$_2$CH$_2$CH$_3$
2-OCH(CH$_3$)$_3$
3-OCH(CH$_3$)$_3$
4-OCH(CH$_3$)$_3$
3-OC(CH$_3$)$_3$
4-OC(CH$_3$)$_3$
2-OCF$_3$
3-OCF$_3$
4-OCF$_3$
2-OCHF$_2$
3-OCHF$_2$
4-OCHF$_2$
2-OCF$_2$CHF$_2$
3-OCF$_2$CHF$_2$
4-OCF$_2$CHF$_2$
2-OH
3-OH
4-OH
2-NH$_2$
3-NH$_2$
4-NH$_2$
2-NH(CH$_3$)
3-NH(CH$_3$)
4-NH(CH$_3$)
2-N(CH$_3$)$_2$
3-N(CH$_3$)$_2$
4-N(CH$_3$)$_2$
2-SCH$_3$
3-SCH$_3$
4-SCH$_3$
2-SO$_2$CH$_3$
3-SO$_2$CH$_3$

TABLE A-continued

| | |
|---|---|
| 4-SO$_2$CH$_3$ | 4-F |
| 2-COCH$_3$ | 2,3-F$_2$ |
| 3-COCH$_3$ | 2,4-F$_2$ |
| 4-COCH$_3$ | 2,5-F$_2$ |
| 2-CO$_2$H | 2,6-F$_2$ |
| 3-CO$_2$H | 3,4-F$_2$ |
| 4-CO$_2$H | 3,5-F$_2$ |
| 2-CONH$_2$ | 3,4-Cl$_2$ |
| 3-CONH$_2$ | 2,3,4-Cl$_3$ |
| 4-CONH$_2$ | 2,3,5-Cl$_3$ |
| 2-COOCH$_3$ | 2,3,6-Cl$_3$ |
| 3-COOCH$_3$ | 2,4,5-Cl$_3$ |
| 4-COOCH$_3$ | 2,4,6-Cl$_3$ |
| 2-COOCH$_2$CH$_3$ | 3,4,5-Cl$_3$ |
| 3-COOCH$_2$CH$_3$ | 2-Br |
| 4-COOCH$_2$CH$_3$ | 3-Br |
| 2-COOCH$_2$CH$_2$CH$_3$ | 4-Br |
| 3-COOCH$_2$CH$_2$CH$_3$ | 2,3-Br$_2$ |
| 4-COOCH$_2$CH$_2$CH$_3$ | 2,4-Br$_2$ |
| 2-COOCH(CH$_3$)$_3$ | 2,5-Br$_2$ |
| 3-COOCH(CH$_3$)$_3$ | 2,6-Br$_2$ |
| 4-COOCH(CH$_3$)$_3$ | 3,4-Br$_2$ |
| 3-COOC(CH$_3$)$_3$ | 3,5-Br$_2$ |
| 4-COOC(CH$_3$)$_3$ | 2-I |
| 2,3-[OCH$_2$O] | 3-I |
| 3,4-[OCH$_2$O] | 4-I |
| 2,3-[OC(CH$_3$)$_2$O] | 2,4-I$_2$ |
| 3,4-[OC(CH$_3$)$_2$O] | 2-F, 3-Cl |
| 2,3-[OCH$_2$CH$_2$O] | 2-F, 4-Cl |
| 3,4-[OCH$_2$CH$_2$O] | 2-F, 5-Cl |
| 2,3-[OCF$_2$O] | 2-F, 6-Cl |
| 3,4-[OCF$_2$O] | 3-F, 2-Cl |
| 2,3-[CH$_2$]$_4$ | 3-F, 4-Cl |
| 3,4-[CH$_2$]$_4$ | 3-F, 5-Cl |
| 2,3-[CH=CH—CH=CH] | 3-F, 6-Cl |
| 3,4-[CH=CH—CH=CH] | 4-F, 2-Cl |
| | 4-F, 3-Cl |
| | 2-F, 3-Br |
| | 2-F, 4-Br |
| | 2-F, 5-Br |
| | 2-F, 6-Br |
| | 3-F, 2-Br |
| | 3-F, 4-Br |
| | 3-F, 5-Br |
| | 3-F, 6-Br |
| | 4-F, 2-Br |
| | 4-F, 3-Br |

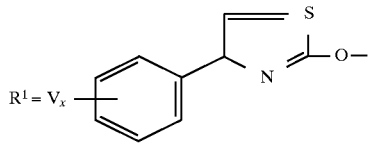

| V$_x$ | |
|---|---|
| H | |
| 2-Cl | 2-Br, 3-Cl |
| 3-Cl | 2-Br, 4-Cl |
| 4-Cl | 2-Br, 5-Cl |
| 2,3-Cl$_2$ | 2-Br, 6-Cl |
| 2,4-Cl$_2$ | 3-Br, 2-Cl |
| 2,5-Cl$_2$ | 3-Br, 4-Cl |
| 2,6-Cl$_2$ | 3-Br, 5-Cl |
| 3,5-Cl$_2$ | 3-Br, 6-Cl |
| 2-CH$_3$ | 4-Br, 2-Cl |
| 3-CH$_3$ | 4-Br, 3-Cl |
| 4-CH$_3$ | 2-Cl, 3-CN |
| 2,3-(CH$_3$)$_2$ | 2-Cl, 4-CN |
| 2,4-(CH$_3$)$_2$ | 2-Cl, 5-CN |
| 2,5-(CH$_3$)$_2$ | 2-Cl, 6-CN |
| 2,6-(CH$_3$)$_2$ | 3-Cl, 2-CN |
| 3,4-(CH$_3$)$_2$ | 3-Cl, 4-CN |
| 3,5-(CH$_3$)$_2$ | 3-Cl, 5-CN |
| 2-NO$_2$ | 3-Cl, 6-CN |
| 3-NO$_2$ | 4-Cl, 2-CN |
| 4-NO$_2$ | 2-F, 6-CN |
| 2-CN | 3-F, 2-CN |
| 3-CN | 3-F, 4-CN |
| 4-CN | 3-F, 5-CN |
| 2-OCH$_3$ | 3-F, 6-CN |
| 3-OCH$_3$ | 4-F, 2-CN |
| 4-OCH$_3$ | 4-F, 3-CN |
| 2-CF$_3$ | 2-Cl, 3-CH$_3$ |
| 3-CF$_3$ | 2-Cl, 4-CH$_3$ |
| 4-CF$_3$ | 2-Cl, 5-CH$_3$ |
| 2-F | 2-Cl, 6-CH$_3$ |
| 3-F | 3-Cl, 2-CH$_3$ |
| | 3-Cl, 4-CH$_3$ |

TABLE A-continued

| | |
|---|---|
| 3-Cl, 5-CH₃ | 3-CH₃, 4-OCH₃ |
| 3-Cl, 6-CH₃ | 3-CH₃, 5-OCH₃ |
| 4-Cl, 2-CH₃ | 3-CH₃, 6-OCH₃ |
| 4-Cl, 3-CH₃ | 4-CH₃, 2-OCH₃ |
| 2-F, 3-CH₃ | 4-CH₃, 3-OCH₃ |
| 2-F, 4-CH₃ | 2-CF₃, 3-OCH₃ |
| 2-F, 5-CH₃ | 2-CF₃, 4-OCH₃ |
| 2-F, 6-CH₃ | 2-CF₃, 5-OCH₃ |
| 3-F, 2-CH₃ | 2-CF₃, 6-OCH₃ |
| 3-F, 4-CH₃ | 3-CF₃, 2-OCH₃ |
| 3-F, 5-CH₃ | 3-CF₃, 4-OCH₃ |
| 3-F, 6-CH₃ | 3-CF₃, 5-OCH₃ |
| 4-F, 2-CH₃ | 3-CF₃, 6-OCH₃ |
| 4-F, 3-CH₃ | 4-CF₃, 2-OCH₃ |
| 2-CN, 3-CH₃ | 4-CF₃, 3-OCH₃ |
| 2-CN, 4-CH₃ | 2-Cl, 3-OCF₃ |
| 2-CN, 5-CH₃ | 2-Cl, 4-OCF₃ |
| 2-CN, 6-CH₃ | 2-Cl, 5-OCF₃ |
| 3-CN, 2-CH₃ | 2-Cl, 6-OCF₃ |
| 3-CN, 4-CH₃ | 3-Cl, 2-OCF₃ |
| 3-CN, 5-CH₃ | 3-Cl, 4-OCF₃ |
| 3-CN, 6-CH₃ | 3-Cl, 6-OCF₃ |
| 4-CN, 2-CH₃ | 4-Cl, 2-OCF₃ |
| 4-CN, 3-CH₃ | 4-Cl, 3-OCF₃ |
| 2-Cl, 3-CF₃ | 2-F, 3-OCF₃ |
| 2-Cl, 4-CF₃ | 2-F, 4-OCF₃ |
| 2-Cl, 5-CF₃ | 2-F, 5-OCF₃ |
| 2-Cl, 6-CF₃ | 2-F, 6-OCF₃ |
| 3-Cl, 2-CF₃ | 3-F, 2-OCF₃ |
| 3-Cl, 4-CF₃ | 3-F, 4-OCF₃ |
| 3-Cl, 5-CF₃ | 3-F, 5-OCF₃ |
| 3-Cl, 6-CF₃ | 3-F, 6-OCF₃ |
| 4-Cl, 2-CF₃ | 4-F, 2-OCF₃ |
| 4-Cl, 3-CF₃ | 4-F, 3-OCF₃ |
| 2-F, 3-CF₃ | 2-CN, 3-OCF₃ |
| 2-F, 4-CF₃ | 2-CN, 4-OCF₃ |
| 2-F, 5-CF₃ | 2-CN, 5-OCF₃ |
| 2-F, 6-CF₃ | 2-CN, 6-OCF₃ |
| 3-F, 2-CF₃ | 3-CN, 2-OCF₃ |
| 3-F, 4-CF₃ | 3-CN, 4-OCF₃ |
| 3-F, 5-CF₃ | 3-CN, 5-OCF₃ |
| 3-F, 6-CF₃ | 3-CN, 6-OCF₃ |
| 4-F, 2-CF₃ | 4-CN, 2-OCF₃ |
| 4-F, 3-CF₃ | 4-CN, 3-OCF₃ |
| 2-Cl, 3-OCH₃ | 2-CH₃, 3-OCF₃ |
| 2-Cl, 4-OCH₃ | 2-CH₃, 4-OCF₃ |
| 2-Cl, 5-OCH₃ | 2-CH₃, 5-OCF₃ |
| 2-Cl, 6-OCH₃ | 2-CH₃, 6-OCF₃ |
| 3-Cl, 2-OCH₃ | 3-CH₃, 2-OCF₃ |
| 3-Cl, 4-OCH₃ | 3-CH₃, 4-OCF₃ |
| 3-Cl, 5-OCH₃ | 3-CH₃, 5-OCF₃ |
| 3-Cl, 6-OCH₃ | 3-CH₃, 6-OCF₃ |
| 4-Cl, 2-OCH₃ | 4-CH₃, 2-OCF₃ |
| 4-Cl, 3-OCH₃ | 4-CH₃, 3-OCF₃ |
| 2-F, 3-OCH₃ | 2-CF₃, 3-OCF₃ |
| 2-F, 4-OCH₃ | 2-CF₃, 4-OCF₃ |
| 2-F, 5-OCH₃ | 2-CF₃, 5-OCF₃ |
| 2-F, 6-OCH₃ | 2-CF₃, 6-OCF₃ |
| 3-F, 2-OCH₃ | 3-CF₃, 2-OCF₃ |
| 3-F, 4-OCH₃ | 3-CF₃, 4-OCF₃ |
| 3-F, 5-OCH₃ | 3-CF₃, 5-OCF₃ |
| 3-F, 6-OCH₃ | 3-CF₃, 6-OCF₃ |
| 4-F, 2-OCH₃ | 4-CF₃, 2-OCF₃ |
| 4-F, 3-OCH₃ | 4-CF₃, 3-OCF₃ |
| 2-CN, 3-OCH₃ | 2-Cl, 3-OCHF₂ |
| 2-CN, 4-OCH₃ | 2-Cl, 4-OCHF₂ |
| 2-CN, 5-OCH₃ | 2-Cl, 5-OCHF₂ |
| 2-CN, 6-OCH₃ | 2-Cl, 6-OCHF₂ |
| 3-CN, 2-OCH₃ | 3-Cl, 2-OCHF₂ |
| 3-CN, 4-OCH₃ | 3-Cl, 4-OCHF₂ |
| 3-CN, 5-OCH₃ | 3-Cl, 5-OCHF₂ |
| 3-CN, 6-OCH₃ | 3-Cl, 6-OCHF₂ |
| 4-CN, 2-OCH₃ | 4-Cl, 2-OCHF₂ |
| 4-CN, 3-OCH₃ | 4-Cl, 3-OCHF₂ |
| 2-CH₃, 3-OCH₃ | 2-F, 4-OCHF₂ |
| 2-CH₃, 4-OCH₃ | 2-F, 5-OCHF₂ |
| 2-CH₃, 5-OCH₃ | 2-F, 6-OCHF₂ |
| 2-CH₃, 6-OCH₃ | 3-F, 2-OCHF₂ |
| 3-CH₃, 2-OCH₃ | 3-F, 4-OCHF₂ |

TABLE A-continued

3-F, 5-OCHF$_2$
3-F, 6-OCHF$_2$
4-F, 2-OCHF$_2$
4-F, 3-OCHF$_2$
2-CN, 3-OCHF$_2$
2-CN, 4-OCHF$_2$
2-CN, 5-OCHF$_2$
2-CN, 6-OCHF$_2$
3-CN, 2-OCHF$_2$
3-CN, 4-OCHF$_2$
3-CN, 5-OCHF$_2$
3-CN, 6-OCHF$_2$
4-CN, 2-OCHF$_2$
4-CN, 3-OCHF$_2$
2-CH$_3$, 3-OCHF$_2$
2-CH$_3$, 4-OCHF$_2$
2-CH$_3$, 5-OCHF$_2$
2-CH$_3$, 6-OCHF$_2$
3-CH$_3$, 2-OCHF$_2$
3-CH$_3$, 4-OCHF$_2$
3-CH$_3$, 5-OCHF$_2$
3-CH$_3$, 6-OCHF$_2$
4-CH$_3$, 2-OCHF$_2$
4-CH$_3$, 3-OCHF$_2$
2-CF$_3$, 3-OCHF$_2$
2-CF$_3$, 4-OCHF$_2$
2-CF$_3$, 5-OCHF$_2$
2-CF$_3$, 6-OCHF$_2$
3-CF$_3$, 2-OCHF$_2$
3-CF$_3$, 4-OCHF$_2$
3-CF$_3$, 5-OCHF$_2$
3-CF$_3$, 6-OCHF$_2$
4-CF$_3$, 2-OCHF$_2$
4-CF$_3$, 3-OCHF$_2$
2-CSNH$_2$
3-CSNH$_2$
4-CSNH$_2$
2,4,6-(CH$_3$)$_3$
3,4,5-(CH$_3$)$_3$
2-CH$_2$CH$_3$
3-CH$_2$CH$_3$
4-CH$_2$CH$_3$
2-CH$_2$CH$_2$CH$_3$
3-CH$_2$CH$_2$CH$_3$
4-CH$_2$CH$_2$CH$_3$
2-CH(CH$_3$)$_2$
3-CH(CH$_3$)$_2$
4-CH(CH$_3$)$_2$
3-C(CH$_3$)$_3$
4-C(CH$_3$)$_3$
3-C$_6$H$_5$
4-C$_6$H$_5$
3,5-(CF$_3$)$_2$
2,3-(OCH$_3$)$_2$
2,4-(OCH$_3$)$_2$
2,5-(OCH$_3$)$_2$
2,6-(OCH$_3$)$_2$
3,4-(OCH$_3$)$_2$
3,5-(OCH$_3$)$_2$
3,4,5-(OCH$_3$)$_3$
2-OCH$_3$
3-OCH$_3$
4-OCH$_3$
2-OCH$_2$CH$_3$
3-OCH$_2$CH$_3$
4-OCH$_2$CH$_3$
2-OCH$_2$CH$_2$CH$_3$
3-OCH$_2$CH$_2$CH$_3$
4-OCH$_2$CH$_2$CH$_3$
2-OCH(CH$_3$)$_3$
3-OCH(CH$_3$)$_3$
4-OCH(CH$_3$)$_3$
3-OC(CH$_3$)$_3$
4-OC(CH$_3$)$_3$
2-OCF$_3$
3-OCF$_3$
4-OCF$_3$
2-OCHF$_2$
3-OCHF$_2$

TABLE A-continued

4-OCHF$_2$
2-OCF$_2$CHF$_2$
3-OCF$_2$CHF$_2$
4-OCF$_2$CHF$_2$
2-OH
3-OH
4-OH
2-NH$_2$
3-NH$_2$
4-NH$_2$
2-NH(CH$_3$)
3-NH(CH$_3$)
4-NH(CH$_3$)
2-N(CH$_3$)$_2$
3-N(CH$_3$)$_2$
4-N(CH$_3$)$_2$
2-SCH$_3$
3-SCH$_3$
4-SCH$_3$
2-SO$_2$CH$_3$
3-SO$_2$CH$_3$
4-SO$_2$CH$_3$
2-COCH$_3$
3-COCH$_3$
4-COCH$_3$
2-CO$_2$H
3-CO$_2$H
4-CO$_2$H
2-CONH$_2$
3-CONH$_2$
4-CONH$_2$
2-COOCH$_3$
3-COOCH$_3$
4-COOCH$_3$
2-COOCH$_2$CH$_3$
3-COOCH$_2$CH$_3$
4-COOCH$_2$CH$_3$
2-COOCH$_2$CH$_2$CH$_3$
3-COOCH$_2$CH$_2$CH$_3$
4-COOCH$_2$CH$_2$CH$_3$
2-COOCH(CH$_3$)$_3$
3-COOCH(CH$_3$)$_3$
4-COOCH(CH$_3$)$_3$
3-COOC(CH$_3$)$_3$
4-COOC(CH$_3$)$_3$
2,3-[OCH$_2$O]
3,4-[OCH$_2$O]
2,3-[OCH$_2$CH$_2$O]
3,4-[OCH$_2$CH$_2$O]
2,3-[OCF$_2$O]
3,4-[OCF$_2$O]
2,3-[CH$_2$]$_4$
3,4-[CH$_2$]$_4$
2,3-[CH=CH—CH=CH]
3,4-[CH=CH—CH=CH]

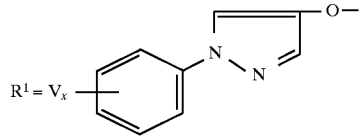

$R^1 = V_x$

| $V_x$ |
|---|
| H |
| 2-Cl |
| 3-Cl |
| 4-Cl |
| 2,3-Cl$_2$ |
| 2,4-Cl$_2$ |
| 2,5-Cl$_2$ |
| 2,6-Cl$_2$ |
| 3,5-Cl$_2$ |
| 2-CH$_3$ |
| 3-CH$_3$ |
| 4-CH$_3$ |
| 2,3-(CH$_3$)$_2$ |

TABLE A-continued 2,4-(CH$_3$)$_2$
2,5-(CH$_3$)$_2$
2,6-(CH$_3$)$_2$
3,4-(CH$_3$)$_2$
3,5-(CH$_3$)$_2$
2-NO$_2$
3-NO$_2$
4-NO$_2$
2-CN
3-CN
4-CN
2-OCH$_3$
3-OCH$_3$
4-OCH$_3$
2-CF$_3$
3-CF$_3$
4-CF$_3$
2-F
3-F
4-F
2,3-F$_2$
2,4-F$_2$
2,5-F$_2$
2,6-F$_2$
3,4-F$_2$
3,5-F$_2$
3,4-Cl$_2$
2,3,4-Cl$_3$
2,3,5-Cl$_3$
2,3,6-Cl$_3$
2,4,5-Cl$_3$
2,4,6-Cl$_3$
3,4,5-Cl$_3$
2-Br
3-Br
4-Br
2,3-Br$_2$
2,4-Br$_2$
2,5-Br$_2$
2,6-Br$_2$
3,4-Br$_2$
3,5-Br$_2$
2-I
3-I
4-I
2,4-I$_2$
2-F, 3-Cl
2-F, 4-Cl
2-F, 5-Cl
2-F, 6-Cl
3-F, 2-Cl
3-F, 4-Cl
3-F, 5-Cl
3-F, 6-Cl
4-F, 2-Cl
4-F, 3-Cl
2-F, 3-Br
2-F, 4-Br
2-F, 5-Br
2-F, 6-Br
3-F, 2-Br
3-F, 4-Br
3-F, 5-Br
3-F, 6-Br
4-F, 2-Br
4-F, 3-Br
2-Br, 3-Cl
2-Br, 4-Cl
2-Br, 5-Cl
2-Br, 6-Cl
3-Br, 2-Cl
3-Br, 4-Cl
3-Br, 5-Cl
3-Br, 6-Cl
4-Br, 2-Cl
4-Br, 3-Cl
2-Cl, 3-CN
2-Cl, 4-CN
2-Cl, 5-CN

TABLE A-continued

2-Cl, 6-CN
3-Cl, 2-CN
3-Cl, 4-CN
3-Cl, 5-CN
3-Cl, 6-CN
4-Cl, 2-CN
4-Cl, 3-CN
2-F, 3-CN
2-F, 4-CN
2-F, 5-CN
2-F, 6-CN
3-F, 2-CN
3-F, 4-CN
3-F, 5-CN
3-F, 6-CN
4-F, 2-CN
4-F, 3-CN
2-Cl, 3-CH$_3$
2-Cl, 4-CH$_3$
2-Cl, 5-CH$_3$
2-Cl, 6-CH$_3$
3-Cl, 2-CH$_3$
3-Cl, 4-CH$_3$
3-Cl, 5-CH$_3$
3-Cl, 6-CH$_3$
4-Cl, 2-CH$_3$
4-Cl, 3-CH$_3$
2-F, 3-CH$_3$
2-F, 4-CH$_3$
2-F, 5-CH$_3$
2-F, 6-CH$_3$
3-F, 2-CH$_3$
3-F, 4-CH$_3$
3-F, 5-CH$_3$
3-F, 6-CH$_3$
4-F, 2-CH$_3$
4-F, 3-CH$_3$
2-CN, 3-CH$_3$
2-CN, 4-CH$_3$
2-CN, 5-CH$_3$
2-CN, 6-CH$_3$
3-CN, 2-CH$_3$
3-CN, 4-CH$_3$
3-CN, 5-CH$_3$
3-CN, 6-CH$_3$
4-CN, 2-CH$_3$
4-CN, 3-CH$_3$
2-Cl, 3-CF$_3$
2-Cl, 4-CF$_3$
2-Cl, 5-CF$_3$
2-Cl, 6-CF$_3$
3-Cl, 2-CF$_3$
3-Cl, 4-CF$_3$
3-Cl, 5-CF$_3$
3-Cl, 6-CF$_3$
4-Cl, 2-CF$_3$
4-Cl, 3-CF$_3$
2-F, 3-CF$_3$
2-F, 4-CF$_3$
2-F, 5-CF$_3$
2-F, 6-CF$_3$
3-F, 2-CF$_3$
3-F, 4-CF$_3$
3-F, 5-CF$_3$
3-F, 6-CF$_3$
4-F, 2-CF$_3$
4-F, 3-CF$_3$
2-Cl, 3-OCH$_3$
2-Cl, 4-OCH$_3$
2-Cl, 5-OCH$_3$
2-Cl, 6-OCH$_3$
3-Cl, 2-OCH$_3$
3-Cl, 4-OCH$_3$
3-Cl, 5-OCH$_3$
3-Cl, 6-OCH$_3$
4-Cl, 2-OCH$_3$
4-Cl, 3-OCH$_3$
2-F, 3-OCH$_3$
2-F, 4-OCH$_3$

TABLE A-continued

2-F, 5-OCH₃
2-F, 6-OCH₃
3-F, 2-OCH₃
3-F, 4-OCH₃
3-F, 5-OCH₃
3-F, 6-OCH₃
4-F, 2-OCH₃
4-F, 3-OCH₃
2-CN, 3-OCH₃
2-CN, 4-OCH₃
2-CN, 5-OCH₃
2-CN, 6-OCH₃
3-CN, 2-OCH₃
3-CN, 4-OCH₃
3-CN, 5-OCH₃
3-CN, 6-OCH₃
4-CN, 2-OCH₃
4-CN, 3-OCH₃
2-CH₃, 3-OCH₃
2-CH₃, 4-OCH₃
2-CH₃, 5-OCH₃
2-CH₃, 6-OCH₃
3-CH₃, 2-OCH₃
3-CH₃, 4-OCH₃
3-CH₃, 5-OCH₃
3-CH₃, 6-OCH₃
4-CH₃, 2-OCH₃
4-CH₃, 3-OCH₃
2-CF₃, 3-OCH₃
2-CF₃, 4-OCH₃
2-CF₃, 5-OCH₃
2-CF₃, 6-OCH₃
3-CF₃, 2-OCH₃
3-CF₃, 4-OCH₃
3-CF₃, 5-OCH₃
3-CF₃, 6-OCH₃
4-CF₃, 2-OCH₃
4-CF₃, 3-OCH₃
2-Cl, 3-OCF₃
2-Cl, 4-OCF₃
2-Cl, 5-OCF₃
2-Cl, 6-OCF₃
3-Cl, 2-OCF₃
3-Cl, 4-OCF₃
3-Cl, 5-OCF₃
3-Cl, 6-OCF₃
4-Cl, 2-OCF₃
4-Cl, 3-OCF₃
2-F, 3-OCF₃
2-F, 4-OCF₃
2-F, 5-OCF₃
2-F, 6-OCF₃
3-F, 2-OCF₃
3-F, 4-OCF₃
3-F, 5-OCF₃
3-F, 6-OCF₃
4-F, 2-OCF₃
4-F, 3-OCF₃
2-CN, 3-OCF₃
2-CN, 4-OCF₃
2-CN, 5-OCF₃
2-CN, 6-OCF₃
3-CN, 2-OCF₃
3-CN, 4-OCF₃
3-CN, 5-OCF₃
3-CN, 6-OCF₃
4-CN, 2-OCF₃
4-CN, 3-OCF₃
2-CH₃, 3-OCF₃
2-CH₃, 4-OCF₃
2-CH₃, 5-OCF₃
2-CH₃, 6-OCF₃
3-CH₃, 2-OCF₃
3-CH₃, 4-OCF₃
3-CH₃, 5-OCF₃
3-CH₃, 6-OCF₃
4-CH₃, 2-OCF₃
4-CH₃, 3-OCF₃
2-CF₃, 3-OCF₃

TABLE A-continued

2-CF₃, 4-OCF₃
2-CF₃, 5-OCF₃
2-CF₃, 6-OCF₃
3-CF₃, 2-OCF₃
3-CF₃, 4-OCF₃
3-CF₃, 5-OCF₃
3-CF₃, 6-OCF₃
4-CF₃, 2-OCF₃
4-CF₃, 3-OCF₃
2-Cl, 3-OCHF₂
2-Cl, 4-OCHF₂
2-Cl, 5-OCHF₂
2-Cl, 6-OCHF₂
3-Cl, 2-OCHF₂
3-Cl, 4-OCHF₂
3-Cl, 5-OCHF₂
3-Cl, 6-OCHF₂
4-Cl, 2-OCHF₂
4-Cl, 3-OCHF₂
2-F, 3-OCHF₂
2-F, 4-OCHF₂
2-F, 5-OCHF₂
2-F, 6-OCHF₂
3-F, 2-OCHF₂
3-F, 4-OCHF₂
3-F, 5-OCHF₂
3-F, 6-OCHF₂
4-F, 2-OCHF₂
4-F, 3-OCHF₂
2-CN, 3-OCHF₂
2-CN, 4-OCHF₂
2-CN, 5-OCHF₂
2-CN, 6-OCHF₂
3-CN, 2-OCHF₂
3-CN, 4-OCHF₂
3-CN, 5-OCHF₂
3-CN, 6-OCHF₂
4-CN, 2-OCHF₂
4-CN, 3-OCHF₂
2-CH₃, 3-OCHF₂
2-CH₃, 4-OCHF₂
2-CH₃, 5-OCHF₂
2-CH₃, 6-OCHF₂
3-CH₃, 2-OCHF₂
3-CH₃, 4-OCHF₂
3-CH₃, 5-OCHF₂
3-CH₃, 6-OCHF₂
4-CH₃, 2-OCHF₂
4-CH₃, 3-OCHF₂
2-CF₃, 3-OCHF₂
2-CF₃, 4-OCHF₂
2-CF₃, 5-OCHF₂
2-CF₃, 6-OCHF₂
3-CF₃, 2-OCHF₂
3-CF₃, 4-OCHF₂
3-CF₃, 5-OCHF₂
3-CF₃, 6-OCHF₂
4-CF₃, 2-OCHF₂
4-CF₃, 3-OCHF₂
2-CSNH₂
3-CSNH₂
4-CSNH₂
2,4,6-(CH₃)₃
3,4,5-(CH₃)₃
2-CH₂CH₃
3-CH₂CH₃
4-CH₂CH₃
2-CH₂CH₂CH₃
3-CH₂CH₂CH₃
4-CH₂CH₂CH₃
2-CH(CH₃)₃
3-CH(CH₃)₃
4-CH(CH₃)₃
3-C(CH₃)₃
4-C(CH₃)₃
3-C₆H₅
4-C₆H₅
3,5-(CF₃)₂
2,3-(OCH₃)₂

TABLE A-continued 2,4-(OCH$_3$)$_2$
2,5-(OCH$_3$)$_2$
2,6-(OCH$_3$)$_2$
3,4-(OCH$_3$)$_2$
3,5-(OCH$_3$)$_2$
3,4,5-(OCH$_3$)$_3$
2-OCH$_3$
3-OCH$_3$
4-OCH$_3$
2-OCH$_2$CH$_3$
3-OCH$_2$CH$_3$
4-OCH$_2$CH$_3$
2-OCH$_2$CH$_2$CH$_3$
3-OCH$_2$CH$_2$CH$_3$
4-OCH$_2$CH$_2$CH$_3$
2-OCH(CH$_3$)$_3$
3-OCH(CH$_3$)$_3$
4-OCH(CH$_3$)$_3$
3-OC(CH$_3$)$_3$
4-OC(CH$_3$)$_3$
2-OCF$_3$
3-OCF$_3$
4-OCF$_3$
2-OCHF$_2$
3-OCHF$_2$
4-OCHF$_2$
2-OCF$_2$CHF$_2$
3-OCF$_2$CHF$_2$
4-OCF$_2$CHF$_2$
2-OH
3-OH
4-OH
2-NH$_2$
3-NH$_2$
4-NH$_2$
2-NH(CH$_3$)
3-NH(CH$_3$)
4-NH(CH$_3$)
2-N(CH$_3$)$_2$
3-N(CH$_3$)$_2$
4-N(CH$_3$)$_2$
2-SCH$_3$
3-SCH$_3$
4-SCH$_3$
2-SO$_2$CH$_3$
3-SO$_2$CH$_3$
4-SO$_2$CH$_3$
2-COCH$_3$
3-COCH$_3$
4-COCH$_3$
2-CO$_2$H
3-CO$_2$H
4-CO$_2$H
2-CONH$_2$
3-CONH$_2$
4-CONH$_2$
2-COOCH$_3$
3-COOCH$_3$
4-COOCH$_3$
2-COOCH$_2$CH$_3$
3-COOCH$_2$CH$_3$
4-COOCH$_2$CH$_3$
2-COOCH$_2$CH$_2$CH$_3$
3-COOCH$_2$CH$_2$CH$_3$
4-COOCH$_2$CH$_2$CH$_3$
2-COOCH(CH$_3$)$_3$
3-COOCH(CH$_3$)$_3$
4-COOCH(CH$_3$)$_3$
3-COOC(CH$_3$)$_3$
4-COOC(CH$_3$)$_3$
2,3-[OCH$_2$O]
3,4-[OCH$_2$O]
2,3-[OC(CH$_3$)$_2$O]
3,4-[OC(CH$_3$)$_2$O]
2,3-[OCH$_2$CH$_2$O]
3,4-[OCH$_2$CH$_2$O]
2,3-[OCF$_2$O]
3,4-[OCF$_2$O]
2,3-[CH$_2$]$_4$ TABLE A-continued 3,4-[CH$_2$]$_4$
2,3-[CH=CH—CH=CH]
3,4-[CH=CH—CH=CH]

$R^1 = V_x$

| $V_x$ |
|---|
| H |
| 2-Cl |
| 3-Cl |
| 4-Cl |
| 2,3-Cl$_2$ |
| 2,4-Cl$_2$ |
| 2,5-Cl$_2$ |
| 2,6-Cl$_2$ |
| 3,5-Cl$_2$ |
| 2-CH$_3$ |
| 3-CH$_3$ |
| 4-CH$_3$ |
| 2,3-(CH$_3$)$_2$ |
| 2,4-(CH$_3$)$_2$ |
| 2,5-(CH$_3$)$_2$ |
| 2,6-(CH$_3$)$_2$ |
| 3,4-(CH$_3$)$_2$ |
| 3,5-(CH$_3$)$_2$ |
| 2-NO$_2$ |
| 3-NO$_2$ |
| 4-NO$_2$ |
| 2-CN |
| 3-CN |
| 4-CN |
| 2-OCH$_3$ |
| 3-OCH$_3$ |
| 4-OCH$_3$ |
| 2-CF$_3$ |
| 3-CF$_3$ |
| 4-CF$_3$ |
| 2-F |
| 3-F |
| 4-F |
| 2,3-F$_2$ |
| 2,4-F$_2$ |
| 2,5-F$_2$ |
| 2,6-F$_2$ |
| 3,4-F$_2$ |
| 3,5-F$_2$ |
| 3,4-Cl$_2$ |
| 2,3,4-Cl$_3$ |
| 2,3,5-Cl$_3$ |
| 2,3,6-Cl$_3$ |
| 2,4,5-Cl$_3$ |
| 2,4,6-Cl$_3$ |
| 3,4,5-Cl$_3$ |
| 2-Br |
| 3-Br |
| 4-Br |
| 2,3-Br$_2$ |
| 2,4-Br$_2$ |
| 2,5-Br$_2$ |
| 2,6-Br$_2$ |
| 3,4-Br$_2$ |
| 3,5-Br$_2$ |
| 2-I |
| 3-I |
| 4-I |
| 2,4-I$_2$ |
| 2-F, 3-Cl |
| 2-F, 4-Cl |
| 2-F, 5-Cl |
| 2-F, 6-Cl |
| 3-F, 2-Cl |
| 3-F, 4-Cl |

TABLE A-continued

| | |
|---|---|
| 3-F, 5-Cl | 3-Cl, 4-CF$_3$ |
| 3-F, 6-Cl | 3-Cl, 5-CF$_3$ |
| 4-F, 2-Cl | 3-Cl, 6-CF$_3$ |
| 4-F, 3-Cl | 4-Cl, 2-CF$_3$ |
| 2-F, 3-Br | 4-Cl, 3-CF$_3$ |
| 2-F, 4-Br | 2-F, 3-CF$_3$ |
| 2-F, 5-Br | 2-F, 4-CF$_3$ |
| 2-F, 6-Br | 2-F, 5-CF$_3$ |
| 3-F, 2-Br | 2-F, 6-CF$_3$ |
| 3-F, 4-Br | 3-F, 2-CF$_3$ |
| 3-F, 5-Br | 3-F, 4-CF$_3$ |
| 3-F, 6-Br | 3-F, 5-CF$_3$ |
| 4-F, 2-Br | 3-F, 6-CF$_3$ |
| 4-F, 3-Br | 4-F, 2-CF$_3$ |
| 2-Br, 3-Cl | 4-F, 3-CF$_3$ |
| 2-Br, 4-Cl | 2-Cl, 3-OCH$_3$ |
| 2-Br, 5-Cl | 2-Cl, 4-OCH$_3$ |
| 2-Br, 6-Cl | 2-Cl, 5-OCH$_3$ |
| 3-Br, 2-Cl | 2-Cl, 6-OCH$_3$ |
| 3-Br, 4-Cl | 3-Cl, 2-OCH$_3$ |
| 3-Br, 5-Cl | 3-Cl, 4-OCH$_3$ |
| 3-Br, 6-Cl | 3-Cl, 5-OCH$_3$ |
| 4-Br, 2-Cl | 3-Cl, 6-OCH$_3$ |
| 4-Br, 3-Cl | 4-Cl, 2-OCH$_3$ |
| 2-Cl, 3-CN | 4-Cl, 3-OCH$_3$ |
| 2-Cl, 4-CN | 2-F, 3-OCH$_3$ |
| 2-Cl, 5-CN | 2-F, 4-OCH$_3$ |
| 2-Cl, 6-CN | 2-F, 5-OCH$_3$ |
| 3-Cl, 2-CN | 2-F, 6-OCH$_3$ |
| 3-Cl, 4-CN | 3-F, 2-OCH$_3$ |
| 3-Cl, 5-CN | 3-F, 4-OCH$_3$ |
| 3-Cl, 6-CN | 3-F, 5-OCH$_3$ |
| 4-Cl, 2-CN | 3-F, 6-OCH$_3$ |
| 4-Cl, 3-CN | 4-F, 2-OCH$_3$ |
| 2-F, 3-CN | 4-F, 3-OCH$_3$ |
| 2-F, 4-CN | 2-CN, 3-OCH$_3$ |
| 2-F, 5-CN | 2-CN, 4-OCH$_3$ |
| 2-F, 6-CN | 2-CN, 5-OCH$_3$ |
| 3-F, 2-CN | 2-CN, 6-OCH$_3$ |
| 3-F, 4-CN | 3-CN, 2-OCH$_3$ |
| 3-F, 5-CN | 3-CN, 4-OCH$_3$ |
| 3-F, 6-CN | 3-CN, 5-OCH$_3$ |
| 4-F, 2-CN | 3-CN, 6-OCH$_3$ |
| 4-F, 3-CN | 4-CN, 2-OCH$_3$ |
| 2-Cl, 3-CH$_3$ | 4-CN, 3-OCH$_3$ |
| 2-Cl, 4-CH$_3$ | 2-CH$_3$, 3-OCH$_3$ |
| 2-Cl, 5-CH$_3$ | 2-CH$_3$, 4-OCH$_3$ |
| 2-Cl, 6-CH$_3$ | 2-CH$_3$, 5-OCH$_3$ |
| 3-Cl, 2-CH$_3$ | 2-CH$_3$, 6-OCH$_3$ |
| 3-Cl, 4-CH$_3$ | 3-CH$_3$, 2-OCH$_3$ |
| 3-Cl, 5-CH$_3$ | 3-CH$_3$, 4-OCH$_3$ |
| 3-Cl, 6-CH$_3$ | 3-CH$_3$, 5-OCH$_3$ |
| 4-Cl, 2-CH$_3$ | 3-CH$_3$, 6-OCH$_3$ |
| 4-Cl, 3-CH$_3$ | 4-CH$_3$, 2-OCH$_3$ |
| 2-F, 3-CH$_3$ | 4-CH$_3$, 3-OCH$_3$ |
| 2-F, 4-CH$_3$ | 2-CF$_3$, 2-OCH$_3$ |
| 2-F, 5-CH$_3$ | 2-CF$_3$, 4-OCH$_3$ |
| 2-F, 6-CH$_3$ | 2-CF$_3$, 5-OCH$_3$ |
| 3-F, 2-CH$_3$ | 2-CF$_3$, 6-OCH$_3$ |
| 3-F, 4-CH$_3$ | 3-CF$_3$, 2-OCH$_3$ |
| 3-F, 5-CH$_3$ | 3-CF$_3$, 4-OCH$_3$ |
| 3-F, 6-CH$_3$ | 3-CF$_3$, 5-OCH$_3$ |
| 4-F, 2-CH$_3$ | 3-CF$_3$, 6-OCH$_3$ |
| 4-F, 3-CH$_3$ | 4-CF$_3$, 2-OCH$_3$ |
| 2-CN, 3-CH$_3$ | 4-CF$_3$, 3-OCH$_3$ |
| 2-CN, 4-CH$_3$ | 2-Cl, 3-OCF$_3$ |
| 2-CN, 5-CH$_3$ | 2-Cl, 4-OCF$_3$ |
| 2-CN, 6-CH$_3$ | 2-Cl, 5-OCF$_3$ |
| 3-CN, 2-CH$_3$ | 2-Cl, 6-OCF$_3$ |
| 3-CN, 4-CH$_3$ | 3-Cl, 2-OCF$_3$ |
| 3-CN, 5-CH$_3$ | 3-Cl, 4-OCF$_3$ |
| 3-CN, 6-CH$_3$ | 3-Cl, 5-OCF$_3$ |
| 4-CN, 2-CH$_3$ | 3-Cl, 6-OCF$_3$ |
| 4-CN, 3-CH$_3$ | 4-Cl, 2-OCF$_3$ |
| 2-Cl, 3-CF$_3$ | 4-Cl, 3-OCF$_3$ |
| 2-Cl, 4-CF$_3$ | 2-F, 3-OCF$_3$ |
| 2-Cl, 5-CF$_3$ | 2-F, 4-OCF$_3$ |
| 2-Cl, 6-CF$_3$ | 2-F, 5-OCF$_3$ |
| 3-Cl, 2-CF$_3$ | 2-F, 6-OCF$_3$ |

TABLE A-continued

3-F, 2-OCF$_3$
3-F, 4-OCF$_3$
3-F, 5-OCF$_3$
3-F, 6-OCF$_3$
4-F, 2-OCF$_3$
4-F, 3-OCF$_3$
2-CN, 3-OCF$_3$
2-CN, 4-OCF$_3$
2-CN, 5-OCF$_3$
2-CN, 6-OCF$_3$
3-CN, 2-OCF$_3$
3-CN, 4-OCF$_3$
3-CN, 5-OCF$_3$
3-CN, 6-OCF$_3$
4-CN, 2-OCF$_3$
4-CN, 3-OCF$_3$
2-CH$_3$, 3-OCF$_3$
2-CH$_3$, 4-OCF$_3$
2-CH$_3$, 5-OCF$_3$
2-CH$_3$, 6-OCF$_3$
3-CH$_3$, 2-OCF$_3$
3-CH$_3$, 4-OCF$_3$
3-CH$_3$, 5-OCF$_3$
3-CH$_3$, 6-OCF$_3$
4-CH$_3$, 2-OCF$_3$
4-CH$_3$, 4-OCF$_3$
2-CF$_3$, 3-OCF$_3$
2-CF$_3$, 4-OCF$_3$
2-CF$_3$, 5-OCF$_3$
2-CF$_3$, 6-OCF$_3$
3-CF$_3$, 2-OCF$_3$
3-CF$_3$, 4-OCF$_3$
3-CF$_3$, 5-OCF$_3$
3-CF$_3$, 6-OCF$_3$
4-CF$_3$, 2-OCF$_3$
4-CF$_3$, 3-OCF$_3$
2-Cl, 3-OCHF$_2$
2-Cl, 4-OCHF$_2$
2-Cl, 5-OCHF$_2$
2-Cl, 6-OCHF$_2$
3-Cl, 2-OCHF$_2$
3-Cl, 4-OCHF$_2$
3-Cl, 5-OCHF$_2$
3-Cl, 6-OCHF$_2$
4-Cl, 2-OCHF$_2$
4-Cl, 3-OCHF$_2$
2-F, 3-OCHF$_2$
2-F, 4-OCHF$_2$
2-F, 5-OCHF$_2$
2-F, 6-OCHF$_2$
3-F, 2-OCHF$_2$
3-F, 4-OCHF$_2$
3-F, 5-OCHF$_2$
3-F, 6-OCHF$_2$
4-F, 2-OCHF$_2$
4-F, 3-OCHF$_2$
2-CN, 3-OCHF$_2$
2-CN, 4-OCHF$_2$
2-CN, 5-OCHF$_2$
2-CN, 6-OCHF$_2$
3-CN, 2-OCHF$_2$
3-CN, 4-OCHF$_2$
3-CN, 5-OCHF$_2$
3-CN, 6-OCHF$_2$
4-CN, 2-OCHF$_2$
4-CN, 3-OCHF$_2$
2-CH$_3$, 3-OCHF$_2$
2-CH$_3$, 4-OCHF$_2$
2-CH$_3$, 5-OCHF$_2$
2-CH$_3$, 6-OCHF$_2$
3-CH$_3$, 2-OCHF$_2$
3-CH$_3$, 4-OCHF$_2$
3-CH$_3$, 5-OCHF$_2$
3-CH$_3$, 6-OCHF$_2$
4-CH$_3$, 2-OCHF$_2$
4-CH$_3$, 3-OCHF$_2$
2-CF$_3$, 2-OCHF$_2$
2-CF$_3$, 4-OCHF$_2$
2-CF$_3$, 5-OCHF$_2$

TABLE A-continued

2-CF$_3$, 6-OCHF$_2$
3-CF$_3$, 2-OCHF$_2$
3-CF$_3$, 4-OCHF$_2$
3-CF$_3$, 5-OCHF$_2$
3-CF$_3$, 6-OCHF$_2$
4-CF$_2$, 2-OCHF$_2$
4-CF$_2$, 3-OCHF$_2$
2-CSNH$_2$
3-CSNH$_2$
4-CSNH$_2$
2,4,6-(CH$_3$)$_3$
3,4,5-(CH$_3$)$_3$
2-CH$_2$CH$_3$
3-CH$_2$CH$_3$
4-CH$_2$CH$_3$
2-CH$_2$CH$_2$CH$_3$
3-CH$_2$CH$_2$CH$_3$
4-CH$_2$CH$_2$CH$_3$
2-CH(CH$_3$)$_3$
3-CH(CH$_3$)$_3$
4-CH(CH$_3$)$_3$
3-C(CH$_3$)$_3$
4-C(CH$_3$)$_3$
3-C$_6$H$_5$
4-C$_6$H$_5$
3,5-(CF$_3$)$_2$
2,3-(OCH$_3$)$_2$
2,4-(OCH$_3$)$_2$
2,5-(OCH$_3$)$_2$
2,6-(OCH$_3$)$_2$
3,4-(OCH$_3$)$_2$
3,5-(OCH$_3$)$_2$
3,4,5-(OCH$_3$)$_3$
2-OCH$_3$
3-OCH$_3$
4-OCH$_3$
2-OCH$_2$CH$_3$
3-OCH$_2$CH$_3$
4-OCH$_2$CH$_3$
2-OCH$_2$CH$_2$CH$_3$
3-OCH$_2$CH$_2$CH$_3$
4-OCH$_2$CH$_2$CH$_3$
2-OCH(CH$_3$)$_3$
3-OCH(CH$_3$)$_3$
4-OCH(CH$_3$)$_3$
3-OC(CH$_3$)$_3$
4-OC(CH$_3$)$_3$
2-OCF$_3$
3-OCF$_3$
4-OCF$_3$
2-OCHF$_2$
3-OCHF$_2$
4-OCHF$_2$
2-OCF$_2$CHF$_2$
3-OCF$_2$CHF$_2$
4-OCF$_2$CHF$_2$
2-OH
3-OH
4-OH
2-NH$_2$
3-NH$_2$
4-NH$_2$
2-NH(CH$_3$)
3-NH(CH$_3$)
4-NH(CH$_3$)
2-N(CH$_3$)$_2$
3-N(CH$_3$)$_2$
4-N(CH$_3$)$_2$
2-SCH$_3$
3-SCH$_3$
4-SCH$_3$
2-SO$_2$CH$_3$
3-SO$_2$CH$_3$
4-SO$_2$CH$_3$
2-COCH$_3$
3-COCH$_3$
4-COCH$_3$
2-CO$_2$H
3-CO$_2$H

TABLE A-continued

| | |
|---|---|
| 4-$CO_2H$ | |
| 2-$CONH_2$ | |
| 3-$CONH_2$ | |
| 4-$CONH_2$ | |
| 2-$COOCH_3$ | |
| 3-$COOCH_3$ | |
| 4-$COOCH_3$ | |
| 2-$COOCH_2CH_3$ | |
| 3-$COOCH_2CH_3$ | |
| 4-$COOCH_2CH_3$ | |
| 2-$COOCH_2CH_2CH_3$ | |
| 3-$COOCH_2CH_2CH_3$ | |
| 4-$COOCH_2CH_2CH_3$ | |
| 2-$COOCH(CH_3)_3$ | |
| 3-$COOCH(CH_3)_3$ | |
| 4-$COOCH(CH_3)_3$ | |
| 3-$COOC(CH_3)_3$ | |
| 4-$COOC(CH_3)_3$ | |
| 2,3-[$OCH_2O$] | |
| 3,4-[$OCH_2O$] | |
| 2,3-[$OC(CH_3)_2O$] | |
| 3,4-[$OC(CH_3)_2O$] | |
| 2,3-[$OCH_2CH_2O$] | |
| 3,4-[$OCH_2CH_2O$] | |
| 2,3-[$OCF_2O$] | |
| 3,4-[$OCF_2O$] | |
| 2,3-[$CH_2$]$_4$ | |
| 3,4-[$CH_2$]$_4$ | |
| 2,3-[CH=CH—CH=CH] | |
| 3,4-[CH=CH—CH=CH] | |

$R^1 = H_3C-CR^c=NO-$

| $R^c$ |
|---|
| 1-naphthyl |
| 2-naphthyl |
| 2-pyridyl |
| 3-pyridyl |
| 4-pyridyl |
| 4-Cl-pyridin-2-yl |
| 5-Cl-pyridin-2-yl |
| 6-Cl-pyridin-2-yl |
| pyrimidin-5-yl |
| 6-$CH_3$-pyridin-3-yl |
| thien-2-yl |
| pyridazin-4-yl |
| 3-$CH_3$-pyrimidin-4-yl |
| 1,2,4-triazin-5-yl |
| 5-$CH_3$-pyrazin-2-yl |
| 6-$CF_3$-pyrimidin-4-yl |
| 5-Cl-thien-2-yl |
| 5-$CH_3$-thiazol-2-yl |
| $COCH_3$ |
| $COC_6H_5$ |
| 6-$CF_3$-pyrazin-2-yl |

$R^1 = R"ON=CR'-C(CH_3)=NO-$

| R' | R" |
|---|---|
| $CH_3$ | H |
| $CH_3$ | $CH_3$ |
| $CH_3$ | $C_2H_5$ |
| $CH_3$ | $CH_2CH_2CH_3$ |
| $CH_3$ | $CH(CH_3)_2$ |
| $CH_3$ | cyclopropyl |
| $CH_3$ | $(CH_2)_3CH_3$ |
| $CH_3$ | $CH(CH_3)CH_2CH_3$ |
| $CH_3$ | $CH_2CH(CH_3)_2$ |
| $CH_3$ | $C(CH_3)_3$ |
| $CH_3$ | $(CH_2)_4CH_3$ |
| $CH_3$ | $CH_2CH_2CH(CH_3)_2$ |
| $CH_3$ | $CH_2C(CH_3)_3$ |
| $CH_3$ | cyclopentyl |
| $CH_3$ | $(CH_2)_5CH_3$ |
| $CH_3$ | cyclohexyl |
| $CH_3$ | $(CH_2)_7CH_3$ |
| $CH_3$ | $CH_2CH_2OCH_3$ |
| $CH_3$ | $CH_2CH_2OCH_2CH_3$ |
| $CH_3$ | $CH_2CH(CH_3)OCH_3$ |
| $CH_3$ | $(CH_2)_3OCH_3$ |
| $CH_3$ | $CH_2CN$ |
| $CH_3$ | $CH_2CH_2CN$ |
| $CH_3$ | $CH_2CH_2CH_2CN$ |
| $CH_3$ | $CH_2CH=CH_2$ |
| $CH_3$ | $CH_2CH=CHCH_3$ |
| $CH_3$ | $CH_2CH=CHCl$ |
| $CH_3$ | $CH_2C\equiv CH$ |
| $CH_3$ | $CH_2C\equiv CCH_3$ |
| $CH_3$ | $CH_2CO_2H$ |
| $CH_3$ | $CH_2CO_2CH_3$ |
| $CH_3$ | $CH_2CONH_2$ |
| $CH_3$ | $CH_2CONHCH_3$ |
| $CH_3$ | $CH_2CON(CH_3)_2$ |
| $CH_3$ | $CH_2CH_2CO_2H$ |
| $CH_3$ | $CH_2CH_2CO_2CH_3$ |
| $CH_3$ | $CH_2CH_2CONH_2$ |
| $CH_3$ | $CH_2CH_2CONHCH_3$ |
| $CH_3$ | $CH_2CH_2CON(CH_3)_2$ |
| $CH_3$ | $CH_2CH_2NH_2$ |
| $CH_3$ | $CH_2CH_2CH_2NH_2$ |
| $CH_3$ | $CH_2CH_2CH_2CH_2NH_2$ |
| $CH_3$ | $CH_2CH_2NHCH_3$ |
| $CH_3$ | $CH_2CH_2CH_2NHCH_3$ |
| $CH_3$ | $CH_2CH_2CH_2CH_2NHCH_3$ |
| $CH_3$ | $CH_2CH_2N(CH_3)_2$ |
| $CH_3$ | $CH_2CH_2CH_2N(CH_3)_2$ |
| $CH_3$ | $CH_2CH_2CH_2CH_2N(CH_3)_2$ |
| $CH_3$ | $CH_2NO_2$ |
| $CH_3$ | $CH_2CH_2NO_2$ |
| $CH_3$ | $CH_2CH_2CH_2NO_2$ |
| $CH_3$ | $C(CH_3)=NOCH_3$ |
| $CH_3$ | $C(CH_3)=NOCH_2CH_3$ |
| $CH_3$ | $C(CH_2CH_3)=NOCH_3$ |
| $CH_3$ | $C(CH_2CH_3)=NOCH_2CH_3$ |
| $CH_3$ | $CH_2CH_2SCH_3$ |
| $CH_3$ | $CH_2CH_2SO_2CH_3$ |
| $C_6H_5$ | H |
| $C_6H_5$ | $CH_3$ |
| $C_6H_5$ | $C_2H_5$ |
| $C_6H_5$ | $CH_2CH_2CH_3$ |
| $C_6H_5$ | $CH(CH_3)_2$ |
| $C_6H_5$ | cyclopropyl |
| $C_6H_5$ | $(CH_2)_3CH_3$ |
| $C_6H_5$ | $CH(CH_3)CH_2CH_3$ |
| $C_6H_5$ | $CH_2CH(CH_3)_2$ |
| $C_6H_5$ | $C(CH_3)_3$ |
| $C_6H_5$ | $(CH_2)_4CH_3$ |
| $C_6H_5$ | $CH_2CH_2CH(CH_3)_2$ |
| $C_6H_5$ | $CH_2C(CH_3)_3$ |
| $C_6H_5$ | cyclopentyl |
| $C_6H_5$ | $(CH_2)_5CH_3$ |
| $C_6H_5$ | cyclohexyl |
| $C_6H_5$ | $(CH_2)_7CH_3$ |
| $C_6H_5$ | $CH_2CH_2OCH_3$ |
| $C_6H_5$ | $CH_2CH_2OCH_2CH_3$ |
| $C_6H_5$ | $CH_2CH(CH_3)OCH_3$ |
| $C_6H_5$ | $CH_2CH(CH_3)OCH_3$ |
| $C_6H_5$ | $(CH_2)_3OCH_3$ |
| $C_6H_5$ | $CH_2CN$ |
| $C_6H_5$ | $CH_2CH_2CN$ |
| $C_6H_5$ | $CH_2CH_2CH_2CN$ |
| $C_6H_5$ | $CH_2CH=CH_2$ |
| $C_6H_5$ | $CH_2CH=CHCH_3$ |
| $C_6H_5$ | $CH_2CH=CHCl$ |
| $C_6H_5$ | $CH_2C\equiv CH$ |
| $C_6H_5$ | $CH_2C\equiv CCH_3$ |
| $C_6H_5$ | $CH_2CO_2H$ |
| $C_6H_5$ | $CH_2CO_2CH_3$ |
| $C_6H_5$ | $CH_2CONH_2$ |
| $C_6H_5$ | $CH_2CONHCH_3$ |
| $C_6H_5$ | $CH_2CON(CH_3)_2$ |
| $C_6H_5$ | $CH_2CH_2CO_2N$ |

TABLE A-continued

| | |
|---|---|
| $C_6H_5$ | $CH_2CH_2CO_2CH_3$ |
| $C_6H_5$ | $CH_2CH_2CONH_2$ |
| $C_6H_5$ | $CH_2CH_2CONHCH_3$ |
| $C_6H_5$ | $CH_2CH_2CON(CH_3)_2$ |
| $C_6H_5$ | $CH_2CH_2NH_2$ |
| $C_6H_5$ | $CH_2CH_2CH_2NH_2$ |
| $C_6H_5$ | $CH_2CH_2CH_2CH_2NH_2$ |
| $C_6H_5$ | $CH_2CH_2NHCH_3$ |
| $C_6H_5$ | $CH_2CH_2CH_2NHCH_3$ |
| $C_6H_5$ | $CH_2CH_2CH_2CH_2NHCH_3$ |
| $C_6H_5$ | $CH_2CH_2N(CH_3)_2$ |
| $C_6H_5$ | $CH_2CH_2CH_2N(CH_3)_2$ |
| $C_6H_5$ | $CH_2CH_2CH_2CH_2N(CH_3)_2$ |
| $C_6H_5$ | $CH_2CSNH_2$ |
| $C_6H_5$ | $CH_2CH_2CSNH_2$ |
| $C_6H_5$ | $CH_2CH_2CH_2CSNH_2$ |
| $C_6H_5$ | $CH_2COCH_3$ |
| $C_6H_5$ | $CH_2CH_2COCH_3$ |
| $C_6H_5$ | $CH_2CH_2OCF_3$ |
| $C_6H_5$ | $CH_2CH_2CH_2OCF_3$ |
| $C_6H_5$ | $CH_2CH_2CH_2CH_2OCHF_2$ |
| $C_6H_5$ | $CH_2NO_2$ |
| $C_6H_5$ | $CH_2CH_2NO_2$ |
| $C_6H_5$ | $CH_2CH_2CH_2NO_2$ |
| $C_6H_5$ | $C(CH_3)=NOCH_3$ |
| $C_6H_5$ | $C(CH_3)=NOCH_2CH_3$ |
| $C_6H_5$ | $C(CH_2CH_3)=NOCH_3$ |
| $C_6H_5$ | $C(CH_2CH_3)=NOCH_2CH_3$ |
| $C_6H_5$ | $CH_2CH_2SCH_3$ |
| $C_6H_5$ | $CH_2CH_2SO_2CH_3$ |
| $4\text{-}Cl\text{-}C_6H_4$ | H |
| $4\text{-}Cl\text{-}C_6H_4$ | $CH_3$ |
| $4\text{-}Cl\text{-}C_6H_4$ | $C_2H_5$ |
| $4\text{-}Cl\text{-}C_6H_4$ | $CH_2CH_2CH_3$ |
| $4\text{-}Cl\text{-}C_6H_4$ | $CH(CH_3)_2$ |
| $4\text{-}Cl\text{-}C_6H_4$ | cyclopropyl |
| $4\text{-}Cl\text{-}C_6H_4$ | $(CH_2)_3CH_3$ |
| $4\text{-}Cl\text{-}C_6H_4$ | $CH(CH_3)CH_2CH_3$ |
| $4\text{-}Cl\text{-}C_6H_4$ | $CH_2CH(CH_3)_2$ |
| $4\text{-}Cl\text{-}C_6H_4$ | $C(CH_3)_3$ |
| $4\text{-}Cl\text{-}C_6H_4$ | $(CH_2)_4CH_3$ |
| $4\text{-}Cl\text{-}C_6H_4$ | $CH_2CH_2CH(CH_3)_2$ |
| $4\text{-}Cl\text{-}C_6H_4$ | $CH_2C(CH_3)_3$ |
| $4\text{-}Cl\text{-}C_6H_4$ | cyclopentyl |
| $4\text{-}Cl\text{-}C_6H_4$ | $(CH_2)_5CH_3$ |
| $4\text{-}Cl\text{-}C_6H_4$ | cyclohexyl |
| $4\text{-}Cl\text{-}C_6H_4$ | $(CH_2)_7CH_3$ |
| $4\text{-}Cl\text{-}C_6H_4$ | $CH_2CH_2OCH_3$ |
| $4\text{-}Cl\text{-}C_6H_4$ | $CH_2CH_2OCH_2CH_3$ |
| $4\text{-}Cl\text{-}C_6H_4$ | $CH_2CH(CH_3)OCH_3$ |
| $4\text{-}Cl\text{-}C_6H_4$ | $(CH_2)_3OCH_3$ |
| $4\text{-}Cl\text{-}C_6H_4$ | $CH_2CN$ |
| $4\text{-}Cl\text{-}C_6H_4$ | $CH_2CH_2CN$ |
| $4\text{-}Cl\text{-}C_6H_4$ | $CH_2CH_2CH_2CN$ |
| $4\text{-}Cl\text{-}C_6H_4$ | $CH_2CH=CH_2$ |
| $4\text{-}Cl\text{-}C_6H_4$ | $CH_2CH=CHCH_3$ |
| $4\text{-}Cl\text{-}C_6H_4$ | $CH_2CH=CHCl$ |
| $4\text{-}Cl\text{-}C_6H_4$ | $CH_2C\equiv CH$ |
| $4\text{-}Cl\text{-}C_6H_4$ | $CH_2C\equiv CCH_3$ |
| $4\text{-}Cl\text{-}C_6H_4$ | $CH_2CO_2H$ |
| $4\text{-}Cl\text{-}C_6H_4$ | $CH_2CO_2CH_3$ |
| $4\text{-}Cl\text{-}C_6H_4$ | $CH_2CONH_2$ |
| $4\text{-}Cl\text{-}C_6H_4$ | $CH_2CONHCH_3$ |
| $4\text{-}Cl\text{-}C_6H_4$ | $CH_2CON(CH_3)_2$ |
| $4\text{-}Cl\text{-}C_6H_4$ | $CH_2CH_2CO_2H$ |
| $4\text{-}Cl\text{-}C_6H_4$ | $CH_2CH_2CO_2CH_3$ |
| $4\text{-}Cl\text{-}C_6H_4$ | $CH_2CH_2CONH_2$ |
| $4\text{-}Cl\text{-}C_6H_4$ | $CH_2CH_2CONHCH_3$ |
| $4\text{-}Cl\text{-}C_6H_4$ | $CH_2CH_2CON(CH_3)_2$ |
| $4\text{-}Cl\text{-}C_6H_4$ | $CH_2CH_2NH_2$ |
| $4\text{-}Cl\text{-}C_6H_4$ | $CH_2CH_2CH_2NH_2$ |
| $4\text{-}Cl\text{-}C_6H_4$ | $CH_2CH_2NHCH_3$ |
| $4\text{-}Cl\text{-}C_6H_4$ | $CH_2CH_2CH_2NHCH_3$ |
| $4\text{-}Cl\text{-}C_6H_4$ | $CH_2CH_2CH_2CH_2NHCH_3$ |
| $4\text{-}Cl\text{-}C_6H_4$ | $CH_2CH_2N(CH_3)_2$ |
| $4\text{-}Cl\text{-}C_6H_4$ | $CH_2CH_2CH_2N(CH_3)_2$ |
| $4\text{-}Cl\text{-}C_6H_4$ | $CH_2CH_2CH_2CH_2N(CH_3)_2$ |
| $4\text{-}Cl\text{-}C_6H_4$ | $CH_2CSNH_2$ |
| $4\text{-}Cl\text{-}C_6H_4$ | $CH_2CH_2CSNH_2$ |
| $4\text{-}Cl\text{-}C_6H_4$ | $CH_2CH_2CH_2CSNH_2$ |
| $4\text{-}Cl\text{-}C_6H_4$ | $CH_2COCH_3$ |
| $4\text{-}Cl\text{-}C_6H_4$ | $CH_2CH_2COCH_3$ |
| $4\text{-}Cl\text{-}C_6H_4$ | $CH_2CH_2OCF_3$ |
| $4\text{-}Cl\text{-}C_6H_4$ | $CH_2CH_2CH_2OCF_3$ |
| $4\text{-}Cl\text{-}C_6H_4$ | $CH_2CH_2CH_2CH_2OCHF_2$ |
| $4\text{-}Cl\text{-}C_6H_4$ | $CH_2NO_2$ |
| $4\text{-}Cl\text{-}C_6H_4$ | $CH_2CH_2NO_2$ |
| $4\text{-}Cl\text{-}C_6H_4$ | $CH_2CH_2CH_2NO_2$ |
| $4\text{-}Cl\text{-}C_6H_4$ | $C(CH_3)=NOCH_3$ |
| $4\text{-}Cl\text{-}C_6H_4$ | $C(CH_3)=NOCH_2CH_3$ |
| $4\text{-}Cl\text{-}C_6H_4$ | $C(CH_2CH_3)=NOCH_3$ |
| $4\text{-}Cl\text{-}C_6H_4$ | $C(CH_2CH_3)=NOCH_2CH_3$ |
| $4\text{-}Cl\text{-}C_6H_4$ | $CH_2CH_2SCH_3$ |
| $4\text{-}Cl\text{-}C_6H_4$ | $CH_2CH_2SO_2CH_3$ |

$R^1 = V_x\text{-}$(phenyl)$\text{-}O\text{-}$

| $V_x$ |
|---|
| 2-F |
| 3-F |
| 4-F |
| 2,3-$F_2$ |
| 2,4-$F_2$ |
| 2,5-$F_2$ |
| 2,6-$F_2$ |
| 3,4-$F_2$ |
| 3,5-$F_2$ |
| 2-F, 5-$CH_3$ |
| 5-F, 2-$CH_3$ |
| 2-Cl |
| 3-Cl |
| 4-Cl |
| 2,3-$Cl_2$ |
| 2,4-$Cl_2$ |
| 2,5-$Cl_2$ |
| 2,6-$Cl_2$ |
| 3,4-$Cl_2$ |
| 3,5-$Cl_2$ |
| 2-$CH_3$ |
| 3-$CH_3$ |
| 4-$CH_3$ |
| 2,3-$(CH_3)_2$ |
| 2,4-$(CH_3)_2$ |
| 2,5-$(CH_3)_2$ |
| 2,6-$(CH_3)_2$ |
| 3,4-$(CH_3)_2$ |
| 3,5-$(CH_3)_2$ |
| 2-$NO_2$ |
| 3-$NO_2$ |
| 4-$NO_2$ |
| 2-CN |
| 3-CN |
| 4-CN |
| 2-$OCH_3$ |
| 3-$OCH_3$ |
| 4-$OCH_3$ |
| 2-$CF_3$ |
| 3-$CF_3$ |
| 4-$CF_3$ |
| 2-Cl, 4-$CH_3$ |
| 2-Cl, 5-$CH_3$ |
| 4-Cl, 2-$CH_3$ |
| 5-Cl, 2-$CH_3$ |
| 2-$COCH_3$ |
| 3-$COCH_3$ |
| 4-$COCH_3$ |
| 2-$COC_2H_5$ |
| 3-$COC_2H_5$ |
| 4-$COC_2H_5$ |
| 2-$CO(CH_2)_2CH_3$ |
| 3-$CO(CH_2)_2CH_3$ |

TABLE A-continued

4-CO(CH$_2$)$_2$CH$_3$
2-COCH(CH$_3$)$_2$
3-COCH(CH$_3$)$_2$
4-COCH(CH$_3$)$_2$
2-CH$_3$, 4-COCH$_3$
2-CH$_3$, 4-COC$_2$H$_5$
2-CH$_3$, 4-CO(CH$_2$)$_2$CH$_3$
2-CH$_3$, 4-COCH(CH$_3$)$_2$
2,5-(CH$_3$)$_2$, 4-COCH$_3$
2,5-(CH$_3$)$_2$, 4-COC$_2$H$_5$
2,5-(CH$_3$)$_2$, 4-CO(CH$_2$)$_2$CH$_3$
2,5-(CH$_3$)$_2$, 4-COCH(CH$_3$)$_2$
2-CH$_3$, 4-C(CH$_3$)=NOH
2-CH$_3$, 4-C(CH$_3$)=NOCH$_3$
2-CH$_3$, 4-C(CH$_3$)=NOC$_2$H$_5$
2-CH$_3$, 4-C(CH$_3$)=NO(CH$_2$)$_2$CH$_3$
2-CH$_3$, 4-C(CH$_3$)=NOCH(CH$_3$)$_2$
2-CH$_3$, 4-C(CH$_3$)=NO(CH$_2$)$_3$CH$_3$
2-CH$_3$, 4-C(CH$_3$)=NO(CH$_2$)$_4$CH$_3$
2-CH$_3$, 4-C(CH$_3$)=NO(CH$_2$)$_5$CH$_3$
2,5-(CH$_3$)$_2$, 4-C(CH$_3$)=NOH
2,5-(CH$_3$)$_2$, 4-C(CH$_3$)=NOCH$_3$
2,5-(CH$_3$)$_2$, 4-C(CH$_3$)=NOC$_2$H$_5$
2,5-(CH$_3$)$_2$, 4-C(CH$_3$)=NO(CH$_2$)$_2$CH$_3$
2,5-(CH$_3$)$_2$, 4-C(CH$_3$)=NOCH(CH$_3$)$_2$
2,5-(CH$_3$)$_2$, 4-C(CH$_3$)=NO(CH$_2$)$_3$CH$_3$
2,5-(CH$_3$)$_2$, 4-C(CH$_3$)=NO(CH$_2$)$_4$CH$_3$
2,5-(CH$_3$)$_2$, 4-C(CH$_3$)=NO(CH$_2$)$_5$CH$_3$

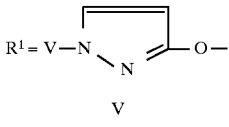

V 2-pyridinyl
3-pyridinyl
4-pyridinyl
5-Cl-2-pyridinyl
6-Cl-2-pyridinyl
3,5-Cl$_2$-2-pyridinyl
3,5-Cl$_2$-2-pyridinyl
3-Cl, 5-CF$_3$-2-pyridinyl
5-CF$_3$-2-pyridinyl
6-CF$_3$-2-pyridinyl
5-CH$_3$-2-pyridinyl
6-CH$_3$-2-pyridinyl
5-OCH$_3$-2-pyridinyl
6-OCH$_3$-2-pyridinyl
5-Cl-3-pyridinyl
6-Cl-3-pyridinyl
3,5-Cl$_2$-3-pyridinyl
3-Cl, 5-CF$_3$-3-pyridinyl
5-CF$_3$-3-pyridinyl
6-CF$_3$-3-pyridinyl
5-CH$_3$-3-pyridinyl
6-CH$_3$-3-pyridinyl
5-OCH$_3$-3-pyridinyl
6-OCH$_3$-3-pyridinyl
2-pyrimidinyl
4-pyrimidinyl
5-pyrimidinyl
5-Cl-2-pyrimidinyl
6-Cl-2-pyrimidinyl
4,6-Cl$_2$-2-pyrimidinyl
4-Cl, 6-CF$_3$-2-pyrimidinyl
6-CF$_3$-2-pyrimidinyl
4-CH$_3$-2-pyrimidinyl
6-CH$_3$-2-pyrimidinyl
4-OCH$_3$-2-pyrimidinyl
6-OCH$_3$-2-pyrimidinyl
3-pyridazinyl
2-Cl-3-pyridazinyl
6-Cl-3-pyridazinyl
2,6-Cl$_2$-3-pyridazinyl
2-Cl, 6-CF$_3$-3-pyridazinyl
2-CF$_3$-3-pyridazinyl
6-CF$_3$-3-pyridazinyl TABLE A-continued 2-CH$_3$-3-pyridazinyl
6-CH$_3$-3-pyridazinyl
2-OCH$_3$-3-pyridazinyl
6-OCH$_3$-3-pyridazinyl
2-pyrazinyl
2-oxazolyl
2-Cl-4-oxazolyl
5-cyclopropyl-3-isoxazolyl
2-CN-4-thiazolyl

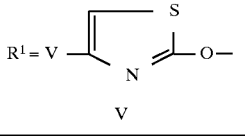

V 2-pyridinyl
3-pyridinyl
4-pyridinyl
5-Cl-2-pyridinyl
6-Cl-2-pyridinyl
3,5-Cl$_2$-2-pyridinyl
3-Cl, 5-CF$_3$-2-pyridinyl
4-CF$_3$-2-pyridinyl
5-CF$_3$-2-pyridinyl
6-CF$_3$-2-pyridinyl
5-CH$_3$-2-pyridinyl
6-CH$_3$-2-pyridinyl
5-OCH$_3$-2-pyridinyl
6-OCH$_3$-2-pyridinyl
5-Cl-3-pyridinyl
6-Cl-3-pyridinyl
3,5-Cl$_2$-3-pyridinyl
3-Cl, 5-CF$_3$-3-pyridinyl
5-CF$_3$-3-pyridinyl
6-CF$_3$-3-pyridinyl
5-CH$_3$-3-pyridinyl
6-CH$_3$-3-pyridinyl
5-OCH$_3$-3-pyridinyl
6-OCH$_3$-3-pyridinyl
2-pyrimidinyl
4-pyrimidinyl
5-pyrimidinyl
5-Cl-2-pyrimidinyl
6-Cl-2-pyrimidinyl
4,6-Cl$_2$-2-pyrimidinyl
4-Cl, 6-CF$_3$-2-pyrimidinyl
4-CF$_3$-2-pyrimidinyl
6-CF$_3$-2-pyrimidinyl
4-CH$_3$-2-pyrimidinyl
6-CH$_3$-2-pyrimidinyl
4-OCH$_3$-2-pyrimidinyl
6-OCH$_3$-2-pyrimidinyl
3-pyridazinyl
2-Cl-3-pyridazinyl
6-Cl-3-pyridazinyl
2-Cl, 6-CF$_3$-3-pyridazinyl
2-CF$_3$-3-pyridazinyl
6-CF$_3$-3-pyridazinyl
2-CH$_3$-3-pyridazinyl
6-CH$_3$-3-pyridazinyl
2-OCH$_3$-3-pyridazinyl
6-OCH$_3$-3-pyridazinyl
2-pyrazinyl
2-oxazolyl
2-Cl-4-oxazolyl
5-cyclopropyl-3-isoxazolyl
2-CN-4-thiazolyl 2-pyridinyl
3-pyridinyl TABLE A-continued 4-pyridinyl
5-Cl-2-pyridinyl
6-Cl-2-pyridinyl
3,5-Cl$_2$-2-pyridinyl
3-Cl, 5-CF$_3$-2-pyridinyl
5-CF$_3$-2-pyridinyl
6-CF$_3$-2-pyridinyl
5-CH$_3$-2-pyridinyl
6-CH$_3$-2-pyridinyl
5-OCH$_3$-2-pyridinyl
6-OCH$_3$-2-pyridinyl
5-Cl-3-pyridinyl
6-Cl-3-pyridinyl
3,5-Cl$_2$-3-pyridinyl
3-Cl, 5-CF$_3$-3-pyridinyl
5-CF$_3$-3-pyridinyl
6-CF$_3$-3-pyridinyl
5-CH$_3$-3-pyridinyl
6-CH$_3$-3-pyridinyl
5-OCH$_3$-3-pyridinyl
6-OCH$_3$-3-pyridinyl
2-pyrimidinyl
4-pyrimidinyl
5-pyrimidinyl
5-Cl-2-pyrimidinyl
6-Cl-2-pyrimidinyl
4,6-Cl$_2$-2-pyrimidinyl
4-Cl, 6-CF$_3$-2-pyrimidinyl
4-CF$_3$-2-pyrimidinyl
6-CF$_3$-2-pyrimidinyl
4-CH$_3$-2-pyrimidinyl
6-CH$_3$-2-pyrimidinyl
4-OCH$_3$-2-pyrimidinyl
6-OCH$_3$-2-pyrimidinyl
3-pyridazinyl
2-Cl-3-pyridazinyl
6-Cl-3-pyridazinyl
2,6-Cl$_2$-3-pyridazinyl
2-Cl, 6-CF$_3$-3-pyridazinyl
2-CF$_3$-3-pyridazinyl
6-CF$_3$-3-pyridazinyl
2-CH$_3$-3-pyridazinyl
6-CH$_3$-3-pyridazinyl
2-OCH$_3$-3-pyridazinyl
6-OCH$_3$-3-pyridazinyl
2-pyrazinyl
2-oxazolyl
2-Cl-4-oxazolyl
5-cyclopropyl-3-isoxazolyl
2-CN-4-thiaxolyl

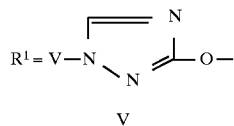

2-pyridinyl
3-pyridinyl
4-pyridinyl
5-Cl-2-pyridinyl
6-Cl-2-pyridinyl
3,5-Cl$_2$-2-pyridinyl
3-Cl, 5-CF$_3$-2-pyridinyl
5-CF$_3$-2-pyridinyl
6-CF$_3$-2-pyridinyl
5-CH$_3$-2-pyridinyl
6-CH$_3$-2-pyridinyl
5-OCH$_3$-2-pyridinyl
6-OCH$_3$-2-pyridinyl
5-Cl-3-pyridinyl
6-Cl-3-pyridinyl
3,5-Cl$_2$-3-pyridinyl
3-Cl, 5-CF$_3$-3-pyridinyl
5-CF$_3$-3-pyridinyl
6-CF$_3$-3-pyridinyl
5-CH$_3$-3-pyridinyl
6-CH$_3$-3-pyridinyl TABLE A-continued 5-OCH$_3$-3-pyridinyl
6-OCH$_3$-3-pyridinyl
2-pyrimidinyl
4-pyrimidinyl
5-pyrimidinyl
5-Cl-2-pyrimidinyl
6-Cl-2-pyrimidinyl
4,6-Cl$_2$-2-pyrimidinyl
4-Cl, 6-CF$_3$-2-pyrimidinyl
4-CF$_3$-2-pyrimidinyl
6-CF$_3$-2-pyrimidinyl
4-CH$_3$-2-pyrimidinyl
6-CH$_3$-2-pyrimidinyl
4-OCH$_3$-2-pyrimidinyl
6-OCH$_3$-2-pyrimidinyl
3-pyridazinyl
2-Cl-3-pyridazinyl
6-Cl-3-pyridazinyl
2,6-Cl$_2$-3-pyridazinyl
2-Cl, 6-CF$_3$-3-pyridazinyl
2-CF$_3$-3-pyridazinyl
6-CF$_3$-3-pyridazinyl
2-CH$_3$-3-pyridazinyl
6-CH$_3$-3-pyridazinyl
2-OCH$_3$-3-pyridazinyl
6-OCH$_3$-3-pyridazinyl
2-pyrazinyl
2-oxazolyl
2-Cl-4-oxazolyl
5-cyclopropyl-3-isoxazolyl
2-CN-4-thiazolyl

| $R^1 = R''ON = CR' - C(R''') = NO-$ | | |
|---|---|---|
| R''' | R'' | R' |
| CH$_3$ | CH$_3$ | 2-F—C$_6$H$_4$ |
| CH$_3$ | CH$_3$ | 3-F—C$_6$H$_4$ |
| CH$_3$ | CH$_3$ | 4-F—C$_6$H$_4$ |
| CH$_3$ | CH$_3$ | 2,3-F$_2$—C$_6$H$_3$ |
| CH$_3$ | CH$_3$ | 2,4-F$_2$—C$_6$H$_3$ |
| CH$_3$ | CH$_3$ | 2,5-F$_2$—C$_6$H$_3$ |
| CH$_3$ | CH$_3$ | 2,6-F$_2$—C$_6$H$_3$ |
| CH$_3$ | CH$_3$ | 3,4-F$_2$—C$_6$H$_3$ |
| CH$_3$ | CH$_3$ | 3,5-F$_2$—C$_6$H$_3$ |
| CH$_3$ | CH$_3$ | 2-Cl—C$_6$H$_4$ |
| CH$_3$ | CH$_3$ | 3-Cl—C$_6$H$_4$ |
| CH$_3$ | CH$_3$ | 4-Cl—C$_6$H$_4$ |
| CH$_3$ | CH$_3$ | 2,3-Cl$_2$—C$_6$H$_3$ |
| CH$_3$ | CH$_3$ | 2,4-Cl$_2$—C$_6$H$_3$ |
| CH$_3$ | CH$_3$ | 2,5-Cl$_2$—C$_6$H$_3$ |
| CH$_3$ | CH$_3$ | 2,6-Cl$_2$—C$_6$H$_3$ |
| CH$_3$ | CH$_3$ | 3,4-Cl$_2$—C$_6$H$_3$ |
| CH$_3$ | CH$_3$ | 3,5-Cl$_2$—C$_6$H$_3$ |
| CH$_3$ | CH$_3$ | 2,3,4-Cl$_3$—C$_6$H$_2$ |
| CH$_3$ | CH$_3$ | 2,3,5-Cl$_3$—C$_6$H$_2$ |
| CH$_3$ | CH$_3$ | 2,3,6-Cl$_3$—C$_6$H$_2$ |
| CH$_3$ | CH$_3$ | 2,4,5-Cl$_3$—C$_6$H$_2$ |
| CH$_3$ | CH$_3$ | 2,4,6-Cl$_3$—C$_6$H$_2$ |
| CH$_3$ | CH$_3$ | 3,4,5-Cl$_3$—C$_6$H$_2$ |
| CH$_3$ | CH$_3$ | 2-Br—C$_6$H$_4$ |
| CH$_3$ | CH$_3$ | 3-Br—C$_6$H$_4$ |
| CH$_3$ | CH$_3$ | 4-Br—C$_6$H$_4$ |
| CH$_3$ | CH$_3$ | 2,3-Br$_2$—C$_6$H$_3$ |
| CH$_3$ | CH$_3$ | 2,4-Br$_2$—C$_6$H$_3$ |
| CH$_3$ | CH$_3$ | 2,5-Br$_2$—C$_6$H$_3$ |
| CH$_3$ | CH$_3$ | 2,6-Br$_2$—C$_6$H$_3$ |
| CH$_3$ | CH$_3$ | 3,4-Br$_2$—C$_6$H$_3$ |
| CH$_3$ | CH$_3$ | 3,5-Br$_2$—C$_6$H$_3$ |
| CH$_3$ | CH$_3$ | 2-F, 3-Cl—C$_6$H$_3$ |
| CH$_3$ | CH$_3$ | 2-F, 4-Cl—C$_6$H$_3$ |
| CH$_3$ | CH$_3$ | 2-F, 5-Cl—C$_6$H$_3$ |
| CH$_3$ | CH$_3$ | 2-F, 3-Br—C$_6$H$_3$ |
| CH$_3$ | CH$_3$ | 2-F, 4-Br—C$_6$H$_3$ |
| CH$_3$ | CH$_3$ | 2-F, 5-Br—C$_6$H$_3$ |
| CH$_3$ | CH$_3$ | 2-Cl, 3-Br—C$_6$H$_3$ |
| CH$_3$ | CH$_3$ | 2-Cl, 4-Br—C$_6$H$_3$ |
| CH$_3$ | CH$_3$ | 2-Cl, 5-Br—C$_6$H$_3$ |
| CH$_3$ | CH$_3$ | 3-F, 4-Cl—C$_6$H$_3$ |

TABLE A-continued

| | | |
|---|---|---|
| CH$_3$ | CH$_3$ | 3-F, 5-Cl—C$_6$H$_3$ |
| CH$_3$ | CH$_3$ | 3-F, 6-Cl—C$_6$H$_3$ |
| CH$_3$ | CH$_3$ | 3-F, 4-Br—C$_6$H$_3$ |
| CH$_3$ | CH$_3$ | 3-F, 5-Br—C$_6$H$_3$ |
| CH$_3$ | CH$_3$ | 3-F, 6-Br—C$_6$H$_3$ |
| CH$_3$ | CH$_3$ | 3-Cl, 4-Br—C$_6$H$_3$ |
| CH$_3$ | CH$_3$ | 3-Cl, 5-Br—C$_6$H$_3$ |
| CH$_3$ | CH$_3$ | 3-Cl, 6-Br—C$_6$H$_3$ |
| CH$_3$ | CH$_3$ | 4-F, 5-Cl—C$_6$H$_3$ |
| CH$_3$ | CH$_3$ | 4-F, 6-Cl—C$_6$H$_3$ |
| CH$_3$ | CH$_3$ | 4-F, 5-Br—C$_6$H$_3$ |
| CH$_3$ | CH$_3$ | 4-F, 6-Br—C$_6$H$_3$ |
| CH$_3$ | CH$_3$ | 4-Cl, 5-Br—C$_6$H$_3$ |
| CH$_3$ | CH$_3$ | 5-F, 6-Cl—C$_6$H$_3$ |
| CH$_3$ | CH$_3$ | 5-F, 6-Br—C$_6$H$_3$ |
| CH$_3$ | CH$_3$ | 5-Cl, 6-Br—C$_6$H$_3$ |
| CH$_3$ | CH$_3$ | 3-Br, 4-Cl, 5-Br—C$_6$H$_2$ |
| CH$_3$ | CH$_3$ | 2-CN—C$_6$H$_4$ |
| CH$_3$ | CH$_3$ | 3-CN—C$_6$H$_4$ |
| CH$_3$ | CH$_3$ | 4-CN—C$_6$H$_4$ |
| CH$_3$ | CH$_3$ | 2-NO$_2$—C$_6$H$_4$ |
| CH$_3$ | CH$_3$ | 3-NO$_2$—C$_6$H$_4$ |
| CH$_3$ | CH$_3$ | 4-NO$_2$—C$_6$H$_4$ |
| CH$_3$ | CH$_3$ | 2-CH$_3$—C$_6$H$_4$ |
| CH$_3$ | CH$_3$ | 3-CH$_3$—C$_6$H$_4$ |
| CH$_3$ | CH$_3$ | 4-CH$_3$—C$_6$H$_4$ |
| CH$_3$ | CH$_3$ | 2,3-(CH$_3$)$_2$—C$_6$H$_3$ |
| CH$_3$ | CH$_3$ | 2,4-(CH$_3$)$_2$—C$_6$H$_3$ |
| CH$_3$ | CH$_3$ | 2,5-(CH$_3$)$_2$—C$_6$H$_3$ |
| CH$_3$ | CH$_3$ | 2,6-(CH$_3$)$_2$—C$_6$H$_3$ |
| CH$_3$ | CH$_3$ | 3,4-(CH$_3$)$_2$—C$_6$H$_3$ |
| CH$_3$ | CH$_3$ | 3,5-(CH$_3$)$_2$—C$_6$H$_3$ |
| CH$_3$ | CH$_3$ | 2-C$_2$H$_5$—C$_6$H$_4$ |
| CH$_3$ | CH$_3$ | 3-C$_2$H$_5$—C$_6$H$_4$ |
| CH$_3$ | CH$_3$ | 4-C$_2$H$_5$—C$_6$H$_4$ |
| CH$_3$ | CH$_3$ | 2-i-C$_3$H$_7$—C$_6$H$_4$ |
| CH$_3$ | CH$_3$ | 3-i-C$_3$H$_7$—C$_6$H$_4$ |
| CH$_3$ | CH$_3$ | 4-i-C$_3$H$_7$—C$_6$H$_4$ |
| CH$_3$ | CH$_3$ | 3-tert.-C$_6$H$_4$—C$_6$H$_4$ |
| CH$_3$ | CH$_3$ | 4-tert.-C$_6$H$_4$—C$_6$H$_4$ |
| CH$_3$ | CH$_3$ | 2-Vinyl-C$_6$H$_4$ |
| CH$_3$ | CH$_3$ | 3-Vinyl-C$_6$H$_4$ |
| CH$_3$ | CH$_3$ | 4-Vinyl-C$_6$H$_4$ |
| CH$_3$ | CH$_3$ | 2-Allyl-C$_6$H$_4$ |
| CH$_3$ | CH$_3$ | 3-Allyl-C$_6$H$_4$ |
| CH$_3$ | CH$_3$ | 4-Allyl-C$_6$H$_4$ |
| CH$_3$ | CH$_3$ | 2-C$_6$H$_5$—C$_6$H$_4$ |
| CH$_3$ | CH$_3$ | 3-C$_6$H$_5$—C$_6$H$_4$ |
| CH$_3$ | CH$_3$ | 4-C$_6$H$_5$—C$_6$H$_4$ |
| CH$_3$ | CH$_3$ | 3-CH$_3$, 5-t-C$_4$H$_9$—C$_6$H$_3$ |
| CH$_3$ | CH$_3$ | 2-OH—C$_6$H$_4$ |
| CH$_3$ | CH$_3$ | 3-OH—C$_6$H$_4$ |
| CH$_3$ | CH$_3$ | 4-OH—C$_6$H$_4$ |
| CH$_3$ | CH$_3$ | 2-OCH$_3$—C$_6$H$_4$ |
| CH$_3$ | CH$_3$ | 3-OCH$_3$—C$_6$H$_4$ |
| CH$_3$ | CH$_3$ | 4-OCH$_3$—C$_6$H$_4$ |
| CH$_3$ | CH$_3$ | 2,3-(OCH$_3$)$_2$—C$_6$H$_3$ |
| CH$_3$ | CH$_3$ | 2,4-(OCH$_3$)$_2$—C$_6$H$_3$ |
| CH$_3$ | CH$_3$ | 2,5-(OCH$_3$)$_2$—C$_6$H$_3$ |
| CH$_3$ | CH$_3$ | 3,4-(OCH$_3$)$_2$—C$_6$H$_3$ |
| CH$_3$ | CH$_3$ | 3,5-(OCH$_3$)$_2$—C$_6$H$_3$ |
| CH$_3$ | CH$_3$ | 3,4,5-(OCH$_3$)$_3$—C$_6$H$_2$ |
| CH$_3$ | CH$_3$ | 2-OC$_2$H$_5$—C$_6$H$_4$ |
| CH$_3$ | CH$_3$ | 3-OC$_2$H$_5$—C$_6$H$_4$ |
| CH$_3$ | CH$_3$ | 4-OC$_2$H$_5$—C$_6$H$_4$ |
| CH$_3$ | CH$_3$ | 2-O-(n-C$_3$H$_7$)—C$_6$H$_4$ |
| CH$_3$ | CH$_3$ | 3-O-(n-C$_3$H$_7$)—C$_6$H$_4$ |
| CH$_3$ | CH$_3$ | 4-O-(n-C$_3$H$_7$)—C$_6$H$_4$ |
| CH$_3$ | CH$_3$ | 2-O-(i-C$_3$H$_7$)—C$_6$H$_4$ |
| CH$_3$ | CH$_3$ | 3-O-(i-C$_3$H$_7$)—C$_6$H$_4$ |
| CH$_3$ | CH$_3$ | 4-O-(i-C$_3$H$_7$)—C$_6$H$_4$ |
| CH$_3$ | CH$_3$ | 4-O-(n-C$_4$H$_9$)—C$_6$H$_4$ |
| CH$_3$ | CH$_3$ | 3-O-(t-C$_4$H$_9$)—C$_6$H$_4$ |
| CH$_3$ | CH$_3$ | 4-O-(t-C$_4$H$_9$)—C$_6$H$_4$ |
| CH$_3$ | CH$_3$ | 2-O-Allyl-C$_6$H$_4$ |
| CH$_3$ | CH$_3$ | 3-O-Allyl-C$_6$H$_4$ |
| CH$_3$ | CH$_3$ | 4-O-Allyl-C$_6$H$_4$ |
| CH$_3$ | CH$_3$ | 2-CF$_3$—C$_6$H$_4$ |
| CH$_3$ | CH$_3$ | 3-CF$_3$—C$_6$H$_4$ |
| CH$_3$ | CH$_3$ | 4-CF$_3$—C$_6$H$_4$ |
| CH$_3$ | CH$_3$ | 2-Acetyl-C$_6$H$_4$ |
| CH$_3$ | CH$_3$ | 3-Acetyl-C$_6$H$_4$ |
| CH$_3$ | CH$_3$ | 4-Acetyl-C$_6$H$_4$ |
| CH$_3$ | CH$_3$ | 2-Methoxycarbonyl-C$_6$H$_4$ |
| CH$_3$ | CH$_3$ | 3-Methoxycarbonyl-C$_6$H$_4$ |
| CH$_3$ | CH$_3$ | 4-Methoxycarbonyl-C$_6$H$_4$ |
| CH$_3$ | CH$_3$ | 2-Aminocarbonyl-C$_6$H$_4$ |
| CH$_3$ | CH$_3$ | 3-Aminocarbonyl-C$_6$H$_4$ |
| CH$_3$ | CH$_3$ | 4-Aminocarbonyl-C$_6$H$_4$ |
| CH$_3$ | CH$_3$ | 2-Dimethylaminocarbonyl-C$_6$H$_4$ |
| CH$_3$ | CH$_3$ | 3-Dimethylaminocarbonyl-C$_6$H$_4$ |
| CH$_3$ | CH$_3$ | 4-Dimethylaminocarbonyl-C$_6$H$_4$ |
| CH$_3$ | CH$_3$ | 2-(N-Methylaminocarbonyl)-C$_6$H$_4$ |
| CH$_3$ | CH$_3$ | 3-(N-Methylaminocarbonyl)-C$_6$H$_4$ |
| CH$_3$ | CH$_3$ | 4-(N-Methylaminocarbonyl)-C$_6$H$_4$ |
| CH$_3$ | CH$_3$ | 2-H$_2$N—C$_6$H$_4$ |
| CH$_3$ | CH$_3$ | 3-H$_2$N—C$_6$H$_4$ |
| CH$_3$ | CH$_3$ | 4-H$_2$N—C$_6$H$_4$ |
| CH$_3$ | CH$_3$ | 2-Aminothiocarbonyl-C$_6$H$_4$ |
| CH$_3$ | CH$_3$ | 3-Aminothiocarbonyl-C$_6$H$_4$ |
| CH$_3$ | CH$_3$ | 4-Aminothiocarbonyl-C$_6$H$_4$ |
| CH$_3$ | CH$_3$ | 2-Methoxyiminomethyl-C$_6$H$_4$ |
| CH$_3$ | CH$_3$ | 3-Methoxyiminomethyl-C$_6$H$_4$ |
| CH$_3$ | CH$_3$ | 4-Methoxyiminomethyl-C$_6$H$_4$ |
| CH$_3$ | CH$_3$ | 2-Formyl-C$_6$H$_4$ |
| CH$_3$ | CH$_3$ | 3-Formyl-C$_6$H$_4$ |
| CH$_3$ | CH$_3$ | 4-Formyl-C$_6$H$_4$ |
| CH$_3$ | CH$_3$ | 2-(1'-Methoxyiminoeth-1'-yl)-C$_6$H$_4$ |
| CH$_3$ | CH$_3$ | 3-(1'-Methoxyiminoeth-1'-yl)-C$_6$H$_4$ |
| CH$_3$ | CH$_3$ | 4-(1'-Methoxyiminoeth-1'-yl)-C$_6$H$_4$ |
| CH$_3$ | CH$_3$ | 2-SCH$_3$—C$_6$H$_4$ |
| CH$_3$ | CH$_3$ | 3-SCH$_3$—C$_6$H$_4$ |
| CH$_3$ | CH$_3$ | 4-SCH$_3$—C$_6$H$_4$ |
| CH$_3$ | CH$_3$ | 2-SO$_2$CH$_3$—C$_6$H$_4$ |
| CH$_3$ | CH$_3$ | 3-SO$_2$CH$_3$—C$_6$H$_4$ |
| CH$_3$ | CH$_3$ | 4-SO$_2$CH$_3$—C$_6$H$_4$ |
| CH$_3$ | CH$_3$ | 2-OCF$_3$—C$_6$H$_4$ |
| CH$_3$ | CH$_3$ | 3-OCF$_3$—C$_6$H$_4$ |
| CH$_3$ | CH$_3$ | 4-OCF$_3$—C$_6$H$_4$ |
| CH$_3$ | CH$_3$ | 2-OCHF$_2$—C$_6$H$_4$ |
| CH$_3$ | CH$_3$ | 3-OCHF$_2$—C$_6$H$_4$ |
| CH$_3$ | CH$_3$ | 4-OCHF$_2$—C$_6$H$_4$ |
| CH$_3$ | CH$_3$ | 3-CF$_3$, 4-OCF$_3$—C$_6$H$_3$ |
| CH$_3$ | CH$_3$ | 2-NHCH$_3$—C$_6$H$_4$ |
| CH$_3$ | CH$_3$ | 3-NHCH$_3$—C$_6$H$_4$ |
| CH$_3$ | CH$_3$ | 4-NHCH$_3$—C$_6$H$_4$ |
| CH$_3$ | CH$_3$ | 2-N(CH$_3$)$_2$—C$_6$H$_4$ |
| CH$_3$ | CH$_3$ | 3-N(CH$_3$)$_2$—C$_6$H$_4$ |
| CH$_3$ | CH$_3$ | 4-N(CH$_3$)$_2$—C$_6$H$_4$ |
| CH$_3$ | CH$_3$ | 2-Ethoxycarbonyl-C$_6$H$_4$ |
| CH$_3$ | CH$_3$ | 3-Ethoxycarbonyl-C$_6$H$_4$ |
| CH$_3$ | CH$_3$ | 4-Ethoxycarbonyl-C$_6$H$_4$ |
| CH$_3$ | CH$_3$ | 2-CH$_2$CH$_2$F—C$_6$H$_4$ |
| CH$_3$ | CH$_3$ | 3-CH$_2$CH$_2$F—C$_6$H$_4$ |
| CH$_3$ | CH$_3$ | 4-CH$_2$CH$_2$F—C$_6$H$_4$ |
| CH$_3$ | CH$_3$ | 2-CH$_2$CF$_3$—C$_6$H$_4$ |
| CH$_3$ | CH$_3$ | 3-CH$_2$CF$_3$—C$_6$H$_4$ |
| CH$_3$ | CH$_3$ | 4-CH$_2$CF$_3$—C$_6$H$_4$ |
| CH$_3$ | CH$_3$ | 2-CF$_2$CHF$_2$—C$_6$H$_4$ |
| CH$_3$ | CH$_3$ | 3-CF$_2$CHF$_2$—C$_6$H$_4$ |
| CH$_3$ | CH$_3$ | 4-CF$_2$CHF$_2$—C$_6$H$_4$ |
| CH$_3$ | CH$_3$ | 2-CHF$_2$—C$_6$H$_4$ |
| CH$_3$ | CH$_3$ | 3-CHF$_2$—C$_6$H$_4$ |
| CH$_3$ | CH$_3$ | 4-CHF$_2$—C$_6$H$_4$ |
| CH$_3$ | CH$_3$ | 2-(1'-Oxo-n-prop-1-yl)-C$_6$H$_4$ |
| CH$_3$ | CH$_3$ | 3-(1'-Oxo-n-prop-1-yl)-C$_6$H$_4$ |
| CH$_3$ | CH$_3$ | 4-(1'-Oxo-n-prop-1-yl)-C$_6$H$_4$ |
| CH$_3$ | CH$_3$ | 2-(1'-Oxo-iso-prop-1-yl)-C$_6$H$_4$ |
| CH$_3$ | CH$_3$ | 3-(1'-Oxo-iso-prop-1-yl)-C$_6$H$_4$ |
| CH$_3$ | CH$_3$ | 4-(1'-Oxo-iso-prop-1-yl)-C$_6$H$_4$ |
| CH$_3$ | CH$_3$ | Cyclopropyl |
| CH$_3$ | CH$_3$ | Cyclopentyl |
| CH$_3$ | CH$_3$ | Cyclohexyl |
| CH$_3$ | CH$_3$ | 1-Naphthyl |
| CH$_3$ | CH$_3$ | 2-Naphthyl |
| CH$_3$ | CH$_3$ | 2-Pyridyl |
| CH$_3$ | CH$_3$ | 3-Pyridyl |
| CH$_3$ | CH$_3$ | 4-Pyridyl |

TABLE A-continued

| | | |
|---|---|---|
| CH₃ | CH₃ | 5-CH₃-Pyridin-2-yl |
| CH₃ | CH₃ | 5-Cl-Pyridin-2-yl |
| CH₃ | CH₃ | 6-Cl-Pyridin-2-yl |
| CH₃ | CH₃ | 3,5-Cl₂-Pyridin-2-yl |
| CH₃ | CH₃ | 6-OCH₃-Pyridin-2-yl |
| CH₃ | CH₃ | 6-CH₃-Pyridin-2-yl |
| CH₃ | CH₃ | 6-Cl-Pyridin-3-yl |
| CH₃ | CH₃ | 6-CH₃-Pyridin-3-yl |
| CH₃ | CH₃ | 6-OCH₃-Pyridin-3-yl |
| CH₃ | CH₃ | 2-Pyrimidinyl |
| CH₃ | CH₃ | 4-OCH₃-Pyrimidin-2-yl |
| CH₃ | CH₃ | 4-OC₂H₅-Pyrimidin-2-yl |
| CH₃ | CH₃ | 4-Cl-Pyrimidin-2-yl |
| CH₃ | CH₃ | 4-CH₃-Pyrimidin-2-yl |
| CH₃ | CH₃ | 5-CH₃-Pyrimidin-2-yl |
| CH₃ | CH₃ | 5-Cl-Pyrimidin-2-yl |
| CH₃ | CH₃ | 5-OCH₃-Pyrimidin-2-yl |
| CH₃ | CH₃ | 5-OC₂H₅-Pyrimidin-2-yl |
| CH₃ | CH₃ | 4-Pyrimidinyl |
| CH₃ | CH₃ | 2-Cl-Pyrimidin-4-yl |
| CH₃ | CH₃ | 2-OCH₃-Pyrimidin-4-yl |
| CH₃ | CH₃ | 2-CH₃-Pyrimidin-4-yl |
| CH₃ | CH₃ | 6-Cl-Pyrimidin-4-yl |
| CH₃ | CH₃ | 6-CH₃-Pyrimidin-4-yl |
| CH₃ | CH₃ | 6-OCH₃-Pyrimidin-4-yl |
| CH₃ | CH₃ | 5-Pyrimidinyl |
| CH₃ | CH₃ | 2-CH₃-Pyrimidin-5-yl |
| CH₃ | CH₃ | 2-Cl-Pyrimidin-5-yl |
| CH₃ | CH₃ | 2-OCH₃-Pyrimidin-5-yl |
| CH₃ | CH₃ | 2-OC₂H₅-Pyrimidin-5-yl |
| CH₃ | CH₃ | 2-Furyl |
| CH₃ | CH₃ | 4-C₂H₅-Fur-2-yl |
| CH₃ | CH₃ | 4-CH₃-Fur-2-yl |
| CH₃ | CH₃ | 4-Cl-Fur-2-yl |
| CH₃ | CH₃ | 4-CN-Fur-2-yl |
| CH₃ | CH₃ | 5-CH₃-Fur-2-yl |
| CH₃ | CH₃ | 5-Cl-Fur-2-yl |
| CH₃ | CH₃ | 6-CN-Fur-2-yl |
| CH₃ | CH₃ | 3-Furyl |
| CH₃ | CH₃ | 5-CH₃-Fur-3-yl |
| CH₃ | CH₃ | 5-Cl-Fur-3-yl |
| CH₃ | CH₃ | 5-CN-Fur-3-yl |
| CH₃ | CH₃ | 2-Thienyl |
| CH₃ | CH₃ | 4-CH₃-Thien-2-yl |
| CH₃ | CH₃ | 4-Cl-Thien-2-yl |
| CH₃ | CH₃ | 4-CN-Thien-2-yl |
| CH₃ | CH₃ | 5-CH₃-Thien-2-yl |
| CH₃ | CH₃ | 5-Cl-Thien-2-yl |
| CH₃ | CH₃ | 5-CN-Thien-2-yl |
| CH₃ | CH₃ | 3-Thienyl |
| CH₃ | CH₃ | 5-CH₃-Thien-3-yl |
| CH₃ | CH₃ | 5-Cl-Thien-3-yl |
| CH₃ | CH₃ | 5-CN-Thien-3-yl |
| CH₃ | CH₃ | 1-Methylpropyl-2-yl |
| CH₃ | CH₃ | 1-Methylpropyl-3-yl |
| CH₃ | CH₃ | 2-Oxazolyl |
| CH₃ | CH₃ | 4-CH₃-Oxazol-2-yl |
| CH₃ | CH₃ | 4-Cl-Oxazol-2-yl |
| CH₃ | CH₃ | 4-CN-Oxazol-2-yl |
| CH₃ | CH₃ | 5-CH₃-Oxazol-2-yl |
| CH₃ | CH₃ | 5-Cl-Oxazol-2-yl |
| CH₃ | CH₃ | 5-CN-Oxazol-2-yl |
| CH₃ | CH₃ | 4-Oxazolyl |
| CH₃ | CH₃ | 2-CH₃-Oxazol-4-yl |
| CH₃ | CH₃ | 2-Cl-Oxazol-4-yl |
| CH₃ | CH₃ | 2-CN-Oxazol-4-yl |
| CH₃ | CH₃ | 5-Oxazolyl |
| CH₃ | CH₃ | 2-CH₃-Oxazol-5-yl |
| CH₃ | CH₃ | 2-Cl-Oxazol-5-yl |
| CH₃ | CH₃ | 2-CN-Oxazol-5-yl |
| CH₃ | CH₃ | 3-Isoxazolyl |
| CH₃ | CH₃ | 5-CH₃-Isoxazol-3-yl |
| CH₃ | CH₃ | 5-Cl-Isoxazol-3-yl |
| CH₃ | CH₃ | 5-CN-Isoxazol-3-yl |
| CH₃ | CH₃ | 5-Isoxazolyl |
| CH₃ | CH₃ | 3-CH₃-Isoxazol-5-yl |
| CH₃ | CH₃ | 3-Cl-Isoxazol-5-yl |
| CH₃ | CH₃ | 3-CN-Isoxazol-5-yl |
| CH₃ | CH₃ | 2-Thiazolyl |
| CH₃ | CH₃ | 4-CH₃-Thiazol-2-yl |
| CH₃ | CH₃ | 4-Cl-Thiazol-2-yl |
| CH₃ | CH₃ | 4-CN-Thiazol-2-yl |
| CH₃ | CH₃ | 5-CH₃-Thiazol-2-yl |
| CH₃ | CH₃ | 5-Cl-Thiazol-2-yl |
| CH₃ | CH₃ | 5-CN-Thiazol-2-yl |
| CH₃ | CH₃ | 4-Thiazolyl |
| CH₃ | CH₃ | 2-CH₃-Thiazol-4-yl |
| CH₃ | CH₃ | 2-Cl-Thiazol-4-yl |
| CH₃ | CH₃ | 2-CN-Thiazol-4-yl |
| CH₃ | CH₃ | 2-SCH₃-Thiazol-4-yl |
| CH₃ | CH₃ | 5-Thiazolyl |
| CH₃ | CH₃ | 2-CH₃-Thiazol-5-yl |
| CH₃ | CH₃ | 2-Cl-Thiazol-5-yl |
| CH₃ | CH₃ | 2-CN-Thiazol-5-yl |
| CH₃ | CH₃ | 3-Isothiazolyl |
| CH₃ | CH₃ | 5-CH₃-Isothiazol-3-yl |
| CH₃ | CH₃ | 5-Cl-Isothiazol-3-yl |
| CH₃ | CH₃ | 5-CN-Isothiazol-3-yl |
| CH₃ | CH₃ | 5-Isothiazolyl |
| CH₃ | CH₃ | 3-CH₃-Isothiazol-5-yl |
| CH₃ | CH₃ | 3-Cl-Isothiazol-5-yl |
| CH₃ | CH₃ | 3-CN-Isothiazol-5-yl |
| CH₃ | CH₃ | 2-Imidazolyl |
| CH₃ | CH₃ | 4-CH₃-Imidazol-2-yl |
| CH₃ | CH₃ | 4-Cl-Imidazol-2-yl |
| CH₃ | CH₃ | 4-CN-Imidazol-2-yl |
| CH₃ | CH₃ | 1-CH₃-Imidazol-2-yl |
| CH₃ | CH₃ | 1-CH₃, 4-Cl-Imidazol-2-yl |
| CH₃ | CH₃ | 1,4-(CH₃)₂-Imidazol-2-yl |
| CH₃ | CH₃ | 1-CH₃, 5-Cl-Imidazol-2-yl |
| CH₃ | CH₃ | 1,5-(CH₃)₂-Imidazol-2-yl |
| CH₃ | CH₃ | 4-Imidazolyl |
| CH₃ | CH₃ | 2-CH₃-Imidazol-4-yl |
| CH₃ | CH₃ | 2-Cl-Imidazol-4-yl |
| CH₃ | CH₃ | 1-CH₃-Imidazol-4-yl |
| CH₃ | CH₃ | 1,2-(CH₃)₂-Imidazol-4-yl |
| CH₃ | CH₃ | 1-CH₃, 2-Cl-Imidazol-4-yl |
| CH₃ | CH₃ | 1-CH₃-Imidazol-5-yl |
| CH₃ | CH₃ | 1-CH₃, 3-Cl-Imidazol-5-yl |
| CH₃ | CH₃ | 1,2-(CH₃)₂-Imidazol-5-yl |
| CH₃ | CH₃ | 3-Pyrazolyl |
| CH₃ | CH₃ | 5-CH₃-Pyrazol-3-yl |
| CH₃ | CH₃ | 5-Cl-Pyrazol-3-yl |
| CH₃ | CH₃ | 5-CN-Pyrazol-3-yl |
| CH₃ | CH₃ | 1-CH₃-Pyrazol-3-yl |
| CH₃ | CH₃ | 1-CH₃, 4-Cl-Pyrazol-3-yl |
| CH₃ | CH₃ | 1-CH₃, 5-Cl-Pyrazol-3-yl |
| CH₃ | CH₃ | 1,5-(CH₃)₂-Pyrazol-3-yl |
| CH₃ | CH₃ | 1-CH₃-Pyrazol-5-yl |
| CH₃ | CH₃ | 1-CH₃, 3-Cl-Pyrazol-5-yl |
| CH₃ | CH₃ | 1,3-(CH₃)₂-Pyrazol-5-yl |
| CH₃ | CH₃ | 4-Pyrazolyl |
| CH₃ | CH₃ | 3-Cl-Pyrazol-4-yl |
| CH₃ | CH₃ | 3-CH₃-Pyrazol-4-yl |
| CH₃ | CH₃ | 1-CH₃-Pyrazol-4-yl |
| CH₃ | CH₃ | 1-CH₃, 3-Cl-Pyrazol-4-yl |
| CH₃ | CH₃ | 1,3-(CH₃)₂-Pyrazol-4-yl |
| CH₃ | CH₃ | 1,3,4-Oxadizol-5-yl |
| CH₃ | CH₃ | 2-CH₃-1,3,4-Oxadiazol-5-yl |
| CH₃ | CH₃ | 2-Cl-1,3,4-Oxadiazol-5-yl |
| CH₃ | CH₃ | 2-CF₃-1,3,4-Oxadiazol-5-yl |
| CH₃ | CH₃ | 2-i-C₃H₇-1,3,4-Oxadiazol-5-yl |
| CH₃ | CH₃ | 2-OCH₃-1,3,4-Oxadiazol-5-yl |
| CH₃ | CH₃ | 1,2,4-Oxadiazol-3-yl |
| CH₃ | CH₃ | 5-CH₃-1,2,4-Oxadiazol-3-yl |
| CH₃ | CH₃ | 5-i-C₃H₇-1,2,4-Oxadiazol-3-yl |
| CH₃ | CH₃ | 5-Cl-1,2,4-Oxadiazol-3-yl |
| CH₃ | CH₃ | 5-CF₃-1,2,4-Oxadiazol-3-yl |
| CH₃ | CH₃ | 1,2,4-Triazol-3-yl |
| CH₃ | CH₃ | 1-CH₃-1,2,4-Triazol-3-yl |
| CH₃ | CH₃ | 1-Pyrrolyl |
| CH₃ | CH₃ | 3-CH₃-Pyrrol-1-yl |
| CH₃ | CH₃ | 1-Pyrazolyl |
| CH₃ | CH₃ | 3-CH₃-Pyrazol-1-yl |
| CH₃ | CH₃ | 3-CF₃-Pyrazol-1-yl |
| CH₃ | CH₃ | 4-CH₃-Pyrazol-1-yl |
| CH₃ | CH₃ | 4-Cl-Pyrazol-1-yl |
| CH₃ | CH₃ | 4-Ethoxycarbonyl-Pyrazol-1-yl |

TABLE A-continued

| | | |
|---|---|---|
| CH₃ | CH₃ | 3-CH₃, 4-Br-Pyrazol-1-yl |
| CH₃ | CH₃ | 1-Imidazolyl |
| CH₃ | CH₃ | 4-CH₃-Imidazol-1-yl |
| CH₃ | CH₃ | 4,5-Cl₂-Imidazol-1-yl |
| CH₃ | CH₃ | 2,4-(CH₃)₂-Imidazol-1-yl |
| CH₃ | CH₃ | 1,2,4-Triazol-1-yl |
| CH₃ | CH₃ | 1,3,4-Triazol-1-yl |
| CH₃ | CH₃ | 3,5-(CH₃)₂-1,2,4-Triazol-1-yl |
| CH₃ | CH₃ | 1-Piperidinyl |
| CH₃ | CH₃ | 1-Pyrrolidinyl |
| CH₃ | CH₃ | 1-Morpholinyl |
| H | CH₃ | CH₃ |
| F | CH₃ | CH₃ |
| Cl | CH₃ | CH₃ |
| Br | CH₃ | CH₃ |
| C₂H₅ | CH₃ | CH₃ |
| CN | CH₃ | CH₃ |
| NO₂ | CH₃ | CH₃ |
| OCH₃ | CH₃ | CH₃ |
| SCH₃ | CH₃ | CH₃ |
| NH₂ | CH₃ | CH₃ |
| NH(CH₃) | CH₃ | CH₃ |
| N(CH₃)₂ | CH₃ | CH₃ |
| OH | CH₃ | CH₃ |
| CF₃ | CH₃ | CH₃ |
| OCF₃ | CH₃ | CH₃ |
| H | CH₃ | C₆H₅ |
| F | CH₃ | C₆H₅ |
| Cl | CH₃ | C₆H₅ |
| Br | CH₃ | C₆H₅ |
| C₂H₅ | CH₃ | C₆H₅ |
| CN | CH₃ | C₆H₅ |
| NO₂ | CH₃ | C₆H₅ |
| OCH₃ | CH₃ | C₆H₅ |
| OCH₃ | CH₃ | C₆H₅ |
| SCH₃ | CH₃ | C₆H₅ |
| NH₂ | CH₃ | C₆H₅ |
| NH(CH₃) | CH₃ | C₆H₅ |
| NH(CH₃)₂ | CH₃ | C₆H₅ |
| OH | CH₃ | C₆H₅ |
| CF₃ | CH₃ | C₆H₅ |
| OCF₃ | CH₃ | C₆H₅ |
| CH₃ | CH₃ | H |
| CH₃ | CH₃ | C₂H₅ |
| CH₃ | CH₃ | n-C₃H₇ |
| CH₃ | CH₃ | iso-C₃H₇ |
| CH₃ | CH₃ | tert-C₄H₉ |
| CH₃ | CH₃ | CN |
| CH₃ | CH₃ | NO₂ |
| CH₃ | CH₃ | OCH₃ |
| CH₃ | CH₃ | OC₂H₅ |
| CH₃ | CH₃ | O-n-C₃H₇ |
| CH₃ | CH₃ | O-Benzyl |
| CH₃ | CH₃ | SCH₃ |
| CH₃ | CH₃ | SC₂H₅ |
| CH₃ | CH₃ | S-n-C₃H₇ |
| CH₃ | CH₃ | S-iso-C₃H₇ |
| CH₃ | CH₃ | NH₂ |
| CH₃ | CH₃ | NH(CH₃) |
| CH₃ | CH₃ | N(CH₃)₂ |
| CH₃ | CH₃ | OH |
| CH₃ | CH₃ | CF₃ |
| CH₃ | CH₃ | OCF₃ |
| OCH₃ | CH₃ | OCH₃ |
| CF₃ | CH₃ | CF₃ |
| SCH₃ | CH₃ | CN |
| OH | CH₃ | OH |
| OCH₃ | C₂H₅ | CH₃ |
| OCH₃ | n-C₃H₇ | CH₃ |
| OCH₃ | iso-C₃H₇ | CH₃ |
| OCH₃ | C₂H₅ | C₆H₅ |
| OCH₃ | n-C₃H₇ | C₆H₅ |
| OCH₃ | iso-C₃H₇ | C₆H₅ |
| CH₃ | CH₃ | F |
| CH₃ | CH₃ | Cl |
| CH₃ | CH₃ | Br |
| CH₃ | CH₃ | S(C₆H₅) |
| CH₃ | C₂H₅ | C₂H₅ |
| CH₃ | C₂H₅ | n-C₃H₇ |
| CH₃ | C₂H₅ | iso-C₃H₇ |
| CH₃ | C₂H₅ | tert-C₄H₉ |
| OCH₃ | CH₃ | 2-F—C₆H₄ |
| OCH₃ | CH₃ | 3-F—C₆H₄ |
| OCH₃ | CH₃ | 4-F—C₆H₄ |
| OCH₃ | CH₃ | 2,3-F₂—C₆H₃ |
| OCH₃ | CH₃ | 2,4-F₂—C₆H₃ |
| OCH₃ | CH₃ | 2,5-F₂—C₆H₃ |
| OCH₃ | CH₃ | 2,6-F₂—C₆H₃ |
| OCH₃ | CH₃ | 3,4-F₂—C₆H₃ |
| OCH₃ | CH₃ | 3,5-F₂—C₆H₃ |
| OCH₃ | CH₃ | 2-Cl—C₆H₄ |
| OCH₃ | CH₃ | 3-Cl—C₆H₄ |
| OCH₃ | CH₃ | 4-Cl—C₆H₄ |
| OCH₃ | CH₃ | 2,3-Cl₂—C₆H₃ |
| OCH₃ | CH₃ | 2,4-Cl₂—C₆H₃ |
| OCH₃ | CH₃ | 2,5-Cl₂—C₆H₃ |
| OCH₃ | CH₃ | 2,6-Cl₂—C₆H₃ |
| OCH₃ | CH₃ | 3,4-Cl₂—C₆H₃ |
| OCH₃ | CH₃ | 3,5-Cl₂—C₆H₃ |
| OCH₃ | CH₃ | 2,3,4-Cl₃—C₆H₂ |
| OCH₃ | CH₃ | 2,3,5-Cl₃—C₆H₂ |
| OCH₃ | CH₃ | 2,3,6-Cl₃—C₆H₂ |
| OCH₃ | CH₃ | 2,4,5-Cl₃—C₆H₂ |
| OCH₃ | CH₃ | 2,4,6-Cl₃—C₆H₂ |
| OCH₃ | CH₃ | 3,4,5-Cl₃—C₆H₂ |
| OCH₃ | CH₃ | 2-Br—C₆H₄ |
| OCH₃ | CH₃ | 3-Br—C₆H₄ |
| OCH₃ | CH₃ | 4-Br—C₆H₄ |
| OCH₃ | CH₃ | 2,3-Br₂—C₆H₃ |
| OCH₃ | CH₃ | 2,4-Br₂—C₆H₃ |
| OCH₃ | CH₃ | 2,5-Br₂—C₆H₃ |
| OCH₃ | CH₃ | 2,6-Br₂—C₆H₃ |
| OCH₃ | CH₃ | 3,4-Br₂—C₆H₃ |
| OCH₃ | CH₃ | 3,5-Br₂—C₆H₃ |
| OCH₃ | CH₃ | 2-F, 3-Cl—C₆H₃ |
| OCH₃ | CH₃ | 2-F, 4-Cl—C₆H₃ |
| OCH₃ | CH₃ | 2-F, 5-Cl—C₆H₃ |
| OCH₃ | CH₃ | 2-F, 3-Br—C₆H₃ |
| OCH₃ | CH₃ | 2-F, 4-Br—C₆H₃ |
| OCH₃ | CH₃ | 2-F, 5-Br—C₆H₃ |
| OCH₃ | CH₃ | 2-Cl, 3-Br—C₆H₃ |
| OCH₃ | CH₃ | 2-Cl, 4-Br—C₆H₃ |
| OCH₃ | CH₃ | 2-Cl, 5-Br—C₆H₃ |
| OCH₃ | CH₃ | 3-F, 4-Cl—C₆H₃ |
| OCH₃ | CH₃ | 3-F, 5-Cl—C₆H₃ |
| OCH₃ | CH₃ | 3-F, 6-Cl—C₆H₃ |
| OCH₃ | CH₃ | 3-F, 4-Br—C₆H₃ |
| OCH₃ | CH₃ | 3-F, 5-Br—C₆H₃ |
| OCH₃ | CH₃ | 3-F, 6-Br—C₆H₃ |
| OCH₃ | CH₃ | 3-Cl, 4-Br—C₆H₃ |
| OCH₃ | CH₃ | 3-Cl, 5-Br—C₆H₃ |
| OCH₃ | CH₃ | 3-Cl, 6-Br—C₆H₃ |
| OCH₃ | CH₃ | 4-F, 5-Cl—C₆H₃ |
| OCH₃ | CH₃ | 4-F, 6-Cl—C₆H₃ |
| OCH₃ | CH₃ | 4-F, 5-Br—C₆H₃ |
| OCH₃ | CH₃ | 4-F, 6-Br—C₆H₃ |
| OCH₃ | CH₃ | 4-Cl, 5-Br—C₆H₃ |
| OCH₃ | CH₃ | 5-F, 6-Cl—C₆H₃ |
| OCH₃ | CH₃ | 5-F, 6-Br—C₆H₃ |
| OCH₃ | CH₃ | 5-Cl, 6-Br—C₆H₃ |
| OCH₃ | CH₃ | 3-Br, 4-Cl, 5-Br—C₆H₂ |
| OCH₃ | CH₃ | 2-CN—C₆H₄ |
| OCH₃ | CH₃ | 3-CN—C₆H₄ |
| OCH₃ | CH₃ | 4-CN—C₆H₄ |
| OCH₃ | CH₃ | 2-NO₂—C₆H₄ |
| OCH₃ | CH₃ | 3-NO₂—C₆H₄ |
| OCH₃ | CH₃ | 4-NO₂—C₆H₄ |
| OCH₃ | CH₃ | 2-CH₃—C₆H₄ |
| OCH₃ | CH₃ | 3-CH₃—C₆H₄ |
| OCH₃ | CH₃ | 4-CH₃—C₆H₄ |
| OCH₃ | CH₃ | 2,3-(CH₃)₂—C₆H₃ |
| OCH₃ | CH₃ | 2,4-(CH₃)₂—C₆H₃ |
| OCH₃ | CH₃ | 2,5-(CH₃)₂—C₆H₃ |
| OCH₃ | CH₃ | 2,6-(CH₃)₂—C₆H₃ |
| OCH₃ | CH₃ | 3,4-(CH₃)₂—C₆H₃ |
| OCH₃ | CH₃ | 3,5-(CH₃)₂—C₆H₃ |
| OCH₃ | CH₃ | 2-C₂H₅—C₆H₄ |
| OCH₃ | CH₃ | 3-C₂H₅—C₆H₄ |

TABLE A-continued

| | | |
|---|---|---|
| OCH$_3$ | CH$_3$ | 4-C$_2$H$_5$—C$_6$H$_4$ |
| OCH$_3$ | CH$_3$ | 2-i-C$_3$H$_7$—C$_6$H$_4$ |
| OCH$_3$ | CH$_3$ | 3-i-C$_3$H$_7$—C$_6$H$_4$ |
| OCH$_3$ | CH$_3$ | 4-i-C$_3$H$_7$—C$_6$H$_4$ |
| OCH$_3$ | CH$_3$ | 3-tert.-C$_4$H$_9$—C$_6$H$_4$ |
| OCH$_3$ | CH$_3$ | 4-tert.-C$_4$H$_9$—C$_6$H$_4$ |
| OCH$_3$ | CH$_3$ | 2-Vinyl-C$_6$H$_4$ |
| OCH$_3$ | CH$_3$ | 3-Vinyl-C$_6$H$_4$ |
| OCH$_3$ | CH$_3$ | 4-Vinyl-C$_6$H$_4$ |
| OCH$_3$ | CH$_3$ | 2-Allyl-C$_6$H$_4$ |
| OCH$_3$ | CH$_3$ | 3-Allyl-C$_6$H$_4$ |
| OCH$_3$ | CH$_3$ | 4-Allyl-C$_6$H$_4$ |
| OCH$_3$ | CH$_3$ | 2-C$_6$H$_5$—C$_6$H$_4$ |
| OCH$_3$ | CH$_3$ | 3-C$_6$H$_5$—C$_6$H$_4$ |
| OCH$_3$ | CH$_3$ | 4-C$_6$H$_5$—C$_6$H$_4$ |
| OCH$_3$ | CH$_3$ | 3-CH$_3$, 5-t-C$_4$H$_9$—C$_6$H$_3$ |
| OCH$_3$ | CH$_3$ | 2-OH—C$_6$H$_4$ |
| OCH$_3$ | CH$_3$ | 3-OH—C$_6$H$_4$ |
| OCH$_3$ | CH$_3$ | 4-OH—C$_6$H$_4$ |
| OCH$_3$ | CH$_3$ | 2-OCH$_3$—C$_6$H$_4$ |
| OCH$_3$ | CH$_3$ | 3-OCH$_3$—C$_6$H$_4$ |
| OCH$_3$ | CH$_3$ | 4-OCH$_3$—C$_6$H$_4$ |
| OCH$_3$ | CH$_3$ | 2,3-(OCH$_3$)$_2$—C$_6$H$_3$ |
| OCH$_3$ | CH$_3$ | 2,4-(OCH$_3$)$_2$—C$_6$H$_3$ |
| OCH$_3$ | CH$_3$ | 2,5-(OCH$_3$)$_2$—C$_6$H$_3$ |
| OCH$_3$ | CH$_3$ | 3,4-(OCH$_3$)$_2$—C$_6$H$_3$ |
| OCH$_3$ | CH$_3$ | 3,5-(OCH$_3$)$_2$—C$_6$H$_3$ |
| OCH$_3$ | CH$_3$ | 3,4,5-(OCH$_3$)$_3$—C$_6$H$_2$ |
| OCH$_3$ | CH$_3$ | 2-OC$_2$H$_5$—C$_6$H$_4$ |
| OCH$_3$ | CH$_3$ | 3-OC$_2$H$_5$—C$_6$H$_4$ |
| OCH$_3$ | CH$_3$ | 4-OC$_2$H$_5$—C$_6$H$_4$ |
| OCH$_3$ | CH$_3$ | 2-O-(n-C$_3$H$_7$)—C$_6$H$_4$ |
| OCH$_3$ | CH$_3$ | 3-O-(n-C$_3$H$_7$)—C$_6$H$_4$ |
| OCH$_3$ | CH$_3$ | 4-O-(n-C$_3$H$_7$)—C$_6$H$_4$ |
| OCH$_3$ | CH$_3$ | 2-O-(i-C$_3$H$_7$)—C$_6$H$_4$ |
| OCH$_3$ | CH$_3$ | 3-O-(i-C$_3$H$_7$)—C$_6$H$_4$ |
| OCH$_3$ | CH$_3$ | 4-O-(i-C$_3$H$_7$)—C$_6$H$_4$ |
| OCH$_3$ | CH$_3$ | 4-O-(n-C$_4$H$_9$)—C$_6$H$_4$ |
| OCH$_3$ | CH$_3$ | 3-O-(t-C$_4$H$_9$)—C$_6$H$_4$ |
| OCH$_3$ | CH$_3$ | 4-O-(n-C$_6$H$_{13}$)—C$_6$H$_4$ |
| OCH$_3$ | CH$_3$ | 2-O-Allyl-C$_6$H$_4$ |
| OCH$_3$ | CH$_3$ | 3-O-Allyl-C$_6$H$_4$ |
| OCH$_3$ | CH$_3$ | 4-O-Allyl-C$_6$H$_4$ |
| OCH$_3$ | CH$_3$ | 2-CF$_3$—C$_6$H$_4$ |
| OCH$_3$ | CH$_3$ | 3-CF$_3$—C$_6$H$_4$ |
| OCH$_3$ | CH$_3$ | 4-CF$_3$—C$_6$H$_4$ |
| OCH$_3$ | CH$_3$ | 2-Acetyl-C$_6$H$_4$ |
| OCH$_3$ | CH$_3$ | 3-Acetyl-C$_6$H$_4$ |
| OCH$_3$ | CH$_3$ | 4-Acetyl-C$_6$H$_4$ |
| OCH$_3$ | CH$_3$ | 2-Methoxycarbonyl-C$_6$H$_4$ |
| OCH$_3$ | CH$_3$ | 3-Methoxycarbonyl-C$_6$H$_4$ |
| OCH$_3$ | CH$_3$ | 4-Methoxycarbonyl-C$_6$H$_4$ |
| OCH$_3$ | CH$_3$ | 2-Aminocarbonyl-C$_6$H$_4$ |
| OCH$_3$ | CH$_3$ | 3-Aminocarbonyl-C$_6$H$_4$ |
| OCH$_3$ | CH$_3$ | 4-Aminocarbonyl-C$_6$H$_4$ |
| OCH$_3$ | CH$_3$ | 2-Dimethylaminocarbonyl-C$_6$H$_4$ |
| OCH$_3$ | CH$_3$ | 3-Dimethylaminocarbonyl-C$_6$H$_4$ |
| OCH$_3$ | CH$_3$ | 4-Dimethylaminocarbonyl-C$_6$H$_4$ |
| OCH$_3$ | CH$_3$ | 2-(N-Methylaminocarbonyl)-C$_6$H$_4$ |
| OCH$_3$ | CH$_3$ | 3-(N-Methylaminocarbonyl)-C$_6$H$_4$ |
| OCH$_3$ | CH$_3$ | 4-(N-Methylaminocarbonyl)-C$_6$H$_4$ |
| OCH$_3$ | CH$_3$ | 2-H$_2$N—C$_6$H$_4$ |
| OCH$_3$ | CH$_3$ | 3-H$_2$N—C$_6$H$_4$ |
| OCH$_3$ | CH$_3$ | 4-H$_2$N—C$_6$H$_4$ |
| OCH$_3$ | CH$_3$ | 2-Aminothiocarbonyl-C$_6$H$_4$ |
| OCH$_3$ | CH$_3$ | 3-Aminothiocarbonyl-C$_6$H$_4$ |
| OCH$_3$ | CH$_3$ | 4-Aminothiocarbonyl-C$_6$H$_4$ |
| OCH$_3$ | CH$_3$ | 2-Methoxyiminomethyl-C$_6$H$_4$ |
| OCH$_3$ | CH$_3$ | 3-Methoxyiminomethyl-C$_6$H$_4$ |
| OCH$_3$ | CH$_3$ | 4-Methoxyiminomethyl-C$_6$H$_4$ |
| OCH$_3$ | CH$_3$ | 2-Formyl-C$_6$H$_4$ |
| OCH$_3$ | CH$_3$ | 3-Formyl-C$_6$H$_4$ |
| OCH$_3$ | CH$_3$ | 4-Formyl-C$_6$H$_4$ |
| OCH$_3$ | CH$_3$ | 2-(1'-Methoxyiminoeth-1'-yl)-C$_6$H$_4$ |
| OCH$_3$ | CH$_3$ | 3-(1'-Methoxyiminoeth-1'-yl)-C$_6$H$_4$ |
| OCH$_3$ | CH$_3$ | 4-(1'-Methoxyiminoeth-1'-yl)-C$_6$H$_4$ |
| OCH$_3$ | CH$_3$ | 2-SCH$_3$—C$_6$H$_4$ |
| OCH$_3$ | CH$_3$ | 3-SCH$_3$—C$_6$H$_4$ |
| OCH$_3$ | CH$_3$ | 4-SCH$_3$—C$_6$H$_4$ |

TABLE A-continued

| | | |
|---|---|---|
| OCH$_3$ | CH$_3$ | 2-SO$_2$CH$_3$—C$_6$H$_4$ |
| OCH$_3$ | CH$_3$ | 3-SO$_2$CH$_3$—C$_6$H$_4$ |
| OCH$_3$ | CH$_3$ | 4-SO$_2$CH$_3$—C$_6$H$_4$ |
| OCH$_3$ | CH$_3$ | 2-OCF$_3$—C$_6$H$_4$ |
| OCH$_3$ | CH$_3$ | 3-OCF$_3$—C$_6$H$_4$ |
| OCH$_3$ | CH$_3$ | 4-OCF$_3$—C$_6$H$_4$ |
| OCH$_3$ | CH$_3$ | 2-OCHF$_2$—C$_6$H$_4$ |
| OCH$_3$ | CH$_3$ | 3-OCHF$_2$—C$_6$H$_4$ |
| OCH$_3$ | CH$_3$ | 4-OCHF$_2$—C$_6$H$_4$ |
| OCH$_3$ | CH$_3$ | 3-CF$_3$, 4-OCF$_3$—C$_6$H$_3$ |
| OCH$_3$ | CH$_3$ | 2-NHCH$_3$—C$_6$H$_4$ |
| OCH$_3$ | CH$_3$ | 3-NHCH$_3$—C$_6$H$_4$ |
| OCH$_3$ | CH$_3$ | 4-NHCH$_3$—C$_6$H$_4$ |
| OCH$_3$ | CH$_3$ | 2-N(CH$_3$)$_2$—C$_6$H$_4$ |
| OCH$_3$ | CH$_3$ | 3-N(CH$_3$)$_2$—C$_6$H$_4$ |
| OCH$_3$ | CH$_3$ | 4-N(CH$_3$)$_2$—C$_6$H$_4$ |
| OCH$_3$ | CH$_3$ | 2-Ethoxycarbonyl-C$_6$H$_4$ |
| OCH$_3$ | CH$_3$ | 3-Ethoxycarbonyl-C$_6$H$_4$ |
| OCH$_3$ | CH$_3$ | 4-Ethoxycarbonyl-C$_6$H$_4$ |
| OCH$_3$ | CH$_3$ | 2-CH$_2$CH$_2$F—C$_6$H$_4$ |
| OCH$_3$ | CH$_3$ | 3-CH$_2$CH$_2$F—C$_6$H$_4$ |
| OCH$_3$ | CH$_3$ | 4-CH$_2$CH$_2$F—C$_6$H$_4$ |
| OCH$_3$ | CH$_3$ | 2-CH$_2$CF$_3$—C$_6$H$_4$ |
| OCH$_3$ | CH$_3$ | 3-CH$_2$CF$_3$—C$_6$H$_4$ |
| OCH$_3$ | CH$_3$ | 4-CH$_2$CF$_3$—C$_6$H$_4$ |
| OCH$_3$ | CH$_3$ | 2-CF$_2$CHF$_2$—C$_6$H$_4$ |
| OCH$_3$ | CH$_3$ | 3-CF$_2$CHF$_2$—C$_6$H$_4$ |
| OCH$_3$ | CH$_3$ | 4-CF$_2$CHF$_2$—C$_6$H$_4$ |
| OCH$_3$ | CH$_3$ | 2-CHF$_2$—C$_6$H$_4$ |
| OCH$_3$ | CH$_3$ | 3-CHF$_2$—C$_6$H$_4$ |
| OCH$_3$ | CH$_3$ | 4-CHF$_2$—C$_6$H$_4$ |
| OCH$_3$ | CH$_3$ | 2-(1'-Oxo-n-prop-1-yl)-C$_6$H$_4$ |
| OCH$_3$ | CH$_3$ | 3-(1'-Oxo-n-prop-1-yl)-C$_6$H$_4$ |
| OCH$_3$ | CH$_3$ | 4-(1'-Oxo-n-prop-1-yl)-C$_6$H$_4$ |
| OCH$_3$ | CH$_3$ | 2-(1'-Oxo-iso-prop-1-yl)-C$_6$H$_4$ |
| OCH$_3$ | CH$_3$ | 3-(1'-Oxo-iso-prop-1-yl)-C$_6$H$_4$ |
| OCH$_3$ | CH$_3$ | 4-(1'-Oxo-iso-prop-1-yl)-C$_6$H$_4$ |
| OCH$_3$ | CH$_3$ | Cyclopropyl |
| OCH$_3$ | CH$_3$ | Cyclopentyl |
| OCH$_3$ | CH$_3$ | Cyclohexyl |
| OCH$_3$ | CH$_3$ | 1-Naphthyl |
| OCH$_3$ | CH$_3$ | 2-Naphthyl |
| OCH$_3$ | CH$_3$ | 2-Pyridyl |
| OCH$_3$ | CH$_3$ | 3-Pyridyl |
| OCH$_3$ | CH$_3$ | 4-Pyridyl |
| OCH$_3$ | CH$_3$ | 5-CH$_3$-Pyridin-2-yl |
| OCH$_3$ | CH$_3$ | 5-Cl-Pyridin-2-yl |
| OCH$_3$ | CH$_3$ | 6-Cl-Pyridin-2-yl |
| OCH$_3$ | CH$_3$ | 3,5-Cl$_2$-Pyridin-2-yl |
| OCH$_3$ | CH$_3$ | 6-OCH$_3$-Pyridin-2-yl |
| OCH$_3$ | CH$_3$ | 6-CH$_3$-Pyridin-2-yl |
| OCH$_3$ | CH$_3$ | 6-Cl-Pyridin-3-yl |
| OCH$_3$ | CH$_3$ | 6-CH$_3$-Pyridin-3-yl |
| OCH$_3$ | CH$_3$ | 6-OCH$_3$-Pyridin-3-yl |
| OCH$_3$ | CH$_3$ | 2-Pyrimidinyl |
| OCH$_3$ | CH$_3$ | 4-OCH$_3$-Pyrimidin-2-yl |
| OCH$_3$ | CH$_3$ | 4-OC$_2$H$_5$-Pyrimidin-2-yl |
| OCH$_3$ | CH$_3$ | 4-Cl-Pyrimidin-2-yl |
| OCH$_3$ | CH$_3$ | 4-CH$_3$-Pyrimidin-2-yl |
| OCH$_3$ | CH$_3$ | 5-CH$_3$-Pyrimidin-2-yl |
| OCH$_3$ | CH$_3$ | 5-Cl-Pyrimidin-2-yl |
| OCH$_3$ | CH$_3$ | 5-OCH$_3$-Pyrimidin-2-yl |
| OCH$_3$ | CH$_3$ | 5-OC$_2$H$_5$-Pyrimidin-2-yl |
| OCH$_3$ | CH$_3$ | 4-Pyrimidinyl |
| OCH$_3$ | CH$_3$ | 2-Cl-Pyrimidin-4-yl |
| OCH$_3$ | CH$_3$ | 2-OCH$_3$-Pyrimidin-4-yl |
| OCH$_3$ | CH$_3$ | 2-CH$_3$-Pyrimidin-4-yl |
| OCH$_3$ | CH$_3$ | 6-Cl-Pyrimidin-4-yl |
| OCH$_3$ | CH$_3$ | 6-CH$_3$-Pyrimidin-4-yl |
| OCH$_3$ | CH$_3$ | 6-OCH$_3$-Pyrimidin-4-yl |
| OCH$_3$ | CH$_3$ | 5-Pyrimidinyl |
| OCH$_3$ | CH$_3$ | 2-CH$_3$-Pyrimidin-5-yl |
| OCH$_3$ | CH$_3$ | 2-Cl-Pyrimidin-5-yl |
| OCH$_3$ | CH$_3$ | 2-OCH$_3$-Pyrimidin-5-yl |
| OCH$_3$ | CH$_3$ | 2-OC$_2$H$_5$-Pyrimidin-5-yl |
| OCH$_3$ | CH$_3$ | 2-Furyl |
| OCH$_3$ | CH$_3$ | 4-C$_2$H$_5$-Fur-2-yl |
| OCH$_3$ | CH$_3$ | 4-CH$_3$-Fur-2-yl |
| OCH$_3$ | CH$_3$ | 4-Cl-Fur-2-yl |

TABLE A-continued

| | | |
|---|---|---|
| OCH$_3$ | CH$_3$ | 4-CN-Fur-2-yl |
| OCH$_3$ | CH$_3$ | 5-CH$_3$-Fur-2-yl |
| OCH$_3$ | CH$_3$ | 5-Cl-Fur-2-yl |
| OCH$_3$ | CH$_3$ | 5-CN-Fur-2-yl |
| OCH$_3$ | CH$_3$ | 3-Furyl |
| OCH$_3$ | CH$_3$ | 5-CH$_3$-Fur-3-yl |
| OCH$_3$ | CH$_3$ | 5-Cl-Fur-3-yl |
| OCH$_3$ | CH$_3$ | 5-CN-Fur-3-yl |
| OCH$_3$ | CH$_3$ | 2-Thienyl |
| OCH$_3$ | CH$_3$ | 4-CH$_3$-Thien-2-yl |
| OCH$_3$ | CH$_3$ | 4-Cl-Thien-2-yl |
| OCH$_3$ | CH$_3$ | 4-CN-Thien-2-yl |
| OCH$_3$ | CH$_3$ | 5-CH$_3$-Thien-2-yl |
| OCH$_3$ | CH$_3$ | 5-Cl-Thien-2-yl |
| OCH$_3$ | CH$_3$ | 5-CN-Thien-2-yl |
| OCH$_3$ | CH$_3$ | 3-Thienyl |
| OCH$_3$ | CH$_3$ | 5-CH$_3$-Thien-3-yl |
| OCH$_3$ | CH$_3$ | 5-Cl-Thien-3-yl |
| OCH$_3$ | CH$_3$ | 5-CN-Thien-3-yl |
| OCH$_3$ | CH$_3$ | 1-Methylpropyl-2-yl |
| OCH$_3$ | CH$_3$ | 1-Methylpropyl-3-yl |
| OCH$_3$ | CH$_3$ | 2-Oxazolyl |
| OCH$_3$ | CH$_3$ | 4-CH$_3$-Oxazol-2-yl |
| OCH$_3$ | CH$_3$ | 4-Cl-Oxazol-2-yl |
| OCH$_3$ | CH$_3$ | 4-CN-Oxazol-2-yl |
| OCH$_3$ | CH$_3$ | 5-CH$_3$-Oxazol-2-yl |
| OCH$_3$ | CH$_3$ | 5-Cl-Oxazol-2-yl |
| OCH$_3$ | CH$_3$ | 5-CN-Oxazol-2-yl |
| OCH$_3$ | CH$_3$ | 4-Oxazolyl |
| OCH$_3$ | CH$_3$ | 2-CH$_3$-Oxazol-4-yl |
| OCH$_3$ | CH$_3$ | 2-Cl-Oxazol-4-yl |
| OCH$_3$ | CH$_3$ | 2-CN-Oxazol-4-yl |
| OCH$_3$ | CH$_3$ | 5-Oxazolyl |
| OCH$_3$ | CH$_3$ | 2-CH$_3$-Oxazol-5-yl |
| OCH$_3$ | CH$_3$ | 2-Cl-Oxazol-5-yl |
| OCH$_3$ | CH$_3$ | 2-CN-Oxazol-5-yl |
| OCH$_3$ | CH$_3$ | 3-Isoxazolyl |
| OCH$_3$ | CH$_3$ | 5-CH$_3$-Isoxazol-3-yl |
| OCH$_3$ | CH$_3$ | 5-Cl-Isoxazol-3-yl |
| OCH$_3$ | CH$_3$ | 5-CN-Isoxazol-3-yl |
| OCH$_3$ | CH$_3$ | 5-Isoxazolyl |
| OCH$_3$ | CH$_3$ | 3-CH$_3$-Isoxazol-5-yl |
| OCH$_3$ | CH$_3$ | 3-Cl-Isoxazol-5-yl |
| OCH$_3$ | CH$_3$ | 3-CN-Isoxazol-5-yl |
| OCH$_3$ | CH$_3$ | 2-Thiazolyl |
| OCH$_3$ | CH$_3$ | 4-CH$_3$-Thiazol-2-yl |
| OCH$_3$ | CH$_3$ | 4-Cl-Thiazol-2-yl |
| OCH$_3$ | CH$_3$ | 4-CN-Thiazol-2-yl |
| OCH$_3$ | CH$_3$ | 5-CH$_3$-Thiazol-2-yl |
| OCH$_3$ | CH$_3$ | 5-Cl-Thiazol-2-yl |
| OCH$_3$ | CH$_3$ | 5-CN-Thiazol-2-yl |
| OCH$_3$ | CH$_3$ | 4-Thiazolyl |
| OCH$_3$ | CH$_3$ | 2-CH$_3$-Thiazol-4-yl |
| OCH$_3$ | CH$_3$ | 2-Cl-Thiazol-4-yl |
| OCH$_3$ | CH$_3$ | 2-CN-Thiazol-4-yl |
| OCH$_3$ | CH$_3$ | 2-SCH$_3$-Thiazol-4-yl |
| OCH$_3$ | CH$_3$ | 5-Thiazolyl |
| OCH$_3$ | CH$_3$ | 2-CH$_3$-Thiazol-5-yl |
| OCH$_3$ | CH$_3$ | 2-Cl-Thiazol-5-yl |
| OCH$_3$ | CH$_3$ | 2-CN-Thiazol-5-yl |
| OCH$_3$ | CH$_3$ | 3-Isothiazolyl |
| OCH$_3$ | CH$_3$ | 5-CH$_3$-Isothiazol-3-yl |
| OCH$_3$ | CH$_3$ | 5-Cl-Isothiazol-3-yl |
| OCH$_3$ | CH$_3$ | 5-CN-Isothiazol-3-yl |
| OCH$_3$ | CH$_3$ | 5-Isothiazolyl |
| OCH$_3$ | CH$_3$ | 3-CH$_3$-Isothiazol-5-yl |
| OCH$_3$ | CH$_3$ | 3-Cl-Isothiazol-5-yl |
| OCH$_3$ | CH$_3$ | 3-CN-Isothiazol-5-yl |
| OCH$_3$ | CH$_3$ | 2-Imidazolyl |
| OCH$_3$ | CH$_3$ | 4-CH$_3$-Imidazol-2-yl |
| OCH$_3$ | CH$_3$ | 4-Cl-Imidazol-2-yl |
| OCH$_3$ | CH$_3$ | 4-CN-Imidazol-2-yl |
| OCH$_3$ | CH$_3$ | 1-CH$_3$-Imidazol-2-yl |
| OCH$_3$ | CH$_3$ | 1-CH$_3$, 4-Cl-Imidazol-2-yl |
| OCH$_3$ | CH$_3$ | 1,4-(CH$_3$)$_2$-Imidazol-2-yl |
| OCH$_3$ | CH$_3$ | 1-CH$_3$, 5-Cl-Imidazol-2-yl |
| OCH$_3$ | CH$_3$ | 1,5-(CH$_3$)$_2$-Imidazol-2-yl |
| OCH$_3$ | CH$_3$ | 4-Imidazolyl |
| OCH$_3$ | CH$_3$ | 2-CH$_3$-Imidazol-4-yl |

TABLE A-continued

| | | |
|---|---|---|
| OCH$_3$ | CH$_3$ | 2-Cl-Imidazol-4-yl |
| OCH$_3$ | CH$_3$ | 1-CH$_3$-Imidazol-4-yl |
| OCH$_3$ | CH$_3$ | 1,2-(CH$_3$)$_2$-Imidazol-4-yl |
| OCH$_3$ | CH$_3$ | 1-CH$_3$, 2-Cl-Imidazol-4-yl |
| OCH$_3$ | CH$_3$ | 1-CH$_3$-Imidazol-5-yl |
| OCH$_3$ | CH$_3$ | 1-CH$_3$, 3-Cl-Imidazol-5-yl |
| OCH$_3$ | CH$_3$ | 1,2-(CH$_3$)$_2$-Imidazol-5-yl |
| OCH$_3$ | CH$_3$ | 3-Pyrazolyl |
| OCH$_3$ | CH$_3$ | 5-CH$_3$-Pyrazol-3-yl |
| OCH$_3$ | CH$_3$ | 5-Cl-Pyrazol-3-yl |
| OCH$_3$ | CH$_3$ | 5-CN-Pyrazol-3-yl |
| OCH$_3$ | CH$_3$ | 1-CH$_3$-Pyrazol-3-yl |
| OCH$_3$ | CH$_3$ | 1-CH$_3$, 4-Cl-Pyrazol-3-yl |
| OCH$_3$ | CH$_3$ | 1-CH$_3$, 5-Cl-Pyrazol-3-yl |
| OCH$_3$ | CH$_3$ | 1,5-(CH$_3$)$_2$-Pyrazol-3-yl |
| OCH$_3$ | CH$_3$ | 1-CH$_3$-Pyrazol-5-yl |
| OCH$_3$ | CH$_3$ | 1-CH$_3$, 3-Cl-Pyrazol-5-yl |
| OCH$_3$ | CH$_3$ | 1,3-(CH$_3$)$_2$-Pyrazol-5-yl |
| OCH$_3$ | CH$_3$ | 4-Pyrazolyl |
| OCH$_3$ | CH$_3$ | 3-Cl-Pyrazol-4-yl |
| OCH$_3$ | CH$_3$ | 3-CH$_3$-Pyrazol-4-yl |
| OCH$_3$ | CH$_3$ | 1-CH$_3$-Pyrazol-4-yl |
| OCH$_3$ | CH$_3$ | 1-CH$_3$, 3-Cl-Pyrazol-4-yl |
| OCH$_3$ | CH$_3$ | 1,3-(CH$_3$)$_2$-Pyrazol-4-yl |
| OCH$_3$ | CH$_3$ | 1,3,4-Oxadiazol-5-yl |
| OCH$_3$ | CH$_3$ | 2-CH$_3$-1,3,4-Oxadiazol-5-yl |
| OCH$_3$ | CH$_3$ | 2-Cl-1,3,4-Oxadiazol-5-yl |
| OCH$_3$ | CH$_3$ | 2-CF$_3$-1,3,4-Oxadiazol-5-yl |
| OCH$_3$ | CH$_3$ | 2-i-C$_3$H$_7$-1,3,4-Oxadiazol-5-yl |
| OCH$_3$ | CH$_3$ | 2-OCH$_3$-1,3,4-Oxadiazol-5-yl |
| OCH$_3$ | CH$_3$ | 1,2,4-Oxadiazol-3-yl |
| OCH$_3$ | CH$_3$ | 5-CH$_3$-1,2,4-Oxadiazol-3-yl |
| OCH$_3$ | CH$_3$ | 5-i-C$_3$H$_7$-1,2,4-Oxadiazol-3-yl |
| OCH$_3$ | CH$_3$ | 5-Cl-1,2,4-Oxadiazol-3-yl |
| OCH$_3$ | CH$_3$ | 5-CF$_3$-1,2,4-Oxadiazol-3-yl |
| OCH$_3$ | CH$_3$ | 1,2,4-Triazol-3-yl |
| OCH$_3$ | CH$_3$ | 1-CH$_3$-1,2,4-Triazol-3-yl |
| OCH$_3$ | CH$_3$ | 1-Pyrrolyl |
| OCH$_3$ | CH$_3$ | 3-CH$_3$-Pyrrol-1-yl |
| OCH$_3$ | CH$_3$ | 1-Pyrazolyl |
| OCH$_3$ | CH$_3$ | 3-CH$_3$-Pyrazol-1-yl |
| OCH$_3$ | CH$_3$ | 3-CF$_3$-Pyrazol-1-yl |
| OCH$_3$ | CH$_3$ | 4-CH$_3$-Pyrazol-1-yl |
| OCH$_3$ | CH$_3$ | 4-Cl-Pyrazol-1-yl |
| OCH$_3$ | CH$_3$ | 4-Ethoxycarbonyl-Pyrazol-1-yl |
| OCH$_3$ | CH$_3$ | 3-CH$_3$, 4-Br-Pyrazol-1-yl |
| OCH$_3$ | CH$_3$ | 1-Imidazolyl |
| OCH$_3$ | CH$_3$ | 4-CH$_3$-Imidazol-1-yl |
| OCH$_3$ | CH$_3$ | 4,5-Cl$_2$-Imidazol-1-yl |
| OCH$_3$ | CH$_3$ | 2,4-(CH$_3$)$_2$-Imidazol-1-yl |
| OCH$_3$ | CH$_3$ | 1,2,4-Triazol-1-yl |
| OCH$_3$ | CH$_3$ | 1,3,4-Triazol-1-yl |
| OCH$_3$ | CH$_3$ | 3,5-(CH$_3$)$_2$-1,2,4-Triazol-1-yl |
| OCH$_3$ | CH$_3$ | 1-Piperidinyl |
| OCH$_3$ | CH$_3$ | 1-Pyrrolidinyl |
| OCH$_3$ | CH$_3$ | 1-Morpholinyl |

EXAMPLE 1 n-Pentyl 2-(chloromethyl)phenylglyoxylate

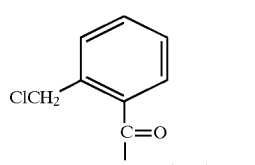

18 g of 1-pentanol (0.2 mol) are taken up with 1.8 g of water in 80 g of toluene. 14.6 g (0.4 mol) of hydrogen chloride are then introduced as a gas (~0° C.). 16.2 g (0.09 mol) of 2-(chloromethyl)benzoyl cyanide are then added dropwise. The mixture is stirred for 2 h at room temperature and heated for 8 h at 60° C.

The reaction mixture is allowed to cool, and is extracted once with 50 ml of 15% strength hydrochloric acid and 3 times with 50 ml of water and concentrated to dryness.

Yield: 23 g (95%, contains 4.9% of pentyl 2-(chloromethyl)benzoate)

Smaller amounts are purified by chromatography, eg. cyclohexane: toluene=2:1 on silica gel 60 (flash).

Larger amounts are purified by distillation.

$^1$H-NMR (CDCl$_3$): δ=0.92 (t, 3H); 1.28–1.48 (m, 4H); 1.67–1.84 (m, 2H); 4.39 (t, 2H); 5.03 (s, 2H); 7.45–7.78 (m, 4H) ppm.

EXAMPLE 2

(2-Ethyl)hexyl 2-(chloromethyl)phenylglyoxylate

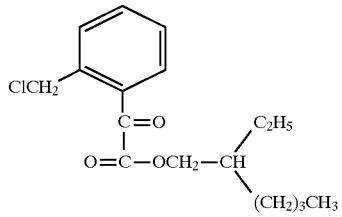

30 g of 2-ethylhexanol (0.23 mol) are dissolved in 80 g of toluene using 2.0 g of water. 14.6 g (0.4 mol) of hydrogen chloride are introduced as a gas at 0°–5° C. and 18 g of 2-(chloromethyl)benzoyl cyanide dissolved in 25 g of toluene are then added dropwise at 0° C.

The reaction mixture is heated to 60° C. with stirring in the course of 2 h. After 8 h at this temperature, it is allowed to cool to room temperature and washed once with 50 ml of 15% strength hydrochloric acid and 3× with 50 ml of water.

Crude product: 33 g (about 88%)

Flash chromatography using cyclohexane (3): toluene (1) on silica gel 60.

Yield: 23 g (75%, purity>99%)

EXAMPLE 3 n-Pentyl 2-methoxyimino-2-[(2'-chloromethyl) phenyl]acetate 33 g (0.4 mol) of O-methylhydroxylamine hydrochloride and 10 g of dry molecular sieve beads (3 Å) were added to a solution of 27 g (0.1 mol) of n-pentyl 2-(chloromethyl) phenylglyoxylate in 50 ml of methanol and the mixture was allowed to stand at room temperature for 16 hours. After filtering off the molecular sieve, the solution was concentrated, the residue was partitioned between methyl tert-butyl ether and water, and the organic phase was washed with water, dried over sodium sulfate and concentrated. 30 g (100%) of the title compound were obtained as a light yellow oil which is present as a 1:1 E/Z isomer mixture. Separation of the isomers is possible by column chromatography on silica gel (methyl tert-butyl ether/n-hexane). E isomer: (colorless oil)

$^1$H-NMR (CDCl$_3$): δ=0.87 (t, 3H); 1.20–1.37 (m, 4H); 1.62–1.74 (m, 2H); 4.05 (s, 3H); 4.27 (t, 2H); 4.44 (s, 2H); 7.16 (dd, 1H); 7.32–7.51 (m, 3H) ppm.

Z isomer: (colorless oil)

$^1$H-NMR (CDCl$_3$): δ=0.89 (t, 3H); 1.24–1.41 (m, 4H); 1.66–1.77 (m, 2H); 4.04 (s, 3H); 4.30 (t, 2H); 4.88 (s, 2H); 7.32–7.47 (m, 3H); 7.58 (d, 1H) ppm.

EXAMPLE 4 n-Pentyl (E)-2-methoxyimino-2-[(2'-chloromethyl) phenyl]acetate

A solution of 30 g (0.1 mol) of n-pentyl 2-methoxyimino-2-[(2'-chloromethyl)phenyl]acetate (E/Z=1:1) in 500 ml of diethyl ether was saturated with hydrogen chloride gas while cooling in ice. The mixture was allowed to come to room temperature and was stirred at room temperature for 16 hours. After concentration and purification by column chromatography on silica gel (methyl tert-butyl ether/n-hexane), 24.3 g (81% yield) of the desired title compound were obtained as a colorless oil.

$^1$H-NMR: see Example 1 (E isomer).

EXAMPLE 5 n-Pentyl (E,E)-2-methoxyimino-2-{[2'-(1''-(4'''-chlorophenyl)-1''-methyl)iminooxymethyl] phenyl}acetate 0.27 g (11 mmol) of sodium hydride was initially introduced into 50 ml of dimethylformamide. 1.7 g of 4-chloroacetophenone oxime were added in portions and the mixture was stirred at room temperature for 30 minutes. 3.0 g (10 mmol) of n-pentyl (E)-2-methoxyimino-2-9[(2'-chloromethyl)phenyl]acetate in 10 ml of dimethylformamide were then added dropwise. The mixture was stirred at room temperature for 2 hours, poured onto cold 2M hydrochloric acid and extracted with methyl tert-butyl ether. The combined organic phases were washed with water, dried over Na$_2$SO$_4$ and concentrated. After purification by column chromatography on silica gel (methyl tert-butyl ether/n-hexane), 3.5 g (80%) of the title compound were obtained as a colorless oil.

$^1$H-NMR (CDCl$_3$): δ=0.84 (t, 3H); 1.16–1.36 (m, 4H); 1.53–1.72 (m, 2H); 2.18 (s, 3H); 4.02 (s, 3H); 4.19 (t, 2H); 5.12 (s, 2H); 7.17–7.59 (m, 8H) ppm.

EXAMPLE 6

(E,E)-2-Methoxyimino-2-{[2'-(1''-(4'''-chlorophenyl)-1''-methyl)iminooxymethyl]phenyl}acetic acid monomethylamide 2.0 g (4.6 mmol) of n-pentyl (E,E)-2-methoxyimino-2-{[2'-(1''-(4'''-chlorophenyl)-1''-methyl)iminooxymethyl [phenyl}acetate were dissolved in 50 ml of tetrahydrofuran, treated with 20 ml of 40% strength aqueous monomethylamine solution and stirred at room temperature for 3 hours. The mixture was then treated with water and extracted with methyl tert-butyl ether. The combined organic phases were washed with water, dried over sodium sulfate and concentrated. 1.6 g (92%) of the title compound were thus obtained as a white powder of melting point 117°–119° C.

$^1$H-NMR (CDCl$_3$): δ=2.17 (s, 3H); 2.86 (d, 3H); 3.94 (s, 3H); 5.11 (s, 2H); 6.72 (s, br, 1H); 7.19–7.55 (m, 8H) ppm.

EXAMPLE 7

(Z)-2-Methoxyimino-2-{[2'-(E)-(1''-(4'''-chlorophenyl)-1''-methyl)iminooxymethyl] phenyl}acetic acid monomethylamide 0.09 g (3.7 mmol) of sodium hydride was initially introduced into 10 ml of dimethylformamide. 0.58 g of 4-chloroacetophenone oxime was added in portions and the mixture was stirred at room temperature for 30 minutes. 1.0 g (3.4 mmol) of n-pentyl (Z)-2-methoxyimino-2-[(2'-chloromethyl)phenyl]acetate in 10 ml of dimethylformamide was then added dropwise, and the mixture was stirred at room temperature for 30 minutes, treated with 10 ml of tetrahydrofuran and 10 ml of 40% strength aqueous monomethylamine solution and stirred at room temperature for 16 hours. After treating with water, it was extracted with methyl tert-butyl ether. The combined organic phases were washed with water, dried over sodium sulfate and concentrated. After purification by column chromatography on silica gel (methyl tert-butyl ether/n-hexane), 1.0 g (79% yield) of the title compound was obtained as a beige powder of melting point 111°–113° C.

$^1$H-NMR (CDCl$_3$): δ=2.23 (s, 3H); 2.80 (d, 3H); 4.04 (s, 3H); 5.39 (s, 2H); 6.68 (s, br, 1H); 7.30–7.55 (m, 8H) ppm.

EXAMPLE 8

(E,E)-2-Methoxyimino-2-{[2'-(1"-(4,"'-chlorophenyl)-1"-methyl)iminooxymethyl]phenyl}acetic acid monomethylamide 50 ml of a saturated ethereal hydrogen chloride solution were added to a solution of 8.4 g (0.022 mol) of (Z)-2-methoxyimino-2-{[2'-(E)-(1"-(4"'-chlorophenyl)-1"methyl)iminooxymethyl]phenyl}acetic acid monomethylamide in 300 ml of toluene and the mixture was allowed to stand at room temperature for 4 hours. After addition of methyl tert-butyl ether, it was washed with saturated NaHCO$_3$ solution and then washed with water until neutral, and the organic phase was separated off, dried over Na$_2$SO$_4$ and concentrated. After purification by column chromatography on silica gel (methyl tert-butyl ether/n-hexane), 5.4 g (65% yield) of the title compound were obtained as colorless crystals of melting point 117° to 119° C.

$^1$H-NMR (CDCl$_3$): δ=2.17 (s, 3H); 2.86 (d, 3H); 3.94 (s, 3H); 5.11 (s, 2H); 6.71 (sbr, 1H); 7.19–7.55 (m, 8H) ppm.

EXAMPLE 9

2-(Chloromethyl)phenylglyoxylamide 16.5 g (92 mmol) of 2-(chloromethyl)benzoyl cyanide, 150 ml of concentrated hydrochloric acid and 150 ml of saturated ethereal hydrogen chloride solution were mixed together and stirred at room temperature for 5 hours. The mixture was then poured into water, the organic phase was separated off and the aqueous phase was extracted with methyl tert-butyl ether. The combined organic phases were washed with water, dried over sodium sulfate and concentrated. After purification by column chromatography on silica gel (methyl tert-butyl ether/n-hexane), 13.4 g (74% yield) of the title compound were obtained as a beige powder of melting point 105°–107° C.

$^1$H-NMR (CDCl$_3$): δ=4.90 (s, 2H); 5.79 (s, br, 1H); 7.03 (s, br, 1H); 7.46–7.69 (m, 3H); 8.02 (d, 1H) ppm.

EXAMPLE 10 n-Pentyl 2-(chloromethyl)phenylglyoxylate 1.5 g (7.6 mmol) of 2-(chloromethyl)phenylglyoxylamide were initially introduced into 200 ml of n-pentanol. Hydrogen chloride was then introduced into the mixture as a gas until it was saturated, the temperature rising to 80° C. The mixture was then stirred for a further 3 hours and concentrated, the residue was treated with water and the mixture was extracted with methyl tert-butyl ether. The combined organic phases were washed with water, dried over sodium sulfate and concentrated. After purification by column chromatography on silica gel (methyl tert-butyl ether/n-hexane), 1.1 g (54% yield) of the title compound were obtained as a colorless oil.

$^1$H-NMR (CDCl$_3$): δ=0.92 (t, 3H); 1.28–1.48 (m, 4H); 1.67–1.84 (m, 2H); 4.39 (t, 2H); 5.03 (s, 2H); 7.45–7.78 (m, 4H) ppm.

EXAMPLE 11

(E,E,E)-2-[[[[2-(Methoxyimino)-1,2-(dimethyl)ethylidene]amino]oxy]methyl]-α-methoxyiminophenylacetic acid monomethylamide A total of 1.4 g (10 mmol) of potassium carbonate and 0.7 g (5.4 mmol) of (E,E)-2-hydroxyimino-3-methoxyiminobutane were initially introduced into 15 ml of dimethylformamide and the mixture was stirred at 50° C. for 1 h. 1.5 g (5.0 mmol) of n-pentyl (E)-2-methoxyimino-2-[(2-chloromethyl)phenyl]acetate, dissolved in 5 ml of dimethylformamide, were then added and the mixture was stirred at room temperature for a total of 48 h. 20 ml of 40% strength aqueous monomethylamine solution were then added and the mixture was stirred at room temperature for 1 h. After treating with water, it was extracted with methyl tert-butyl ether. The combined organic phases were washed with water, dried over sodium sulfate and concentrated. After purification by column chromatography on silica gel (methyl tert-butyl ether/n-hexane), 1.5 g (91% yield) of the title compound were obtained as a white powder of melting point from 67° to 69° C.

$^1$H-NMR (CDCl$_3$): δ=1.95 (s, 3H); 1.98 (s, 3H); 2.90 (d, 3H); 3.92 (s, 3H); 3.94 (s, 3H); 5.05 (s, 2H); 6.70 (s, br, 1H); 7.13–7.45 (m, 4H) ppm.

EXAMPLE 12

(E,E,E)-2-[[[[(2-(Methoxyimino)-1-(methyl)-2-(phenyl)ethylidene]-amino]oxy]methyl]-α-methoxyiminophenylacetic acid monoethylamide A total of 2.2 g (16 mmol) of potassium carbonate and 0.65 g (3.4 mmol) of (E,E)-1-phenyl-1-methoxyiminopropan-2-one-2-oxime were initially introduced into 30 ml of dimethylformamide and the mixture was stirred at 60° C. for 1 hour. 1.0 g (3.4 mmol) of n-pentyl (E)-2-methoxyimino-2-[(2-chloromethyl)phenyl]acetate, dissolved in 20 ml of dimethylformamide, were then added and the mixture was stirred at room temperature for 28 hours and at 60° C. for 17 hours. After cooling, 50 ml of tetrahydrofuran and 15 ml of 40% strength aqueous monomethylamine solution were then added and the mixture was stirred at room temperature for 24 hours. After treating with water, it was extracted with methyl tert-butyl ether. The combined organic phases were washed with water, dried over sodium sulfate and concentrated. After purification by column chromatography on silica gel (methyl tert-butyl ether/n-hexane), 1.0 g (75% yield) of the title compound was obtained as a white powder of melting point from 127° to 130° C.

$^1$H-NMR (CDCl$_3$): δ=2.10 (s, 3H); 2.84 (d, 3H); 3.87 (s, 3H); 3.89 (s, 3H); 4.91 (s, 2H); 6.62 (s, br, 1H); 7.12–7.33 (m, 9H) ppm.

EXAMPLE 13 n-Pentyl (E)-2-[[[1-Phenyl-1,2,4-triazol-3-yl]oxy]methyl]-α-methoxyiminophenylacetate 0.80 g (5.0 mmol) of 3-hydroxy-1-phenyl-1,2,4-triazole and 3.5 g (25 mmol) of potassium carbonate were initially introduced in 40 ml of dimethylformamide and the mixture was stirred at room temperature for 10 minutes. 1.5 g (5.0 mmol) of n-pentyl (E)-2-methoxyimino-2-[(2-chloromethyl)phenyl]acetate, dissolved in 10 ml of dimethylformamide, and a spatula-tipful of potassium iodide were then added and the mixture was heated at 100° C. for 6 hours. After treating with water, it was extracted with methyl tert-butyl ether. The combined organic phases were washed with water, dried over sodium sulfate and concentrated. After purification by column chromatography on silica gel (methyl tert-butyl ether/n-hexane), 1.7 g (80% yield) of the title compound were obtained as a yellow oil.

$^1$H-NMR (CDCl$_3$): δ=0.83 (t, 3H); 1.21–1.32 (m, 4H); 1.60–1.71 (m, 2H); 4.04 (s, 3H); 4.23 (t, 2H); 5.26 (s, 2H); 7.17–7.70 (m, 9H); 8.25 (s, 1H) ppm.

EXAMPLE 14

(E)-2-[[[(1-Phenyl-1,2,4-triazol-3-yl]oxy]methyl]-α-methoxyiminophenylacetic monomethylamide 1.5 g (3.6 mmol) of the pentyl ester from Example 13 were dissolved in 50 ml of tetrahydrofuran, and the mixture was treated with 10 ml of 40% strength aqueous monomethylamine solution and stirred at room temperature for 16 hours. It was then treated with water, extracted with methyl tert-butyl ether, and the organic phase was washed with water, dried over sodium sulfate and concentrated in a rotary evaporator. As a residue, 1.1 g (86% yield) of the title compound remained as a yellow oil.

$^1$H-NMR (CDCl$_3$): δ=2.90 (d, 3H); 3.96 (s, 3H); 5.30 (s, 2H); 6.87 (s, br, 1H); 7.25–7.68 (m, 9H); 8.21 (s, 1H) ppm.

we claim:

1. A process for preparing α-methoxyiminocarboxylic acid methylamides of the formula I

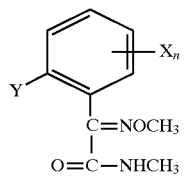

(I)

where

X is nitro, trifluoromethyl, halogen, C$_1$–C$_4$-alkyl or C$_1$–C$_4$-alkoxy, n is 0 or an integer of from 1 to 4, where the X radicals can be different if n>1, and where Y is a C-organic radical, by Pinner reaction of an acyl cyanide of the formula II

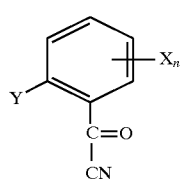

(II)

with an alcohol and subsequent reaction of the ester formed in the Pinner reaction, of the formula IV

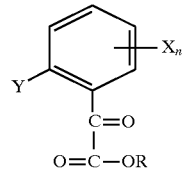

(IV)

a) with hydroxylamine to give the oxime of the formula V

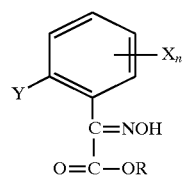

(V)

methylation of V to give the oxime ether of the formula VI

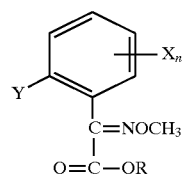

(VI)

or b) with O-methylhydroxylamine to give the oxime ether of the formula VI and subsequent reaction of VI with methylamine, which comprises using in the Pinner reaction an alcohol of the formula III

R—OH (III)

whose boiling point is above 75° C.

2. A process for preparing α-methoxyiminocarboxylic acid methylamides of the formula I as claimed in claim 1, by Pinner reaction of an acyl cyanide of the formula II

(II)

with an alcohol and subsequent reaction of the mixture formed in the Pinner reaction, of the ester of the formula IV

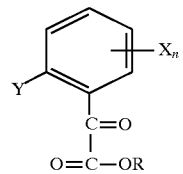

(IV)

and the amide of the formula IV'

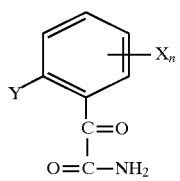 (IV')

a) with hydroxylamine to give the oxime of the formula V

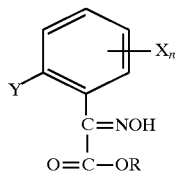 (V)

methylation of V to give the oxime ether of the formula VI

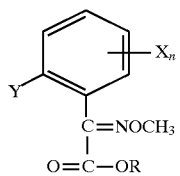 (VI)

or b) with O-methylhydroxylamine to give the oxime ether of the formula VI and subsequent reaction of VI with methylamine, wherein in the Pinner reaction an alcohol of the formula III

R—OH (III)

is used whose boiling point is above 75° C.

3. A process for preparing α-methoxyiminocarboxylic acid methylamides of the formula I as claimed in claim 1, wherein the reaction to give the oxime of the formula V is carried out in the presence of the alcohol III which was used in the Pinner reaction.

4. A process for preparing α-methoxyiminocarboxylic acid methylamides of the formula I as claimed in claim 1, wherein the reaction to give the oxime ether of the formula VI is carried out in the presence of the alcohol III which was used in the Pinner reaction.

5. A process as claimed in claim 1, wherein an alcohol III is used whose boiling point is above 90° C.

6. A process for preparing α-methoxyiminocarboxylic acid methylamides of the formula IA

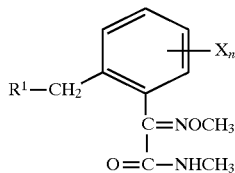 (IA)

where the substituents and the index have the following meanings:

X is nitro, trifluoromethyl, halogen, $C_1$–$C_4$-alkyl or $C_1$–$C_4$-alkoxy, n is 0 or an integer of from 1 to 4, where the X radicals can be different if n>1, $R^1$ is hydrogen, hydroxyl, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl or unsubstituted or substituted hetaryloxy,

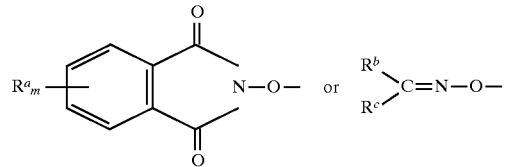

$R^a$ is cyano, nitro, halogen, $C_1$–$C_4$-alkyl, $C_1$–$C_4$-haloalkyl, $C_1$–$C_4$-alkoxy or $C_1$–$C_4$-haloalkoxy, m is 0 or an integer of from 1 to 4, where the $R^a$ radicals can be different if m>1, $R^b$ is hydrogen, unsubstituted or substituted alkyl, cycloalkyl, alkenyl, cycloalkenyl, alkynyl, heterocyclyl, alkylcarbonyl, cycloalkylcarbonyl, alkenylcarbonyl, alkynylcarbonyl, heterocyclylcarbonyl, alkoxycarbonyl, aryl, hetaryl, arylcarbonyl, hetarylcarbonyl, arylsulfonyl, hetarylsulfonyl or a C(R')=NOR'' group;

$R^1$ is hydrogen, hydroxyl, cyano, nitro, amino, halogen, unsubstituted or substituted alkyl, alkoxy, alkylthio, alkylamino, dialkylamino, alkenyl, alkenyloxy, alkenylthio, alkenylamino, alkynyl, alkynyloxy, alkynylthio, alkynylamino, cycloalkyl, cycloalkoxy, cycloalkylthio, cycloalkylamino, cycloalkenyl, cycloalkenyloxy, cycloalkenylthio, cycloalkenylamino, heterocyclyl, heterocyclyloxy, heterocyclylthio, heterocyclylamino, aryl, aryloxy, arylthio, arylamino, heteroaryl, heteroaryloxy, heteroarylthio or heteroarylamino;

R'' is hydrogen, unsubstituted or substituted alkyl, cycloalkyl, alkenyl, alkynyl, heterocyclyl, aryl or heteroaryl, $R^c$ is a group mentioned under $R^b$ or hydroxyl, cyano, nitro, amino, halogen, unsubstituted or substituted alkoxy, alkylthio, alkylamino, dialkylamino, aryloxy, arylthio, arylamino, hetaryloxy, hetarylthio or hetarylamino; unsubstituted or substituted alkyl, cycloalkyl, alkenyl, cycloalkenyl, alkynyl, alkylcarbonyl, alkenylcarbonyl, alkynylcarbonyl, alkoxycarbonyl, aryl, hetaryl, arylcarbonyl, hetarylcarbonyl, arylsulfonyl or hetarylsulfonyl, or $R^b$ and $R^c$, together with the C atom to which they are bonded, are a carbocyclic or heterocyclic ring, by Pinner reaction of an acyl cyanide of the formula IIA

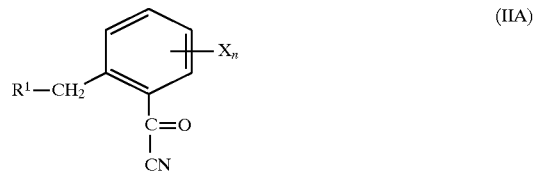 (IIA)

with an alcohol and subsequent reaction of the ester formed in the Pinner reaction, of the formula IVA

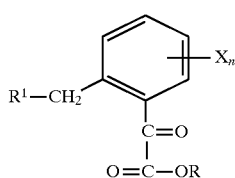

a) with hydroxylamine to give the oxime of the formula VA

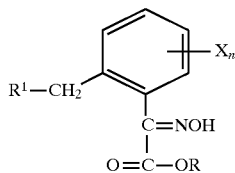

methylation of VA to give the oxime ether of the formula VIA

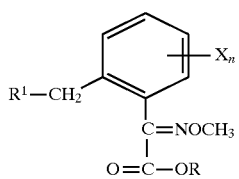

or b) with O-methylhydroxylamine to give the oxime ether of the formula VIA and subsequent reaction of VIA with methylamine, wherein in the Pinner reaction an alcohol of the formula III

R—OH    (III)

is used whose boiling point is above 75° C.

7. A process for preparing α-methoxyiminocarboxylic acid methylamides of the formula IA as claimed in claim 6, by Pinner reaction of an acyl cyanide of the formula IIA

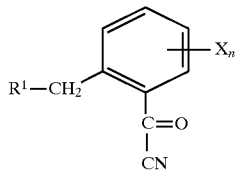

with an alcohol and subsequent reaction of the mixture formed in the Pinner reaction, of the ester of the formula IVA

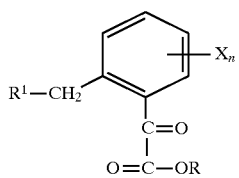

and the amide of the formula IV'A

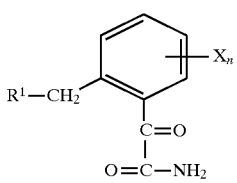

a) with hydroxylamine to give the oxime of the formula VA

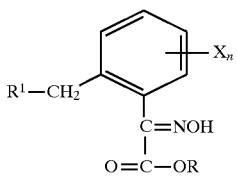

methylation of VA to give the oxime ether of the formula VIA

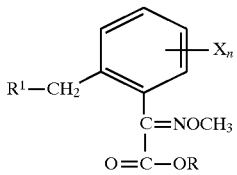

or b) with O-methylhydroxylamine to give the oxime ether of the formula VI and subsequent reaction of VIA with methylamine, wherein in the Pinner reaction an alcohol of the formula III

R—OH    (III)

is used whose boiling point is above 75° C.

8. A process for preparing α-methoxyiminocarboxylic acid methylamides of the formula IA as claimed in claim 6, wherein the reaction to give the oxime of the formula VA is carried out in the presence of the alcohol III which was used in the Pinner reaction.

9. A process for preparing α-methoxyiminocarboxylic acid methylamides of the formula IA as claimed in claim 6, wherein the reaction to give the oxime ether of the formula VIA is carried out in the presence of the alcohol III which was used in the Pinner reaction.

10. A process as claimed in claim 6, wherein an alcohol III is used whose boiling point is above 90° C.

11. A compound of the formula (X)

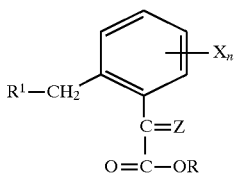

where the index n and the substituent X have the meanings given in claim 6,

Z is O or NOCH$_3$,

R is the radical of an alcohol, R—OH of the formula III, whose boiling point is above 75° C., and R$^1$ is hydroxy, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl, unsubstituted or substituted hetaryloxy or a group

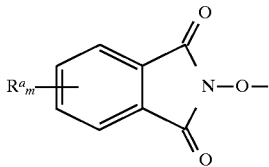

where m is 0 or an integer of from 1 to 4, where the $R^a$ radicals may be different when m>1, and $R^a$ is cyano, nitro, halogen, $C_1$–$C_4$-alkyl, $C_1$–$C_4$-haloalkyl, $C_1$–$C_4$-alkoxy or $C_1$–$C_4$-haloalkoxy.

12. A The process defined in claim 6 wherein the substituents R and $R^1$ of the compound of the formula IVA have the following meanings:

R is the radical of an alcohol, R—OH of the formula III, whose boiling point is above 75° C., and $R^1$ is hydroxy, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl, unsubstituted or substituted hetaryloxy or a group:

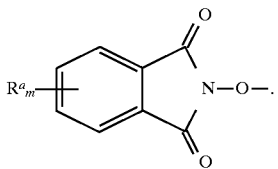

13. The process defined in claim 6 wherein the substituents R and $R^1$ of the compound of the formula VIA have the following meanings:

R is the radical of an alcohol, R—OH of the formula III, whose boiling point is above 75° C., and $R^1$ is hydroxy, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl, unsubstituted or substituted hetaryloxy or a group:

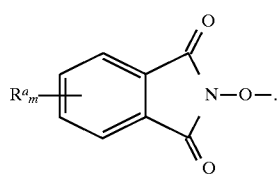

14. A compound of the formula VA as defined in claim 6 where

R is the radical of an alcohol, R—OH of the formula III, whose boiling point is above 75° C., and $R^1$ is hydrogen, hydroxy, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl, unsubstituted or substituted hetaryloxy or a group:

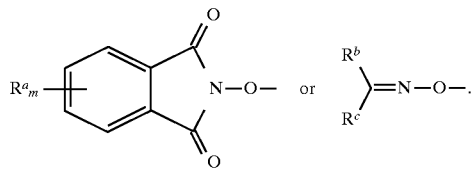

15. The process defined in claim 6 wherein the substituents R and $R^1$ of the compound of the formula VA have the following meanings:

R is the radical of an alcohol, R—OH of the formula III, whose boiling point is above 75° C., and $R^1$ is hydrogen, hydroxy, mercapto, cyano, nitro, halogen, unsubstituted or substituted alkylsulfonyl, unsubstituted or substituted cycloalkyl, unsubstituted or substituted aryloxy, unsubstituted or substituted arylsulfonyl, unsubstituted or substituted heterocyclyl, unsubstituted or substituted hetaryloxy or a group:

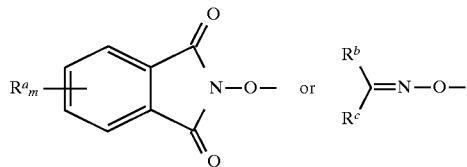

* * * * *

UNITED STATES PATENT AND TRADEMARK OFFICE
CERTIFICATE OF CORRECTION

PATENT NO.: 5,856,560

DATED: January 5, 1999

INVENTOR(S): BAYER et al.

It is certified that error appears in the above-identified patent and that said Letters Patent is hereby corrected as shown below:

On the cover page, item [22], "Filed: Dec. 10, 1996" should be
--PCT Filed: May 26, 1995--.
On the cover page, insert the following PCT information:
--[86] PCT No.: PCT/EP 95/02013
§ 371 Date: Dec. 10, 1996
§ 102(e) Date: Dec. 10, 1996
[87] PCT Pub. No.: WO 95/34526
PCT Pub. Date: Dec. 21, 1995--.

Signed and Sealed this

Twenty-ninth Day of June, 1999

Attest:

Q. TODD DICKINSON

*Attesting Officer*     *Acting Commissioner of Patents and Trademarks*